United States Patent
Mylonakis et al.

(10) Patent No.: US 11,419,834 B2
(45) Date of Patent: Aug. 23, 2022

(54) **METHODS FOR TREATING DISEASES OR INFECTIONS CAUSED BY OR ASSOCIATED WITH *H. PYLORI* USING A HALOGENATED SALICYLANILIDE**

(71) Applicant: Rhode Island Hospital, Providence, RI (US)

(72) Inventors: Eleftherios Mylonakis, Providence, RI (US); Nagendran Tharmalingam, East Providence, RI (US)

(73) Assignee: RHODE ISLAND HOSPITAL, Providence, RI (US)

( * ) Notice: Subject to any disclaimer, the term of this patent is extended or adjusted under 35 U.S.C. 154(b) by 0 days.

(21) Appl. No.: 16/798,651

(22) Filed: Feb. 24, 2020

(65) Prior Publication Data

US 2020/0268693 A1 Aug. 27, 2020

Related U.S. Application Data

(60) Provisional application No. 62/809,864, filed on Feb. 25, 2019.

(51) Int. Cl.
| | | |
|---|---|---|
| *A61K 31/167* | (2006.01) | |
| *A61K 31/4439* | (2006.01) | |
| *A61P 31/04* | (2006.01) | |
| *A61K 31/4164* | (2006.01) | |
| *A61K 31/444* | (2006.01) | |

(52) U.S. Cl.
CPC ........ *A61K 31/167* (2013.01); *A61K 31/4164* (2013.01); *A61K 31/444* (2013.01); *A61K 31/4439* (2013.01); *A61P 31/04* (2018.01)

(58) Field of Classification Search
CPC .............. A61K 31/167; A61K 31/4164; A61K 31/4439; A61K 31/444; A61P 31/04
See application file for complete search history.

(56) References Cited

U.S. PATENT DOCUMENTS

| | | |
|---|---|---|
| 2,731,386 A | 1/1956 | Laszlo |
| 3,674,850 A | 7/1972 | Osborne |
| 3,914,418 A | 10/1975 | Patchett et al. |
| 4,287,191 A | 9/1981 | Coburn et al. |
| 4,310,682 A | 1/1982 | Ozawa et al. |
| 4,358,443 A | 11/1982 | Coburn et al. |
| 4,671,957 A | 6/1987 | Holtshousen |
| 4,742,083 A | 5/1988 | Ritchey |
| 4,883,660 A | 11/1989 | Blackman et al. |
| 4,939,132 A | 7/1990 | Coburn et al. |
| 5,958,911 A | 9/1999 | Evans et al. |
| 6,117,859 A | 9/2000 | Evans et al. |
| 6,251,869 B1 | 6/2001 | Bohanon |
| 6,399,629 B1 | 6/2002 | Chamberland et al. |
| 6,492,425 B1 | 12/2002 | Callahan et al. |
| 6,534,489 B1 | 3/2003 | Jomaa |
| 6,830,758 B2 | 12/2004 | Nichols et al. |
| 8,097,759 B2 | 1/2012 | Muto et al. |
| 8,198,326 B2 | 6/2012 | Scholz |
| 8,263,657 B2 | 9/2012 | Muto et al. |
| 8,846,646 B2 | 9/2014 | Chiou |
| 9,446,131 B2 | 9/2016 | Hardas et al. |
| 9,949,988 B2 | 4/2018 | Delavenne et al. |
| 10,463,680 B2 | 11/2019 | Sommer et al. |
| 10,758,553 B2 | 9/2020 | Delavenne et al. |
| 10,857,164 B2 | 12/2020 | Sommer et al. |
| 11,045,434 B1 | 6/2021 | Sommer et al. |
| 2002/0192273 A1 | 12/2002 | Buseman et al. |
| 2003/0036533 A1 | 2/2003 | Jomaa |
| 2003/0045746 A1 | 3/2003 | Jomaa |
| 2004/0071757 A1 | 4/2004 | Rolf |
| 2004/0082549 A1 | 4/2004 | Jomaa |
| 2005/0075511 A1 | 4/2005 | Jomaa |
| 2006/0052452 A1 | 3/2006 | Scholz |
| 2006/0122243 A1 | 6/2006 | Muto et al. |
| 2006/0280783 A1 | 12/2006 | Dipietro et al. |
| 2007/0059351 A1 | 3/2007 | Murrell et al. |
| 2010/0029781 A1 | 2/2010 | Morris |
| 2010/0317643 A1 | 12/2010 | Goodacre et al. |
| 2013/0005802 A1 | 1/2013 | Chen et al. |
| 2013/0189368 A1 | 7/2013 | Mosqueira et al. |
| 2014/0135296 A1 | 5/2014 | Deretic et al. |
| 2014/0294957 A1 | 10/2014 | Stein et al. |

(Continued)

FOREIGN PATENT DOCUMENTS

| | | |
|---|---|---|
| CA | 2344867 A1 | 3/2000 |
| CA | 2360661 A1 | 8/2000 |

(Continued)

OTHER PUBLICATIONS

Gwisai; Biomed. Mater. 2017, 12, 045010. DOI: 10.1088/1748-605X/aa7105 (Year: 2017).*
Hu; Front. Cell. Infect. Microbiol., 2017, 7, 168. DOI: 10.3389/fcimb.2017.00168 (Year: 2017).*
Kadri; ChemMedChem 2018, 13, 1088-1091. DOI:10.1002/cmdc.201800100 (Year: 2018).*
Kratky; Bioorg. Med. Chem. 2016, 24, 1322-1330. DOI: 10.1016/j.bmc.2016.02.004 (Year: 2016).*
Sun; Tubercle and Lung Disease 1999, 79, 319-320. DOI: 10.1054/tuld.1999.0212 (Year: 1999).*
Zhu; Bioorg. Med. Chem. 2009, 17, 5139-5145. DOI: 10.1016/j.bmc.2009.05.054 (Year: 2009).*

(Continued)

*Primary Examiner* — Daniel R Carcanague
(74) *Attorney, Agent, or Firm* — Mintz, Levin, Cohn, Ferris, Glovsky and Popeo, P.C.

(57) ABSTRACT

Disclosed are methods for the prevention or treatment of a disease or infection caused by or associated with *H. pylori* in a subject infected by *H. pylori*, the method comprising orally administering a halogenated salicylanilide such as niclosamide to the subject. The method may be used for the prevention or treatment of, for example dyspepsia, gastritis, peptic ulcer disease, premalignant gastric lesions, gastric cancer and gastric mucosa-associated lymphoid tissue (MALT) lymphoma.

28 Claims, 7 Drawing Sheets

Specification includes a Sequence Listing.

(56) References Cited

U.S. PATENT DOCUMENTS

| | | |
|---|---|---|
| 2015/0104492 A1 | 4/2015 | Mcdermott et al. |
| 2015/0250808 A1 | 9/2015 | Deretic et al. |
| 2016/0143987 A1 | 5/2016 | Engelthaler et al. |
| 2016/0199343 A1 | 7/2016 | De Visscher et al. |
| 2016/0303034 A1 | 10/2016 | Collins et al. |
| 2017/0014325 A1 | 1/2017 | Carola et al. |
| 2017/0056347 A1 | 3/2017 | Glick et al. |
| 2017/0172943 A1 | 6/2017 | Hardas et al. |
| 2017/0258816 A1 | 9/2017 | Delavenne et al. |
| 2017/0304372 A1 | 10/2017 | Kim et al. |
| 2018/0207179 A1 | 7/2018 | Sommer et al. |
| 2018/0224470 A1 | 8/2018 | Leung et al. |
| 2019/0151231 A1 | 5/2019 | Sommer et al. |
| 2019/0201422 A1 | 7/2019 | Sommer et al. |
| 2020/0268693 A1 | 8/2020 | Mylonakis et al. |
| 2020/0306269 A1 | 10/2020 | Delavenne et al. |
| 2020/0306270 A1 | 10/2020 | Delavenne et al. |
| 2020/0306271 A1 | 10/2020 | Delavenne et al. |
| 2021/0137948 A1 | 5/2021 | Sommer |

FOREIGN PATENT DOCUMENTS

| | | |
|---|---|---|
| CA | 2399947 A1 | 8/2001 |
| CN | 104053632 A | 9/2014 |
| CN | 104430338 A | 3/2015 |
| DE | 19828097 A1 | 12/1999 |
| DE | 19843334 A1 | 3/2000 |
| DE | 19843360 A1 | 3/2000 |
| DE | 19843383 A1 | 3/2000 |
| DE | 19859426 A1 | 7/2000 |
| EP | 0221211 B1 | 1/1989 |
| EP | 0487973 A1 | 6/1992 |
| EP | 1174439 A2 | 1/2002 |
| EP | 1140952 B1 | 9/2003 |
| EP | 1514544 A1 | 3/2005 |
| EP | 2049137 A2 | 4/2009 |
| EP | 2262754 A2 | 12/2010 |
| EP | 3020398 A1 | 5/2016 |
| FR | 1340175 A1 | 10/1963 |
| GB | 1421589 A | 1/1976 |
| GB | 1527638 A | 10/1978 |
| GB | 2456376 A | 7/2009 |
| GB | 2465633 A | 6/2010 |
| JP | 2002518307 A | 6/2002 |
| JP | 2004331577 A | 11/2004 |
| JP | 2007007189 A | 1/2007 |
| JP | 2009519709 A | 5/2009 |
| JP | 2009533415 A | 9/2009 |
| JP | 2010528098 A | 8/2010 |
| JP | 2011511774 A | 4/2011 |
| JP | 2011526934 A | 10/2011 |
| JP | 2012012338 A | 1/2012 |
| JP | 2012505867 A | 3/2012 |
| JP | 2013529668 A | 7/2013 |
| JP | 2013224320 A | 10/2013 |
| RU | 2227025 C2 | 4/2004 |
| SU | 597671 A1 | 3/1978 |
| WO | 9619220 A1 | 6/1996 |
| WO | 9856390 A1 | 12/1998 |
| WO | 9965449 A2 | 12/1999 |
| WO | 0004031 A1 | 1/2000 |
| WO | 0016757 A2 | 3/2000 |
| WO | 0017212 A1 | 3/2000 |
| WO | 0044358 A2 | 8/2000 |
| WO | 0044359 A2 | 8/2000 |
| WO | 0048636 A1 | 8/2000 |
| WO | 0160157 A2 | 8/2001 |
| WO | 0160829 A1 | 8/2001 |
| WO | 0193872 A1 | 12/2001 |
| WO | 0245662 A2 | 6/2002 |
| WO | 03072113 A1 | 9/2003 |
| WO | 03103665 A1 | 12/2003 |
| WO | 2004006906 A2 | 1/2004 |
| WO | 2004047842 A1 | 6/2004 |
| WO | 2004062600 A2 | 7/2004 |
| WO | 2005025598 A1 | 3/2005 |
| WO | 2005074912 A2 | 8/2005 |
| WO | 2006104763 A1 | 10/2006 |
| WO | 2007066130 A2 | 6/2007 |
| WO | 2007119151 A1 | 10/2007 |
| WO | 2008006848 A1 | 1/2008 |
| WO | 2008021088 A2 | 2/2008 |
| WO | 2008092006 A2 | 7/2008 |
| WO | 2008133982 A2 | 11/2008 |
| WO | 2008155535 A1 | 12/2008 |
| WO | 2009111040 A1 | 9/2009 |
| WO | 2009111064 A2 | 9/2009 |
| WO | 2009140215 A2 | 11/2009 |
| WO | 2010003568 A1 | 1/2010 |
| WO | 2010005836 A2 | 1/2010 |
| WO | 2010043717 A2 | 4/2010 |
| WO | 2010061330 A1 | 6/2010 |
| WO | 2010129062 A1 | 11/2010 |
| WO | 2011098579 A1 | 8/2011 |
| WO | 2012032360 A2 | 3/2012 |
| WO | 2013182990 A1 | 12/2013 |
| WO | 2014121342 A1 | 8/2014 |
| WO | 2014125075 A1 | 8/2014 |
| WO | 2014176634 A1 | 11/2014 |
| WO | 2014200705 A1 | 12/2014 |
| WO | 2015071668 A1 | 5/2015 |
| WO | 2015143654 A1 | 10/2015 |
| WO | 2016004166 A1 | 1/2016 |
| WO | 2016036839 A1 | 3/2016 |
| WO | 2016038035 A1 | 3/2016 |
| WO | 2016080846 A1 | 5/2016 |
| WO | 2016138286 A1 | 9/2016 |
| WO | 2016144569 A1 | 9/2016 |
| WO | 2016144979 A1 | 9/2016 |
| WO | 2016193136 A1 | 12/2016 |
| WO | 2016210247 A1 | 12/2016 |
| WO | 2016210289 A1 | 12/2016 |
| WO | 2017040864 A1 | 3/2017 |
| WO | 2017157997 A1 | 9/2017 |
| WO | 2018051102 A1 | 3/2018 |
| WO | 2018141063 A1 | 8/2018 |
| WO | 2018173069 A1 | 9/2018 |
| WO | 2019038443 A1 | 2/2019 |
| WO | 2019192968 A1 | 10/2019 |
| WO | 2020039073 A1 | 2/2020 |
| WO | 2020091804 A1 | 5/2020 |
| WO | 2021076922 A1 | 4/2021 |
| WO | 2021198116 A1 | 10/2021 |

OTHER PUBLICATIONS van Doorn; Gut 2000, 46, 321-326. DOI: 10.1136/gut.46.3.321 (Year: 2000).*
Garza-González; World J Gastroenterol 2014, 20, 1438-1449. doi:10.3748/wjg.v20.i6.1438 (Year: 2014).*
Cheng; Bioorg. Med. Chem. 2010, 18, 8512-8529. doi:10.1016/j.bmc.2010.10.036 (Year: 2010).*
Enroth, International Encyclopedia of Public Health, 2nd edition, 3:527-531, (2016).
Study ATx201-004, OINTMENT 2% or 4% in Impetigo, 2 pages, (2018).
UK Standards for Microbiology Investigations, Identification of *Clostridium* species, Bacteriology—Identification, Dec. 1, 2015, 8(4):27 pages.
U.S. Appl. No. 17/290,386, "Treatment of Inflammatory Conditions" filed Apr. 30, 2021.
Ahn et al. (Mar. 16, 2017) "Anti-helminthic Niclosamide Inhibits Ras-driven Oncogenic Transformation via Activation of GSK-3", Oncotarget, 8(19):31856-31863.
Akiyama et al. (1999) "Recent Investigations of *Staphylococcus aureus* in Dermatology", Japanese journal of Dermatology, 109(13):2095-2102.
Amieva et al. (Jan. 1, 2008) "Host-Bacterial Interactions in Helicobacter pylori Infection", Gastroenterology, 134(1):306-323.
Andrews et al. (1983) "The Biology and Toxicology of Molluscicides, Bayluscide", Pharmacology & Therapeutics, 19:245-295.

(56) References Cited

OTHER PUBLICATIONS

Backert et al. (Jul. 15, 2016) "The Role of CagA in the Gastric Biology of Helicobacter pylori", Cancer Research, 76(14):4028-4031.
Beers et al. (2003) "The Merck Manual of Medical Information, Second Home Edition", 1222-1223.
Bieber (Apr. 3, 2008) "Atopic Dermatitis: Mechanisms of Disease", The New England Journal of Medicine, 358(14):1483-1494.
Burock et al. (2018) "Niclosamide a New Chemotherapy Agent? Pharmacokinetics of the Potential Anticancer Drug in a Patient Cohort of the NIKOLO Trial", Journal of Clinical Oncology, 36(15_suppl):1 page.
Burock et al. (2018) "Phase II Trial to Investigate the Safety and Efficacy of Orally Applied Niclosamide in Patients with Metachronous or Sychronous Metastases of a Colorectal Cancer Progressing after Therapy: The NIKOLO Trial", BMC Cancer, 18(1):7 pages.
Carvalho et al. (2011) "Nitazoxanide Disrupts Membrane Potential and Intrabacterial pH Homeostasis of *Mycobacterium tuberculosis*", ACS Medicinal Chemistry Letters, 2(11):849-854.
Celli et al. (Aug. 25, 2009) "Helicobacter pylori Moves Through Mucus by Reducing Mucin Viscoelasticity", Proceedings of the National Academy of Sciences, 106(34):14321-14326.
Censini et al. (Dec. 1996) "cag, a Pathogenicity Island of Helicobacter pylori, Encodes Type I-specific and Disease-associated Virulence Factors", Proceedings of the National Academy of Sciences, 93(25):14648-14653.
Chan Francis K. (Oct. 4, 2008) "Proton-pump Inhibitors in Peptic Ulcer Disease", The Lancet, 372(9645):1198-1200.
Cheung Dae Y. (Sep. 2017) "Atrophic Gastritis Increases the Risk of Gastric Cancer in Asymptomatic Population in Korea", Gut and Liver, 11(5):575-576.
Chey et al. (Feb. 2017) "ACG Clinical Guideline: Treatment of Helicobacter pylori Infection", American Journal of Gastroenterology, 112(2):212-238.
Chirife et al. (1983) "In Vitro Antibacterial Activity of Concentrated Polyethylene Glycol 400 Solutions", Antimicrobial Agents and Chemotherapy, 24(3):409-412.
Choi et al. (Mar. 22, 2018) "Helicobacter pylori Therapy for the Prevention of Metachronous Gastric Cancer", The New England Journal of Medicine, 378(12):1085-1095.
Chung et al. (Oct. 24-28, 2015) "23rd United European Gastroenterology Week".
Coburn et al. (1981) "Potential Salicylamide Antiplaque Agents: In Vitro Antibacterial Activity against Actinomyces viscosus", Journal of Medicinal Chemistry, 24:1245-1249.
Cooper et al. (Sep. 7, 1998) "Systematic Review of Propionibacterium Acnes Resistance to Systemic Antibiotics", Medical Journal of Australia, 169(5):259-261.
Correa Pelayo (Jun. 2013) "Gastric Cancer: Overview", Gastroenterology Clinics of North America, 42(2):211-217 (8 pages).
Daidone et al. (Jun. 1990) "Salicylanilide and Its Heterocyclic Analogues. A Comparative Study of Their Antimicrobial Activity", Pharmazie, 45(6):441-442.
Damjanov Ivan (May 2005) "Robbins and Cotran Pathologic Basis of Disease, 7th Edition", Shock, 23(5):482-483.
Deen et al. (May 2013) "The Impact of Autophagic Processes on the Intracellular Fate of Helicobacter pylori", Autophagy, 9(5):639-652.
Dobie et al. (2004) "Fusidic Acid Resistance in *Staphylococcus aureus*", Archives of Disease in Childhood, 89:74-77.
Drago et al. (2005) "In Vitro Selection of Resistance in Pseudomonas Aeruginosa and *Acinetobacter* Spp. by Levofloxacin and Ciprofloxacin Alone and in Combination with Betalactams and Amikacin", The Journal of Antimicrobial Chemotherapy, 56(2):353-359.
Dubois et al. (2007) "Helicobacter pylori is Invasive and it may be a Facultative Intracellular Organism", Cellular Microbiology, 9(5):1108-1116.
Eom et al. (Feb. 22, 2011) "Use of Acid-suppressive Drugs and Risk of Pneumonia: A Systematic Review and Meta-analysis", CMAJ, 183(3):310-319.
Fifer, et al. (Jun. 2016) "Failure of Dual Antimicrobial Therapy in Treatment of Gonorrhea", New England Journal of Medicine 374(25):2504-2506.
Fischer et al. (2006) "Recipe Against Bath Dermatitis", Pharmacy, 3 pages.
Galmiche et al. (Nov./Dec. 2010) "Targeting of Helicobacter pylori VacA to Mitochondria", Gut Microbes, 1(6):392-395.
Ghazi et al. (1986) "Antibacterial Effect and Toxicity of Synthesized Salicylanilide Derivatives", Zentralblatt fur Mikrobiologie, 141(3):225-232.
Giannouli et al. (2014) "Use of Larvae of the Wax Moth Galleria Mellonella as an in Vivo Model to Study the Virulence of Helicobacter Pylori", BMC Microbiology, 14(228):1-10.
Gisbert et al. (2015) "Helicobacter pylori Second-line Rescue Therapy with Levofloxacin-and Bismuth-containing Quadruple Therapy, after Failure of Standard Triple or Nonbismuth Quadruple Treatments", Alimentary Pharmacology & Therapeutics, 41(8):768-775.
Gooyit et al. (Sep. 16, 2016) "Reprofiled Anthelmintics Abate Hypervirulent Stationary-Phase Clostridiumdifficile", Scientific Reports, 6(33642):8 pages.
Graham et al. (2010) "Helicobacter pylori Treatment in the Era of Increasing Antibiotic Resistance", Gut, 59(8):1143-1153.
Graham David Y. (2015) "Helicobacter pylori Update: Gastric Cancer, Reliable Therapy, and Possible Benefits", Gastroenterology, 148(4):719-731.
Gu Hy (2008) "The Study on the Mechanisms of Helicobacter pylori Motility in Gastric Mucosal Colonization", Chinese Journal of Laboratory Medicine, 31:733-736.
Guruge et al. (Mar. 31, 1998) "Epithelial Attachment Alters the Outcome of Helicobacter pylori Infection", Proceedings of the National Academy of Sciences, 95(7):3925-3930.
Hagymási et al. (Jun. 7, 2014) "Helicobacter Pylori Infection: New Pathogenetic and Clinical Aspects", World Journal of Gastroenterology, 20(21):6386-6399.
Hamdoun et al. (Mar. 2017) "Drug Repurposing of the Anthelmintic Niclosamide to Treat Multidrug-Resistant Leukemia", Frontiers in Pharmacology, 8(110):1-11.
Hamilton et al. (2018) "Repurposing of Anthelminthics as Anticancer Drugs", Oncomedicine, 3:1-8.
Hassan et el. (1991) "Topical Niclosamide as a Protective Agent Against Schistosome Infection", Journal of the Egyptian Society of Parasitology, 21(3):817-822.
Hassanzadeh et al. (2008) "Bacterial Resistance to Antibiotics in Acne Vulgaris: an in Vitro Study", Indian Journal of Dermatology, 53:122-124.
Hessey et al. (1990) "Bacterial Adhesion and Disease Activity in Helicobacter Associated Chronic Gastritis", Gut, 31:134-138.
Higaki et al. (Sep. 2, 1977) "Susceptibility of Propionibacterium acnes, *Staphylococcus aureus* and *Staphylococcus epidertnidis* to Kampo Formulations", The Journal of International Medical Research, XP055266294, 318-324.
Hlasta et al. (Jul. 21, 1998) "Novel Inhibitors of Bacterial Two-Component Systems with Gram Positive Antibacterial Activity: Pharmacophore Identification Based on the Screening Hit Closantel", Bioorganic & Medicinal Chemistry Letters, 8(14):1923-1928.
Huemer et al. (2018) "Impact of Antibiotic Treatment on Immune-checkpoint Blockade Efficacy in Advanced Non-squamous Non-small Cell Lung Cancer", Oncotarget, 9(23):16512-16520.
Imhann et al. (2016) "Proton Pump Inhibitors Affect the Gut Microbiome", Gut, 65(5):740-748.
Imperi et al. (2013) "New Life for an old drug: Antimicrobial, Agents and Chemotherapy", 557(2):996-1005.
Imramovsky et al., (2009) "Salicylanilide esters of N-protected amino acids as novel antimicrobial agents", Bioorganic and Medicinal Chemistry Letters, 19(2):348-351.
Jakobsson et al. (Mar. 2010,) "Short-Term Antibiotic Treatment Has Differing Long-Term Impacts on the Human Throat and Gut Microbiome", PLoS One, 5(3):1-12.
Kao et al. (Aug. 20, 2018) "The Antiparasitic Drug Niclosamide Inhibits Dengue Virus Infection by Interfering with Endosomal Acidification Independent of mTOR", PLoS One, 12(8):16 pages.

(56) References Cited

OTHER PUBLICATIONS

Kato et al. (2002) "Antibiotic Resistance of Helicobacter pylori Strains in Japanese Children", Journal of Clinical Microbiology, 40(2):649-653.
Kita et al. (2001) "CYP2C19 Genotype Related Effect of Omeprazole on Intragastric pH and Antimicrobial Stability", Pharmaceutical Research, 18(5):615-621.
Kratky et al. (Dec. 2010) "New Amino Acid Esters of Salicylanilides Active Against MDR-TB and Other Microbes", European Journal of Medicinal Chemistry, 45(12):6106-6113.
Kratky et al. (2011) "Salicylanilide Ester Prodrugs as Potential Antimicrobial Agents—a Review", Current Pharmaceutical Design, 17:3494-3505.
Kuipers et al. (Apr. 18, 1996) "Atrophic Gastritis and Helicobacter pylori Infection in Patients with Reflux Esophagitis Treated with Omeprazole or Fundoplication", The New England Journal of Medicine, 334(16):1018-1122.
Kuipers Ernst J. (2006) "Proton Pump Inhibitors and Helicobacter pylori Gastritis Friends or Foes?", Basic & Clinical Pharmacology & Toxicology, 99(3):187-194.
Lau et al. (Jul. 2001) "Provision of Phenotype-Matched Blood Units: no Need for Pre-Transfusion Antibody Screening", Haematologica, 86(7):742-748.
Lee et al. (2014) "Helicobacter pylori CagA Promotes Snail-mediated Epithelial-mesenchymal Transition by Reducing GSK-3 Activity", Nature Communications, 5(4423):1-13.
Devine et al., (Jan. 1, 1970) "Spectra of Susceptibility of Neisseria meningitidis to Antimicrobial Agents In vitro", pp. 329-334.
Lundberg et al. (Sep. 2013) "Efficacy of Topical and Systemic Antibiotic Treatment of Meticillin-Resistant *Staphylococcus aureus* in a Murine Superficial Skin Wound Infection Model", IInternational Journal of Antimicrobial Agents, 42(3):272-275.
MacIelag et al. (Jul. 30, 1998) "Substituted Salicylanilides as Inhibitors of Two-component Regulatory Systems in Bacteria", Journal of Medicinal Chemistry, 41(16):2939-2945.
Malfertheiner et al. (2012) "Management of Helicobacter pylori infectiondthe Maastricht IV/ Florence Consensus Report", Gut, 61:646-664.
Matos et al. (2013) "Helicobacter pylori CagA and VacA Genotypes and Gastric Phenotype: A Meta-analysis", European Journal of Gastroenterology & Hepatology, 25(12):1431-1441.
Matyk et al. (2005) "Heterocyclic Isosters of Antimycobacterial Salicylanilides", 60:399-408.
McGuckin et al. (Oct. 2007) "Muc1 Mucin Limits Both Helicobacter pylori Colonization of the Murine Gastric Mucosa and Associated Gastritis", Gastroenterology, 133(4):1210-1218.
Mohammad et al. (2018) "Repurposing Niclosamide for Intestinal Decolonization of Vancomycin-resistant Enterococci", International Journal of Antimicrobial Agents, 51(6):897-904.
Mollaghan et al. (2012) "Antistaphylococcal Activity of Novel Salicylanilide Derivatives", Current Drug Discovery Technologies, 9(1):39-47.
Mook et al. (2017) "Benzimidazole Inhibitors from the Niclosamide Chemotype Inhib Wnt/ß catenin Signaling with Selectivity over Effects on ATP Homeostasis", Bioorganic & Medicinal Chemistry, 25:1804-1816.
Muir et al. (1982) "Degradation of Niclosamide (2',5-dichloro-4'-nitrosalicylanilide) in Sediment and Water Systems", Journal of Agricultural and Food Chemistry, 30(6):1028-1032.
Nemeth et al. (Feb. 2015) "Bacteriostatic Versus Bactericidal Antibiotics for Patients with Serious Bacterial Infections: Systematic Review and Meta-analysis", The Journal of Antimicrobial Chemotherapy, 70(2):382-395.
Nguyen et al. (Sep. 1999) "Host Determinants of Helicobacter Pylori Infection and its Clinical Outcome", Helicobacter pylori, 4(3):185-197.
Nomura et al. (Feb. 2002) "*Staphylococcus aureus* and atopic dermatitis", IRYO, 54(2):62-66.
Noto et al. (2016) "The Mongolian Gerbil: A Robust Model of Helicobacter pylori-Induced Gastric Inflammation and Cancer", Methods in Molecular Biology, 1422:263-280 (20 pages).
Odenbreit Stefan (2005) "Adherence Properties of Helicobacter pylori: Impact on Pathogenesis and Adaptation to the Host", International Journal of Medical Microbiology, 295(5):317-324.
Osmundsen (1969) "Contact Photoallergy to Tribromsalicylanilide", British Journal of Dermatology, 81:429-434.
Ottemann et al. (Apr. 2002) "Helicobacter pylori Uses Motility for Initial Colonization and to Attain Robust Infection", Infection and Immunity, 70(4):1984-1990.
Papastergiou et al. (Jan. 14, 2016) "Helicobacter pylori and Colorectal Neoplasia: Is there a Causal Link?", World Journal of Gastroenterology, 22(2):649-658.
Papastergiou et al. (Aug. 7, 2014) "Treatment of Helicobacter pylori Infection: Meeting the Challenge of Antimicrobial Resistance", World Journal of Gastroenterology, 20(29):9898-9911.
Pauk et al. (2013) "New Derivatives of Salicylamides: Preparation and Antimicrobial Activity Against Various Bacterial Species", Bioorganic & Medicinal Chemistry, 21:6574-6581.
Peek Jr. et al. (Jan. 2002) "Helicobacter pylori and Gastrointestinal Tract Adenocarcinomas", Nature Reviews Cancer, 2(1):28-37.
Pereira et al. (Jan. 21, 2014) "Role of Helicobacter pylori in Gastric Mucosa-associated Lymphoid Tissue Lymphomas", World Journal of Gastroenterology, 20(3):684-698.
Pospisil (Feb. 1971) "Isovitalex—a chemically definable enricher of culture media for Neisseria gonorrhoeae", Ceskoslovenská Dermatol, 46(1):23-25.
Rajamuthiah et al. (2015) "Repurposing Salicylanilide Anthelmintic Drugs to Combat Drug Resistant *Staphylococcus aureus*", PLoS ONE, e0124595, 10(4):19 pages.
Rajamuthiah et al. (Feb. 2014) "Whole Animal Automated Platform for Drug Discovery against Multi-Drug Resistant *Staphylococcus aureus*", PloS One, 9(2):11 pages.
Rodriguez-Cavallini et al. (2004) "Etiologia Bacteriana y Susceptibilidad a Antibioticos en Pacientes con Acne", Rev Biomed, 15:101-106.
Rolfe (1990) "Chemical Resistence in livesteock—an overview", www.regional.org.au/au/roc/1990/roc199029.htm, 18 pages.
Romano et al. (2004) "Eradication of Helicobacter pylori: A Clinical Update", MedGenMed : Medscape general medicine, 6(1):19.
Sanphui et al. (Jul. 24, 2012) "Pharmaceutical Cocrystals of Niclosamide", Crystal Growth & Design, 12(9):4588-4599.
Schenk et al. (2000) "Effect of Helicobacter pylori Eradication on Chronic Gastritis During Omeprazole Therapy", Gut, 46:615-621.
Sekirov et al. (Oct. 2008) "Antibiotic-induced Perturbations of the Intestinal Microbiota Alter Host Susceptibility to Enteric Infection", Infection and Immunity, 76(10):4726-4736.
Shah et al. (May 2003) "High Levels of Fusidic Acid-Resistant *Staphylococcus aureus* in Dermatology Patients", British Journal of Dermatology, 148(5):1018-1020.
Sherwood et al. (2002) "Impact of Acid Secretion, Gastritis, and Mucus Thickness on Gastric Transfer of Antibiotics in Rats", Gut, 51(4):490-495.
Shimada et al. (Oct. 2007) "Role of Helicobacter Pylori Eradication in the Prevention of Peptic Ulcer in NSAID Users", Nihon Rinsho, 65(10):1824-1829.
Shiota et al. (Sep. 2015) "Antibiotic Resistance of Helicobacter pylori Among Male United States Veterans", Clinical Gastroenterology and Hepatology, 13(9):1616-1624 (17 pages).
Singh et al. (1977) "Synthesis of 5-chloro-3'-nitro-4'-substituted Salicylanilides, a New Series of Antihelmintic and Antimicrobial Agents", Journal of Medicinal Chemistry, 20(6):826-829.
Steffen et al. (Jun. 21, 2011) "Discovery and Structure-Activity Relationships of Modified Salicylanilides as Cell Permeable Inhibitors of Poly(ADP-ribose) Glycohydrolase (PARG)", Journal of Medicinal Chemistry, 54:5403-5413.
Stiefel et al. (Nov. 2006) "Suppression of Gastric Acid Production by Proton Pump Inhibitor Treatment Facilitates Colonization of the Large Intestine by Vancomycin-Resistant *Enterococcus* spp. and Klebsiella pneumoniae in Clindamycin-Treated Mice v", Antimicrob Agents Chemother, 50(11): 3905-3907.

(56) References Cited

OTHER PUBLICATIONS

Swan (1999) "The Pharmacology of Halogenated Salicylanilides and Their Anthelmintic Use in Animals", Journal of the South African Veterinary Association, 70(2):61-70.
Taborsky et al. (Sep. 1959) "Substituted Salicylanilides With Antimicrobial Acitvity", Journal of the American Pharmacists Association, XLVIII(9):503-507.
Takagi et al. (2018) "The Influence of Long-term Use of Proton Pump Inhibitors on the Gut Microbiota: An Age-sex-matched Case-control Study", Journal of Clinical Biochemistry and Nutrition, 62(1):100-105.
Tam et al. (Dec. 7, 2018) "Host-targeted Niclosamide Inhibits C. Difficile Virulence and Prevents Disease in Mice Without Disrupting the Gut Microbiota", Nature Communications, 9(5233):11 pages.
Tharmalingam et al. (Feb. 27, 2018) "Repurposing the Anthelmintic Drug Niclosamide to Combat Helicobacter Pylori", Scientific Reports, Article No. 3701, 8(1):12 pages.
Thompson et al. (Nov. 1, 2017) "P1.07-008 Microbiome & Immunotherapy: Antibiotic Use Is Associated with Inferior Survival for Lung Cancer Patients Receiving PD-1 Inhibitors", Journal of Thoracic Oncology, Abstract Only, 12(11S2):S1998.
Thung et al. (Feb. 2016) "Review Article: the Global Emergence of Helicobacter Pylori Antibiotic Resistance", Alimentary Pharmacology & Therapeutics, 43(4):514-533.
Uemura et al. (Aug. 1997) "Effect of Helicobacter Pylori Eradication on Subsequent Development of Cancer After Endoscopic Resection of Early Gastric Cancer", Cancer Epidemiol Biomarkers Prev, 6(8):639-642.
Van Tonder et al. (2004) "Preparation and Physicochemical Properties of Niclosamide Anhydrate and two Monohydrates", International Journal of Pharmaceutics, 269(2):417-432.
Vinsova et al. (2007) "Salicylanilide Acetates: Synthesis and Antibacterial Evaluation", Molecules, 12(1):1-12.
Vinsova et al. (2014) "Salicylanilide Diethyl Phosphates: Synthesis, Antimicrobial Activity and Cytotoxicity", Bioorganic & Medicinal Chemistry, 22:728-737.
Vinsova et al. (2004) "Salicylanilides: Still a Potential Antibacterially Active Group", Ceska Slov Farm, 53(6):294-299.
Waisser et al. (2003) "Antimycobacterial and Antifungal Isosterd of Salicylanilides", Arch Pharm (Weinheim), 336:322-335.
Waisser et al. (2001) "Synthesis and Antimycobacterial Activity of Salicylanilides Substituted in Position 5", Chemical Papers, 55(2)121-129.
Waisser et al. (2006) "The Oriented Development of Antituberculotics: Salicylanilides", Arch Pharm (Weinheim), 339:616-620.
Wu et al. (2014) "Antihelminthic Niclosamide Modulates Dendritic Cells Activation and Function", Cellular Immunology, 288:15-23.
Wu et al. (Jan. 2013) "Diagnostic Accuracy of Narrow-band Imaging for the Differentiation of Neoplastic from Non-neoplastic Colorectal Polyps: a Meta-analysis", Colorectal Disease, 15(1):3-11.
Wulff et al. (Jun. 2007) "Cream Formulations Protecting Against Cercarial Dermatitis by Trichobilharzia", Parasitology Research, 101(1):91-97.
Yamaoka et al. (1997) "Induction of Various Cytokines and Development of Severe Mucosal Inflammation by cagA Gene Positive Helicobacter Pylori Strains", Gut, 41(4):442-451.
Yu et al. (2018) "Niclosamide Exhibits Potent Anticancer Activity and Synergizes with Sorafenib in Human Renal Cell Cancer Cells", Cellular Physiology and Biochemistry, 47(3):957-971.
Yutin et al. (Oct. 2013) "A Genomic Update on Clostridial Phylogeny: Gram-negativespore-formers and Other Misplaced Clostridia,", Environ Microbial, 15(10): 2631-2641.
Unemo Magnus (2015) "Current and Future Antimicrobial Treatment of Gonorrhoea—The Rapidly Evolving Neisseria Gonorrhoeae Continues to Challenge", BMC Infectious Diseases, 15(364):15 pages.
Zhao et al. (Oct. 2012) "Study on in vitro antimicrobial activity of closantel to *Staphylococcus aureus*", Abstract only, Chinese Journal of Nosocomiology, 22(10):01 page.
Jabs et al. (Oct. 2000) "Guidelines for the Use of Immunosuppressive Drugs in Patients with Ocular Inflammatory Disorders: Recommendations of an Expert Panel", American Journal of Ophthalmology, 130(4): 492-513.
Ofori-Adjei et al. (Jan. 2008) "A Review of the Safety of Niclosamide, Pyrantel, Triclabendazole and Oxamniquine", The International Journal of Risk & Safety in Medicine, 20(3):113-122.
Pearson et al. (Apr. 1985) "Niclosamide Therapy for Tapeworm Infections", Annals of Internal Medicine, 102(4):550-551.
Devine et al. (Feb. 1970) "Spectra of Susceptibility of *Neisseria meningitidis* to Antimicrobial Agents In Vitro", Journal of Applied Microbiology, 19(2):329-334.
Huang, et al., "New Continuous Fluorometric Assay for Bacterial Transglycosylase Using Förster Resonance Energy Transfer," *Journal of the American Chemical Society*, 2013, 135, 17078-17089, 12 pages.

* cited by examiner

Fig. 5A
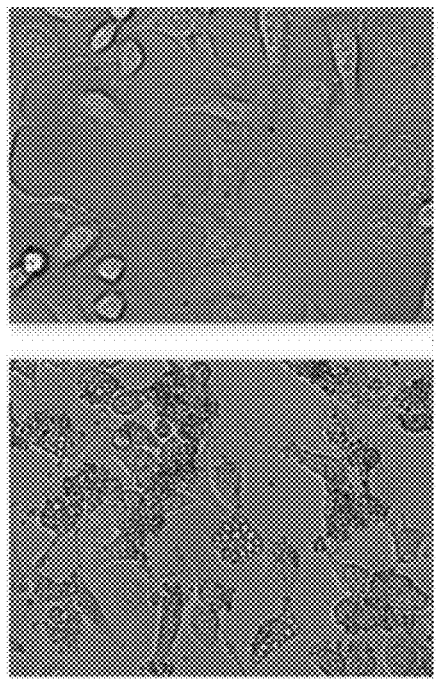
Fig. 5B
Fig. 5C
Fig. 5D
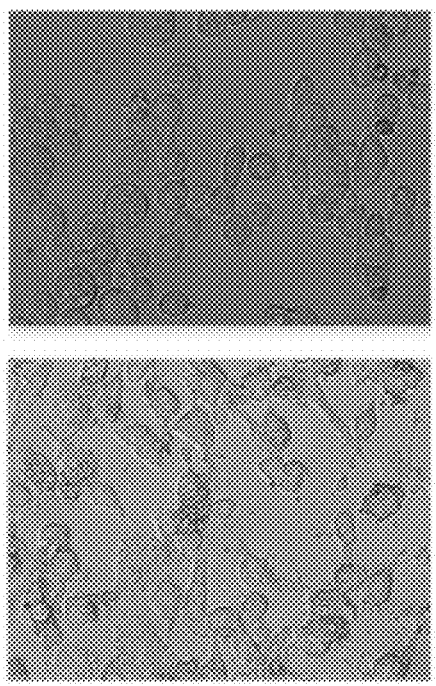
Fig. 5E
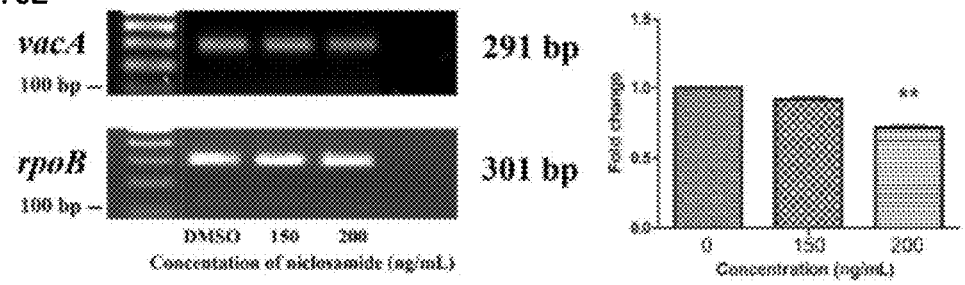

METHODS FOR TREATING DISEASES OR INFECTIONS CAUSED BY OR ASSOCIATED WITH *H. PYLORI* USING A HALOGENATED SALICYLANILIDE

CROSS-REFERENCES TO RELATED APPLICATIONS

This application claims priority to U.S. Provisional Application No. 62/809,864, filed on Feb. 25, 2019, which is incorporated herein by reference in its entirety.

STATEMENT OF FEDERALLY SPONSORED RESEARCH

This invention was made with government support under grant number P01 A1083214 awarded by the National Institutes of Health. The government has certain rights in the invention.

INCORPORATION OF THE SEQUENCE LISTING is application contains a Sequence Listing, which is hereby incorporated herein by reference in its entirety. The accompanying Sequence Listing text file, named "052211-516001US_SL_ST25.txt," was created on Apr. 25, 2019 and is 69 KB.

FIELD OF THE INVENTION

This disclosure relates to halogenated salicylanilides, for example niclosamide, oxyclozanide, closantel or rafoxanide, or pharmaceutically acceptable salts or solvates thereof, for use in the treatment or prevention of an infection or disease caused by or associated with *Helicobacter* Spp., particularly *H. pylori*.

BACKGROUND

*Helicobacter pylori* is a Gram-negative, helically shaped, stomach pathogen associated with human gastric mucosa. This *bacillus* is associated with the development of gastro-intestinal disorders, including chronic gastritis, peptic ulcer, gastric mucosa-associated lymphoid tissue (MALT) lymphoma and gastric carcinoma (Thung, I. et al. Alimentary pharmacology & therapeutics 43, 514-533 (2016)).

About 2.9% of *H. pylori* infected individuals develop gastric cancer and eradication of *H. pylori* infection decreased the risk of gastric cancer (Hagymasi, et al. World journal of gastroenterology: WJG 20, 6386 (2014); and Graham, Gastroenterology 148, 719-731. e713 (2015)). Meta-analysis by Wu et al. (Colorectal Disease 15 (2013)), has also shown that *H. pylori* infection may be associated with increased occurrence of colorectal cancer.

*H. pylori* infection is often initiated in childhood and it is estimated that *H. pylori* infection is present in about half of the global population (Nguyen et al. *Helicobacter* 4, 185-197 (1999)). The World Health Organization (WHO) has declared *H. pylori* a class I gastric carcinogen with worldwide prevalence (Peek et al. Nature reviews. Cancer 2, 28 (2002)).

Successful antimicrobial treatment for *H. pylori* infection is extremely challenging due to its survival in a hostile acidic environment and association within the gastric mucosa (Romano et al. Medscape General Medicine 6, 19 (2004)). To be effective against *H. pylori* antimicrobial agents must penetrate thick mucus of the gastric mucosa and remain active in the low pH of the gastric environment. Current antibiotic treatments require sequential administration of two or more antibiotics, typically clarithromycin together with amoxicillin or metronidazole (Papastergiou et al. J. Gastroenterol. 2014, Aug. 7; 20(29):9898-911). However, many of the antibiotics used in current treatments are degraded and/or lose effectiveness at low pH. To counter the negative effects of low pH on the antibiotics, current treatments combine the antibiotics with a proton pump inhibitor (PPI) to increase the gastric pH (Kita et al. CYP2C19 genotype related effect of omeprazole on intragastric pH and antimicrobial stability. Pharm. Res. 2001; 18:615-621). Raising gastric pH with a PPI also acts to increase the population of dividing *H. pylori* making the bacteria more susceptible to antibiotics such as amoxicillin and clarithromycin (Graham et al. Gut 59, 1143-1153 (2010)).

Unfortunately triple therapy treatment regimens comprising a PPI and two antibiotics, especially those based on clarithromycin, are increasingly failing to eradicate *H. pylori* infection, primarily due to the emergence of *H. pylori* resistance to the antibiotics used in these therapies. For example, *H. pylori* resistance to clarithromycin among male U.S. veterans increased from 16% to 24% during 2009 to 2013 (Shiota et al. Clinical Gastroenterology and Hepatology 13, 1616-1624 (2015)). As a result, clarithromycin-based triple therapies are generally no longer considered suitable for the treatment of *H. pylori* (Graham et al. (2010) supra)

Quadruple treatment regimens using bismuth have been developed to combat *H. pylori* resistance. These typically comprising bismuth subcitrate, a PPI, and two antibiotics (e.g. metronidazole and a tetracycline; levofloxacin and a tetracycline; a nitroimidazole and tetracycline; amoxicillin and furazolidone; or metronidazole and furazolidone) have been shown to be beneficial compared to triple therapies, especially in *H. pylori* which is resistant to e.g. metronidazole or clarithromycin (Gisbert et al. *Helicobacter pylori* second-line rescue therapy with levofloxacin- and bismuth-containing quadruple therapy, after failure of standard triple or non-bismuth quadruple treatments. Aliment Pharmacol. Ther. 2015; 41:768-775).

Sequential, concomitant and hybrid dosage regimens have also been developed, comprising a PPI, various antibiotic agents and/or probiotics. However, these have failed to eliminate the emergence of *H. pylori* resistance (ACG Clinical Guidelines for the treatment of *Helicobacter pylori* infection Am J Gastroenterol 2017; 112:212-238).

Current treatment regimens for *H. pylori* are becoming increasingly complex and patient compliance with the treatment is likely to be poor. Furthermore, the use of multiple antibiotics can cause significant damage to the gut microbiome. This can lead to antibiotic-induced gut dysbiosis and an increased risk of intestine-related diseases, such as IBD, infectious diseases, and immunity-related disorders, e.g. allergic or atopic skin diseases and type 1 diabetes (Sekirov et al. Infect Immun. 2008 October; 76(10):4726-36). Studies on the effects of clarithromycin, metronidazole, and omeprazole on the composition of the pharyngeal and faecal bacterial taxa show that these antibiotics may affect 30% or more of the microbiota composition, and although the microbiota may partially recover, the effects can persist for at least 4 years after exposure (Jakobsson et al., PLoS One. 2010 Mar. 24; 5(3)).

PPIs raise gastric pH, which is beneficial for the healing of, for example, gastric ulcers. The higher gastric pH resulting from PPI use also acts retain the efficacy of the antibiotics used in current treatments of *H. pylori* infections, many of which are prone to degradation and/or loss of efficacy at low pH. However, increasing gastric pH can result in undesirable dysbiosis in the gut microbiome and may increase the risk of community-acquired pneumonia and *Clostridium difficile*-associated diarrhoea in long-term PPI users compared with non-PPI users (Eom et al. CMAJ. 2011 Feb. 22; 183(3):310-9). PPI use may also be associated with colonization of the lower GI-tract with vancomycin-resistant *Enterococcus* spp. and *Klebsiella pneumoniae* (Stiefel et al. Antimicrob Agents Chemother. 2006 November; 50(11): 3905-3907).

There remains a need for an effective treatment of *H. pylori* infections and associated disease which do not have one or more of the drawbacks of current antibiotic therapies, such as triple and quadruple treatment regimens.

Halogenated salicylanilides such as oxyclozanide, niclosamide, closantel and rafoxanide are important anthelmintics used to treat cestodes (tapeworms) such as *Taenia saginata* (beef tapeworm), *Taenia solium* (pork tapeworm), *Hymenolepsis nana* (dwarf tapeworm), *Hymenolepsis* (rat tape worm), *Diphyllobothrium latum* (broad or fish tapeworm), and *Dipylidium caninum* (dog and cat tapeworm). Niclosamide is also widely used as an anthelmintic against tapeworms and rumen flukes in companion animals and livestock, for example the treatment of *Haemonchus* spp. and *Fasciola* spp. infestation in sheep and cattle, *Oestrus ovis* in sheep and *Anaplocephala* spp. in horses, and the treatment *Paramphistomum* spp. (intestinal flukes) in cattle, sheep and goats.

Niclosamide is commercially available in a number of formulations including, but not limited to Bayer73®, Bayer2353®, Bayer25648®, Bayluscid®, Baylucide®, Cestocid®, Clonitralid, Dichlosale®, Fenasal®, HL 24470, Lomesan®, Lomezan®, Manosil®, Nasemo®, Niclosamide, Phenasal®, Tredemine®, Sulqui®, Vermitid®, Vermitin® and Yomesan®.

Niclosamide has been proposed as a possible systemic treatment for chronic lung infections caused by the proteobacterium *Pseudomonas aeruginosa* and the actinobacterium *Mycoplasmum tuberculosis* (F. Imperi et al., Antimicrobial, Agents and Chemotherapy, 557(2), 996-1005 (2013)).

J. Vinsova et al. (Molecules, vol. 12, no. 1, pp. 1-12, 2007; *Bioorganic and Medicinal Chemistry Letters*, vol. 19, no. 2, pp. 348-351, 2009; *European Journal of Medicinal Chemistry*, vol. 45, no. 12, pp. 6106-6113, 2010) disclose that certain salicylanilides have antibacterial activity. *H. pylori* is not disclosed.

Ghazi et al. (Zentralbl. Mikrobiol. 141 (1986), 225-232) have tested the antibacterial effect and toxicity of synthesized salicylanilide derivatives against *Escherichia coli, Bacillus subtilis, Pseudomonas aeruginosa* and *Staphylococcus aureus*.

R. Rajamuthiah et al. (PloS One, 2014, 9(2): e89189) identified closantel as a hit in a high throughput liquid screening assay and found anti-staphylococcal activity of closantel against vancomycin-resistant *S. aureus* isolates and other Gram-positive bacteria.

R. Rajamuthiah et al. (PloS One, 2015, 10(4):e0124595) describe that niclosamide and oxyclozanide have activity against MRSA.

Pauk et al. Bioorg. & Med. Chem. 23, 6574-6581 (2013), discloses the in-vitro anti-microbial activity of certain halogenated salicylanilides and derivatives.

Chung et al. 23$^{rd}$ United European Gastroenterology Week, Oct. 24-28, 2015 discloses the results of a high throughput screen in an in-vitro antimicrobial assay against *H. pylori*. The study identified 84 compounds that were active, one of which was niclosamide. The antimicrobial activity was assessed by culturing the *H. pylori* in a medium containing *brucella* agar and 7% defibrinated sheep blood, which is believed to have an approximately neutral pH. Chung et al. selected diphenyleneiodonium chloride (DPI) and parthenolide (PTL) as the most promising compounds for further development. No in-vivo data is disclosed.

Ahn et al Oncotarget, 2017, Vol. 8, (No. 19), pp. 31856-31863 discloses that niclosamide attenuates Ras-induced oncogenesis by binding to and activating GSK-3.

WO 2008/155535 describes the use of halogenated salicylanilides for the treatment of acne resulting from Propioni bacterial infection.

WO 2016/038035 relates to the use of closantel, rafoxanide, oxyclozanide, niclosamide and derivatives thereof in the topical treatment or prevention of infections caused by Gram-positive bacteria, such as *Staphylococcus* and *Streptococcus*.

WO 2016/193136 relates to the use of halogenated salicylanilides in the treatment of an infection caused by *Clostridium* bacteria, in particular *Clostridium difficile*.

WO 2017/200396 discloses the concurrent use of certain salicylamides, such as nitazoxanide, niclosamide or oxyclozanide, and an agent that increases the permeability of a bacterial cell membrane for treatment of an infection or for reducing or eliminating formation of a bacterial biofilm caused by Gram negative bacteria. Agents disclosed in WO 2017/200396 to increase the permeability of the bacterial cell membrane are polymyxin B, polymyxin E (colistin) and gramicidin. Polymyxins B and E are antibiotics used in the treatment of Gram-negative bacterial infections. Gramicidin is a heterogeneous mixture of three antibiotic compounds, gramicidins A, B and C, which are collectively called gramicidin D.

WO 2016/080846 discloses the treatment of certain Gram negative bacterial infections by concurrent administration of certain salicylamide compounds, such as nitazoxanide or niclosamide, and an efflux pump inhibitor. Examples of efflux pump inhibitors disclosed in WO 2016/080846 include those described in U.S. Pat. No. 6,399,629, alkoxyquinoline derivatives, e.g. 2,8-dimethyl-4-(2'-pyrrolidino-ethyl)-oxyquinoline; piperidine and piperidine analogues; phenothiazines (e.g. chloropromazine); monoterpene derivatives (e.g. geranylamine); or arginine derivatives, for example those described in U.S. Pat. No. 6,251,869. Preferred efflux inhibitors are stated to be phenylalanine-arginine β-napthylamide and 2,3-dibromomaleimide. WO 2016/080846 does not disclose *H. pylori*.

WO2018/141063 described the use of a bicarbonate, such as sodium bicarbonate, to potentiate the effects of an antimicrobial agent.

BRIEF SUMMARY OF THE DISCLOSURE

The inventors have found that halogenated salicylanilides, for example niclosamide, oxyclozanide, rafoxanide and closantel, are active against *H. pylori*, and that the antimicrobial activity is retained at low pH representative of that present in the gastric acid. As such a halogenated salicylanilide may be suitable for use as an oral therapy for the treatment or prevention of an infection or disease caused by or associated with *H. pylori*.

According to a first aspect, there is provided a method for the prevention or treatment of a disease or infection caused by or associated with *H. pylori* in a subject infected with *H.*

*pylori*, the method comprising orally administering to the subject an effective amount of a halogenated salicylanilide, or a pharmaceutically acceptable salt or solvate thereof.

According to another aspect there is provided a method for eradicating a *H. pylori* infection in a subject, the method comprising orally administering to the subject an effective amount of a halogenated salicylanilide, or a pharmaceutically acceptable salt or solvate thereof.

According to another aspect there is provided a method for eradicating a *H. pylori* infection in a subject with a disease or infection caused by or associated with *H. pylori*, the method comprising orally administering to the subject an effective amount of a halogenated salicylanilide, or a pharmaceutically acceptable salt or solvate thereof.

Proton pump inhibitors are usually administered concurrently with two or more antibiotics to treat *H. pylori* infections. The presence of the PPI raises the level of gastric pH and makes the *H. pylori* more susceptible to the antibiotics currently used treat the infection. The high gastric pH also acts to protect the activity and/or acid induced degradation of antibiotic compounds such as clarithromycin. However, the high gastric pH induced by PPI use can lead to dysbiosis and the undesirable colonisation of the lower GI-tract with pathogens such as *C. difficile*, vancomycin-resistant *Enterococcus* spp. and *Klebsiella pneumoniae* (Eom et al., Steifel et al. supra.).

Meta-analyses of clinical data has shown that PPI use is a potential risk for the development of enteric infections caused by *Clostridium difficile*, small intestinal bacterial overgrowth, spontaneous bacterial peritonitis, community-acquired pneumonia, hepatic encephalopathy, and adverse outcomes in inflammatory bowel disease. Changes in the composition and function of the gut microbiota with the use of PPIs was also observed resulting in increased presence of Streptococcaceae and Enterococcaceae (risk factors for *C. difficile* infection), and decreased population of *Faecalibacterium*, a commensal anti-inflammatory microorganism.

The applicant has found that halogenated salicylanilides (e.g. niclosamide) retain activity against *H. pylori* even at low pH. This provides the possibility of treating *H. pylori* infections without the need for concurrent use of a PPI to increase gastric pH.

Accordingly, it may be that the halogenated salicylanilide, or a pharmaceutically acceptable salt or solvate thereof is orally administered to the subject without concurrent treatment of the subject with a PPI. Such a therapy would eliminate any negative side-effects associated with PPI therapy, for example PPI induced gut dysbiosis, which can result in a higher risk of developing enteric infections such as *C. difficile* (Naito et al J. Clin. Biochem. Nutr. 2018, vol. 62(1), 100-105). Avoiding the requirement for a PPI also simplifies the treatment and will aid patient compliance with the treatment. The PPI excluded from the method may be any PPI, for example any PPI mentioned herein, for example benzimidazole or azabenzimidazole derivatives.

Current antibiotic treatment regimens for *H. pylori* infections (e.g. the triple and quadruple regimens discussed above) require the administration of a combination of two or more antibiotic agents. However, *H. pylori* resistance to such antibiotics is a growing problem, particularly resistance to clarithromycin. Furthermore, oral administration of combinations of antibiotics can devastate the natural gut bacteria leading to dysbiosis and associated problems, including increased risk of enteric infections and inflammation of the lower GI tract. The Examples herein show that no *H. pylori* resistance to niclosamide developed in the 30 day resistance studies carried out. In contrast, amoxicillin and clarithromycin, two commonly used antibiotics for *H. pylori* treatment, showed evidence of resistance developing after 15 and 24 days respectively. The halogenated salicylanilide used in the present methods may therefore provide a treatment of a disease or infection caused by or associated with *H. pylori* which has a low risk of resistance to the halogenated salicylanilide developing. The use of a single agent (e.g. niclosamide) to eradicate the *H. pylori* infection will also minimise the impact of the treatment on gut bacteria, thereby preventing or reducing the risk of dysbiosis in the lower GI tract.

Accordingly, it may be that the subject is not treated concurrently with any other antibiotic. It may be that the halogenated salicylanilide, or a pharmaceutically acceptable salt or solvate thereof, is orally administered to the subject, wherein the subject is not treated concurrently with any antibiotic than the halogenated salicylanilide. It may be that the subject is not treated concurrently with another antibiotic that is active against Gram negative bacteria. It may be that the subject is not treated concurrently with another antibiotic that is active against *H. pylori*. For example, the subject is not concurrently treated with an antibiotic selected from: clarithromycin, amoxicillin, tetracycline, doxycycline, a nitroimidazole (e.g. metronidazole), fluoroquinolone, moxifloxacin, rifabutin, levofloxacin and ciprofloxacin. It may be that the subject is not concurrently treated with an antibiotic selected from: clarithromycin, amoxicillin and metronidazole. It may be that the subject is not concurrently treated with clarithromycin.

It may be that the halogenated salicylanilide, or a pharmaceutically acceptable salt or solvate thereof is orally administered to the subject as a monotherapy for the treatment or prevention of a disease or infection caused by or associated with *H. pylori*. It may be that the method is for the eradication of an *H. pylori* infection in a subject, the method comprising orally administering the halogenated salicylanilide to the subject as a monotherapy. It may be that the halogenated salicylanilide, or a pharmaceutically acceptable salt or solvate thereof is orally administered to the subject, wherein the subject is not treated concurrently with a PPI or another antibiotic. It may be that the subject is not treated concurrently with a PPI and an antibiotic selected from: clarithromycin, amoxicillin, tetracycline, doxycycline, a nitroimidazole (e.g. metronidazole), fluoroquinolone, moxifloxacin, rifabutin, levofloxacin and ciprofloxacin. It may be that the disease or infection caused by or associated with *H. pylori* is treated exclusively with the halogenated salicylanilide, or a pharmaceutically acceptable salt or solvate thereof.

As illustrated in the Examples herein, the inventors have found that niclosamide is at least partially synergistic against *H. pylori* when used in combination with a proton pump inhibitor such as omeprazole or pantoprazole. Concurrent treatment of a subject with a halogenated salicylanilide and a PPI may therefore be particularly effective for the treatment or prevention of a disease or infection caused by or associated with *H. pylori*.

Accordingly, also provided is a method for the prevention or treatment of a disease or infection caused by or associated with *H. pylori* in a subject infected by *H. pylori* and wherein the subject is being treated with a PPI, the method comprising orally administering to the subject an effective amount of a halogenated salicylanilide, or a pharmaceutically acceptable salt or solvate thereof.

Also provided is a method for the eradication of a *H. pylori* infection in a subject that is being treated with a PPI, the method comprising orally administering to the subject a halogenated salicylanilide, or a pharmaceutically acceptable salt or solvate thereof.

Also provided is a method for the prevention or treatment of a disease or infection caused by or associated with *H. pylori* in a subject infected with *H. pylori*, the method comprising orally administering to the subject an effective amount of a halogenated salicylanilide, or a pharmaceutically acceptable salt or solvate thereof, concurrently with an effective amount of a proton pump inhibitor.

Also provided is a method for the eradication of a *H. pylori* infection in a subject, the method comprising orally administering to the subject an effective amount of a halogenated salicylanilide, or a pharmaceutically acceptable salt or solvate thereof, concurrently with an effective amount of a proton pump inhibitor.

Also provided is a method for the eradication of a *H. pylori* infection in a subject with a disease or infection caused by or associated with *H. pylori*, the method comprising orally administering to the subject an effective amount of a halogenated salicylanilide, or a pharmaceutically acceptable salt or solvate thereof, concurrently with an effective amount of a proton pump inhibitor.

The PPI may be any PPI, including any of the PPIs disclosed herein. It may be that the proton pump inhibitor is a benzimidazole or azabenzimidazole derivative, for example wherein the PPI is selected from: omeprazole, hydroxyomeprazole, esomeprazole, lansoprazole, dexlansoprazole, pantoprazole, rabeprazole, tenatoprazole, and leminoprazole, or a pharmaceutically acceptable salt, or solvate thereof.

It may be that the proton pump inhibitor is a benzimidazole derivative, for example wherein the PPI is selected from omeprazole, hydroxyomeprazole, esomeprazole, lansoprazole, dexlansoprazole, pantoprazole and rabeprazole, or a pharmaceutically acceptable salt, or solvate thereof. It may be that the proton pump inhibitor is selected from: omeprazole and pantoprazole, or a pharmaceutically acceptable salt, or solvate thereof. It may be that the proton pump inhibitor is omeprazole, or a pharmaceutically acceptable salt, or solvate thereof. It may be that the proton pump inhibitor is pantoprazole, or a pharmaceutically acceptable salt, or solvate thereof.

*H. pylori* infection induces inflammation in the gastric mucosa leading to the development of gastritis and other inflammatory driven conditions. Chronic use of PPI therapy in subjects that are infected with *H. pylori* is associated with the development of corpus-predominant gastritis, which in turn accelerates the development of atrophic gastritis (Schenk et al. Gut 2000; 46:615-621). Subjects infected with *H. pylori* that are treated chronically with a PPI are therefore at an increased risk of developing atrophic gastritis, a known precursor for gastric cancer ((Kuipers et al. N. Engl. J. Med. 1996; 334;

and Cheung, Gut and Liver, 11(5), 2017, 575-576).

Treatment of a subject infected by *H. pylori* concurrently with a halogenated salicylanilide, or a pharmaceutically acceptable salt or solvate thereof, and a proton pump inhibitor may prevent or reduce the risk of developing atrophic gastritis. Therefore, it may be that the method is for preventing or treating *H. pylori* induced atrophic gastritis in a subject infected with *H. pylori* that is being treated with a PPI, the method comprising orally administering to the subject a halogenated salicylanilide, or a pharmaceutically acceptable salt or solvate thereof. It may be that the method is for preventing or treating *H. pylori* induced atrophic gastritis in a subject infected with *H. pylori*, the method comprising orally administering to the subject a halogenated salicylanilide, or a pharmaceutically acceptable salt or solvate thereof concurrently with a PPI.

It may be that the method is for treating or preventing *H. pylori* induced gastritis (e.g. corpus gastritis) in a subject infected with *H. pylori* that is being treated with a PPI, the method comprising orally administering to the subject a halogenated salicylanilide, or a pharmaceutically acceptable salt or solvate thereof. It may be that the method is for treating or preventing *H. pylori* induced gastritis (e.g. corpus gastritis) in a subject infected with *H. pylori*, the method comprising orally administering to the subject a halogenated salicylanilide, or a pharmaceutically acceptable salt or solvate thereof concurrently with a PPI.

It may be that the method is for the treatment or prevention of *H. pylori* induced loss of gastric mucosal glandular tissue (glandular atrophy) in a subject infected by *H. pylori* that is being treated with a PPI, the method comprising orally administering to the subject a halogenated salicylanilide, or a pharmaceutically acceptable salt or solvate thereof. It may be that the method is for the treatment or prevention of *H. pylori* induced loss of gastric mucosal glandular tissue (glandular atrophy) in a subject infected by *H. pylori*, the method comprising orally administering to the subject a halogenated salicylanilide, or a pharmaceutically acceptable salt or solvate thereof concurrently with a PPI.

It may be that treatment of a subject infected by *H. pylori* concurrently with a halogenated salicylanilide, or a pharmaceutically acceptable salt or solvate thereof, and a proton pump inhibitor, may prevent or reduce the risk of developing gastric cancer.

Accordingly, it may be that the method is for preventing or reducing the risk of *H. pylori* induced gastric cancer in a subject infected with *H. pylori*, the method comprising orally administering to the subject an affective amount of a halogenated salicylanilide, or a pharmaceutically acceptable salt or solvate thereof concurrently with the administration of an effective amount of a proton pump inhibitor.

Eradication of *H. pylori* from a subject that is being treated with a PPI may therefore be beneficial to treat or prevent atrophic gastritis and/or to treat, prevent, or minimise the risk that the subject develops gastric cancer and/or to inhibit or prevent progression of gastric cancer (e.g. to inhibit progression of early gastric cancer). Accordingly, there is provided a method for eradicating *H. pylori* from a subject that is being treated with a PPI, the method comprising orally administering to the subject an effective amount of a halogenated salicylanilide, or a pharmaceutically acceptable salt or solvate thereof. It may be that the subject has been treated chronically with the PPI prior to administration of the halogenated salicylanilide, for example where the subject has been treated with the PPI for more than 1 month, more than 3 months, more than 6 months, more than 9 months or more than 1 year. However, in certain embodiments a subject infected with *H. pylori* is treated by oral administration of the halogenated salicylanilide to eradicate the *H. pylori* infection prior to initiating chronic PPI therapy. Eliminating the *H. pylori* infection prior to initiating PPI (especially chronic PPI) therapy is expected to reduce or eliminate the risk that *H. pylori* induced disease (e.g. atrophic gastritis or gastric cancer) that would otherwise be accelerated by the chronic use of a PPI in a subject infected by *H. pylori*.

Accordingly it may be that the method is for the eradication of a *H. pylori* infection in a subject that has not been previously treated with a PPI, the method comprising orally administering an effective amount of a halogenated salicylanilide, or a pharmaceutically acceptable salt or solvate thereof; and following eradication of the *H. pylori* infection, administering to the subject an effective amount of a proton pump inhibitor It may be that the method is for the prevention or treatment of a disease or infection caused by or associated with *H. pylori* in a subject infected by *H. pylori*, wherein the subject has not been previously treated with a PPI, the method comprising orally administering to the subject an effective amount of a halogenated salicylanilide, or a pharmaceutically acceptable salt or solvate thereof; and following eradication of the *H. pylori* infection, administering to the subject an effective amount of a proton pump inhibitor.

In the embodiments above relating to the concurrent use of the halogenated salicylanilide and a PPI, it may be that the subject is not treated with any other antibiotic agent other than the halogenated salicylanilide. For example the subject is not treated with another antibiotic that is active against Gram negative bacteria. It may be that the subject is not treated concurrently with another antibiotic that is active against *H. pylori*. For example, the subject is not concurrently treated with an antibiotic selected from: clarithromycin, amoxicillin, tetracycline, doxycycline, a nitroimidazole (e.g. metronidazole), fluoroquinolone, moxifloxacin, rifabutin, levofloxacin and ciprofloxacin. It may be that the subject is not concurrently treated with an antibiotic selected from: clarithromycin, amoxicillin and metronidazole. It may be that the subject is not concurrently treated with clarithromycin.

The Examples herein illustrate at least a partial synergy against *H. pylori* when niclosamide and metronidazole are used concurrently. Accordingly, also provided is a method for the prevention or treatment of a disease or infection caused by or associated with *H. pylori* in a subject that is being treated with a nitroimidazole antibiotic, the method comprising orally administering to the subject an effective amount of a halogenated salicylanilide, or a pharmaceutically acceptable salt or solvate thereof.

Also provided is a method for the prevention or treatment of a disease or infection caused by or associated with *H. pylori* in a subject infected with *H. pylori*, the method comprising orally administering to the subject an effective amount of a halogenated salicylanilide, or a pharmaceutically acceptable salt or solvate thereof, concurrently with an effective amount of a nitroimidazole antibiotic.

Also provided is a method for eradicating a *H. pylori* infection in a subject, the method comprising orally administering to the subject an effective amount of a halogenated salicylanilide, or a pharmaceutically acceptable salt or solvate thereof, concurrently with an effective amount of a nitroimidazole antibiotic.

Also provided is a method for eradicating a *H. pylori* infection in a subject with a disease or infection caused by or associated with *H. pylori*, the method comprising orally administering to the subject an effective amount of a halogenated salicylanilide, or a pharmaceutically acceptable salt or solvate thereof, concurrently with an effective amount of a nitroimidazole antibiotic.

It may be that the nitroimidazole antibiotic is a 5-nitroimdazole antibiotic. It may be that the nitroimidazole antibiotic is selected from the group consisting of: metronidazole, tinidazole, nimorazole, dimetridazole, pretomanid, ornidazole, megazol, and azanidazole, or a pharmaceutically acceptable salt thereof. It may be that the nitroimidazole antibiotic is metronidazole, or a pharmaceutically acceptable salt thereof.

It may be that the subject is treated concurrently with the halogenated salicylanilide, or a pharmaceutically acceptable salt or solvate thereof, the nitroimidazole antibiotic (e.g. metronidazole) and a PPI. In other embodiments the subject is not treated concurrently with a PPI.

It may be that the subject is not treated with any other antibiotic agents other than the halogenated salicylanilide and the nitroimidazole antibiotic.

It may be that the disease or infection caused by or associated with *H. pylori* in any of the methods of treatment disclosed herein is selected from: dyspepsia (e.g. functional dyspepsia), gastritis (e.g. chronic gastritis or atrophic gastritis), peptic ulcer disease (for example gastric ulcer, or peptic ulcer), premalignant gastric lesions (e.g. gastric epithelial dysplasia), gastric cancer (e.g. early gastric cancer) and gastric mucosa-associated lymphoid tissue (MALT) lymphoma.

It may be that the *H. pylori* infection is asymptomatic. For example, it may be that the method comprises eradicating an asymptomatic *H. pylori* infection in a subject infected by *H. pylori*, the method comprising orally administering to the subject an effective amount of the halogenated salicylanilide, or a pharmaceutically acceptable salt or solvate thereof.

For example it may be that the method comprises treating asymptomatic non-atrophic gastritis in a subject infected with *H. pylori*.

It may be that the disease or infection caused by or associated with *H. pylori* is gastritis, for example chronic gastritis. It may be that the disease or infection caused by or associated with *H. pylori* is corpus gastritis. It may be that the disease or infection caused by or associated with *H. pylori* is atrophic gastritis.

It may be that the disease or infection caused by or associated with *H. pylori* is peptic ulcer disease. It may be that the disease or infection caused by or associated with *H. pylori* is gastric ulcer. It may be that the disease or infection caused by or associated with *H. pylori* is peptic ulcer.

It may be that the disease or infection caused by or associated with *H. pylori* is a premalignant gastric lesion (e.g. gastric epithelial dysplasia).

It may be that the disease or infection caused by or associated with *H. pylori* is gastric cancer. It may be that the disease or infection caused by or associated with H. pylori is early gastric cancer.

In certain embodiments there is provided a method for the prevention of gastric cancer in a subject infected with *H. pylori*, the method comprising orally administering to the subject an effective amount of a halogenated salicylanilide, or a pharmaceutically acceptable salt or solvate thereof.

In certain embodiments there is provided a method for inhibiting the carcinogenesis of a premalignant gastric epithelial lesion in a subject infected with *H. pylori*, the method comprising orally administering to the subject an effective amount of a halogenated salicylanilide, or a pharmaceutically acceptable salt or solvate thereof.

In certain embodiments there is provided a method for treating a premalignant gastric epithelial lesion in a subject infected with *H. pylori*, the method comprising orally administering to the subject an effective amount of a halogenated salicylanilide, or a pharmaceutically acceptable salt or solvate thereof.

Also provided is a method for eradicating a *H. pylori* infection in a subject at a high risk of developing gastric cancer, wherein the subject is infected with *H. pylori*, the method comprising administering to the subject an effective amount of a halogenated salicylanilide, or a pharmaceutically acceptable salt or solvate thereof. Subjects at high risk of developing gastric cancer include, for example, H. pylori infected subjects with one or more of: atrophic gastritis, premalignant gastric lesions (e.g. gastric dysplasia), previously resected malignant gastric neoplasm and a family history of gastric cancer).

Also provided is a method for eradicating a H. pylori infection in a subject, wherein the subject has a gastric epithelial lesion, the method comprising administering to the subject an effective amount of a halogenated salicylanilide, or a pharmaceutically acceptable salt or solvate thereof. It may be that the gastric epithelial lesion is a premalignant lesion, for example gastric epithelial dysplasia or gastric adenoma. It may be that the gastric epithelial lesion is a malignant lesion (e.g. early gastric cancer).

It may be that the disease or infection caused by or associated with H. pylori is an extragastric disease selected from: iron-deficiency anaemia, idiopathic thrombocytopenic purpura (ITP), vitamin B12 deficiency, insulin resistance, metabolic syndrome, diabetes mellitus and non-alcoholic liver disease, acute coronary syndrome, cerebrovascular disease and neurodegenerative disease (e.g. dementia or Alzheimer's disease).

It may be that the disease or infection caused by or associated with H. pylori is an extragastric disease selected from: iron-deficiency anaemia, idiopathic thrombocytopenic purpura (ITP) and vitamin B12 deficiency.

In certain embodiments, in the methods described herein the subject is not treated concurrently with an agent that increases the permeability of a bacterial cell membrane, for example any of the permeability agents disclosed in WO 2017/200396.

In certain embodiments, in the methods described herein the subject is not treated concurrently with an efflux pump inhibitor, for example any of the efflux inhibitors disclosed in WO 2016/080846.

In certain embodiments, in the methods described herein the subject is not treated concurrently with a bicarbonate.

The halogenated salicylanilide may be used in any of the methods disclosed herein to treat a recurrent H. pylori infection, wherein the infection has recurred following prior treatment of the subject with an antibiotic (or other agent) other than a halogenated salicylanilide. Accordingly, it may be that the methods described herein are used as a second or third-line treatment of a H. pylori infection where an earlier therapy has either failed to eradicate the infection and/or the H. pylori infection has recurred. For example, the halogenated salicylanilide may be used to treat a H. pylori infection which has recurred in a subject following prior treatment of the subject with one or more antibiotic selected from: clarithromycin, amoxicillin, tetracycline, doxycycline, a nitroimidazole (e.g. metronidazole), fluoroquinolone, rifabutin, levofloxacin and ciprofloxacin.

It may be that the halogenated salicylanilide is used in any of the methods disclosed herein to treat a H. pylori infection which is resistant to an antibiotic agent used to treat the H. pylori infection. Accordingly, there is provided a halogenated salicylanilide, or a pharmaceutically acceptable salt thereof, for use in the treatment of a H. pylori infection which is resistant to an antibiotic agent other than the halogenated salicylanilide.

It may be that the H. pylori is resistant to an antibiotic agent approved by the US FDA or European Medicines Agency prior to 1 Feb. 2019, preferably an antibiotic approved for use in the treatment of a H. pylori infection. It may be that the H. pylori is resistant to an antibiotic selected from: clarithromycin, amoxicillin, tetracycline, doxycycline, a nitroimidazole (e.g. metronidazole), fluoroquinolone, rifabutin, levofloxacin and ciprofloxacin. It may be that the H. pylori is resistant to an antibiotic selected from: clarithromycin and amoxicillin.

It may be that the subject is tested for an H. pylori infection and when an infection is detected, the subject is treated by orally administering the halogenated salicylanilide to eradicate the H. pylori infection. The diagnosis of an H. pylori infection in the subject may be carried out using well known methods as described below in the Detailed Description.

Also contemplated is treating the subject without confirming the presence of an H. pylori infection prior to administration of the halogenated salicylanilide. For example, where a subject presents with the symptoms of a gastric condition that is known to be associated with H. pylori infection, it may be appropriate to orally administer the halogenated salicylanilide without first confirming the presence of the H. pylori infection. This approach removes the cost associated with testing for the presence of an infection and also reduces the time from the subject first presenting to a physician with symptoms (or e.g. detecting gastric inflammation as part of an endoscopic investigation) and the subject receiving treatment with the halogenated salicylanilide. This approach may be particularly suitable where a physician considers that the gastric disease or condition is highly likely to have been caused by or associated with H. pylori and/or where it is considered that the subject is likely to be infected. Accordingly, reference herein to treating a subject that is infected with H. pylori, or eradicating an infection in a subject, herein encompasses both subjects where the infection or colonisation has been confirmed prior to treatment with the halogenated salicylanilide as well as subjects where the H. pylori infection or colonisation has not been confirmed prior to treatment with the halogenated salicylanilide.

Halogenated salicylanilides are also known as 2-hydroxy-N-phenylbenzamides or 2-hydroxybenzanilides. Salicylanilides are weakly acidic phenolic compounds. Halogenated salicylanilides are salicylanilides substituted by at least one halo group. Any halogenated salicylanilide possessing antibacterial activity against H. pylori may be used in the present invention. For example, the halogenated salicylanilide may be any of the niclosamide analogues described in WO 2008/021088, which are incorporated herein by reference thereto.

The halogenated salicylanilide may be a halogenated salicylanilide of the formula (I):

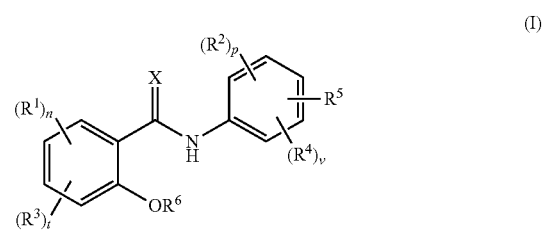

wherein
X is O or S;
$R^1$ and $R^2$ are at each occurrence independently selected from halo;
$R^3$ and $R^4$ are at each occurrence independently selected from H, $C_{1-6}$ alkyl, $-OR^{41}$, $-NO_2$ and $-CN$;
$R^5$ is H or $-L^1-R^7$;

R$^6$ is H or —C(O)R$^{42}$;
L$^1$ is selected from a bond, O, S, or —(CR$^{43}$R$^B$)$_o$—, wherein o is 1 or 2;
R$^7$ is phenyl, unsubstituted or substituted with 1, 2, or 3 groups selected from halo, C$_{1-4}$ alkyl, —OR$^{44}$, —NO$_2$ and —CN;
R$^{41}$, R$^{42}$, R$^{43}$ and R$^{44}$ are at each occurrence independently selected from H and C$_{1-4}$ alkyl;
R$^B$ is at each occurrence selected from H, C$_{1-4}$ alkyl and —CN;
n and p are each independently selected from 0, 1, 2, 3 or 4, with the proviso that n+p is at least 1;
t and v are independently selected from 0, 1 and 2;
or a pharmaceutically acceptable salt, or solvate thereof.

The halogenated salicylanilide may be selected from the group consisting of: niclosamide, closantel, oxyclozanide, rafoxanide, or a pharmaceutically acceptable salt or solvate thereof.

The halogenated salicylanilide may be selected from the group consisting of: niclosamide and oxyclozanide, or a pharmaceutically acceptable salt or solvate thereof.

The halogenated salicylanilide may be niclosamide, or a pharmaceutically acceptable salt or solvate thereof.

The halogenated salicylanilide may be niclosamide.

The halogenated salicylanilide may be oxyclozanide.

Suitably the halogenated salicylanilide or a pharmaceutically acceptable salt or solvate thereof is administered to the subject orally.

Suitably the halogenated salicylanilide or a pharmaceutically acceptable salt or solvate thereof is administered to the subject orally in the form of a pharmaceutical composition comprising the halogenated salicylanilide or a pharmaceutically acceptable salt or solvate thereof, and a pharmaceutically acceptable excipient (e.g. binders, fillers, carriers and/or lubricants). Suitably the pharmaceutical composition releases the halogenated salicylanilide in the stomach. It may be that the pharmaceutical composition is in the form of a tablet, granule, powder, solution, emulsion or suspension suitable for oral administration to the subject.

It may be that the methods described herein are suitable for the treatment of conditions associated with other *Helicobacter* species and/or for the eradication of infections by other *Helicobacter* species of bacteria. Accordingly, also contemplated is any of the methods described herein wherein the bacteria is any *Helicobacter* species, including, but not limited to *H. pylori*. For example, any of the methods disclosed herein may be used for the treatment of an infection or disease caused by or associated with a *Helicobacter* Spp. selected from *H. pylori*, *H. acinonychis*, *H. bizzozeronii*, *H. bilis*, *H. canadensis*, *H. canis*, *H. cetorum*, *H. cinaedi*, *H. fells*, *H. fennelliae*, *H. heilmannii*, *H. hepaticus*, *H. macacae*, *H. mustelae*, *H. pametensis*, *H. pullorum*, *H. rodentium*, *H salomonis*, *H. suis* and *H. winghamensis*. For example, it may be a *Helicobacter* Spp. selected from *H. pylori*, *H. acinonychis*, *H. bilis.*, *H. bizzozeronii*, *H. cetorum*, *H. felis*, *H. heilmannii* *H. mustelae*, *H. pametensis*, *H salomonis* and *H. suis*. In certain embodiments it may be that the *Helicobacter* Spp. is selected from *H. pylori*, *H. bilis.*, *H. bizzozeronii*, *H. fells*, *H. heilmannii*, *H. pametensis* and H salomonis.

The subject is suitably a warm-blooded mammal. Preferably the subject is a human. When the subject is human the methods described herein are preferably for the treatment of an infection or disease caused by or associated with *H. pylori*.

It may be that the subject is a non-human animal. In certain embodiments the subject a non-human animal and any of the methods described herein is for the treatment of an infection or disease caused by or associated with a *Helicobacter* Spp. For example in some embodiments there is provided a method for A method for eradicating a *Helicobacter* Spp. infection in a subject, the method comprising orally administering to the subject an effective amount of a halogenated salicylanilide, or a pharmaceutically acceptable salt or solvate thereof.

It may be that the subject is a companion animal, for example a dog or a cat. In certain embodiments the subject is a companion animal (e.g. a cat or a dog) and any of the methods described herein is for the treatment of an infection or disease caused by or associated with a *Helicobacter* Spp.

In certain embodiments the subject is a cat or a dog and any of the methods described herein is for the treatment of an infection or disease caused by or associated with a *Helicobacter* Spp. selected from *H. pylori*, *H. bilis.*, *H. bizzozeronii*, *H. fells*, *H. heilmannii*, *H. pametensis* and H salomonis.

In certain embodiments the subject is a dog and any of the methods described herein is for the treatment of an infection or disease caused by or associated with a *Helicobacter* Spp. selected from *H. felis*, *H. bizzozeronii*, *H. salomonis*, *H. bilis*, and *H. heilmannii*.

In certain embodiments the subject is a cat and any of the methods described herein is for the treatment of an infection or disease caused by or associated with a *Helicobacter* Spp. selected from *H. fells*, *H. pametensis*, *H. pylori* and *H. heilmannii*.

BRIEF DESCRIPTION OF THE DRAWINGS

Embodiments of the invention are further described hereinafter with reference to the accompanying drawings, in which:

FIGS. 5A-D show microscope slides illustrating the effect of niclosamide on vacuolation of AGS cells infected with *H. Pylon*. A sub-MIC concentration of niclosamide (0.2 µg/mL) prevented vacuolation of the AGS cells. (A) AGS alone; (B)

AGS treated with niclosamide; (C) AGS cells infection with *H. pylori*; (D) AGS cells cocultured with *H. pylori* and niclosamide.

FIG. 5E shows that niclosamide down-regulated vacA gene (291 bp) expression at sub-MIC (0.2 μg/mL), compared to expression of the housekeeping gene rpoB (301 bp) at niclosamide concentrations of 150 ng/mL and 200 ng/mL compared to a DMSO control. ***p<0.001, students t-test comparing DMSO control.

Figure 6:
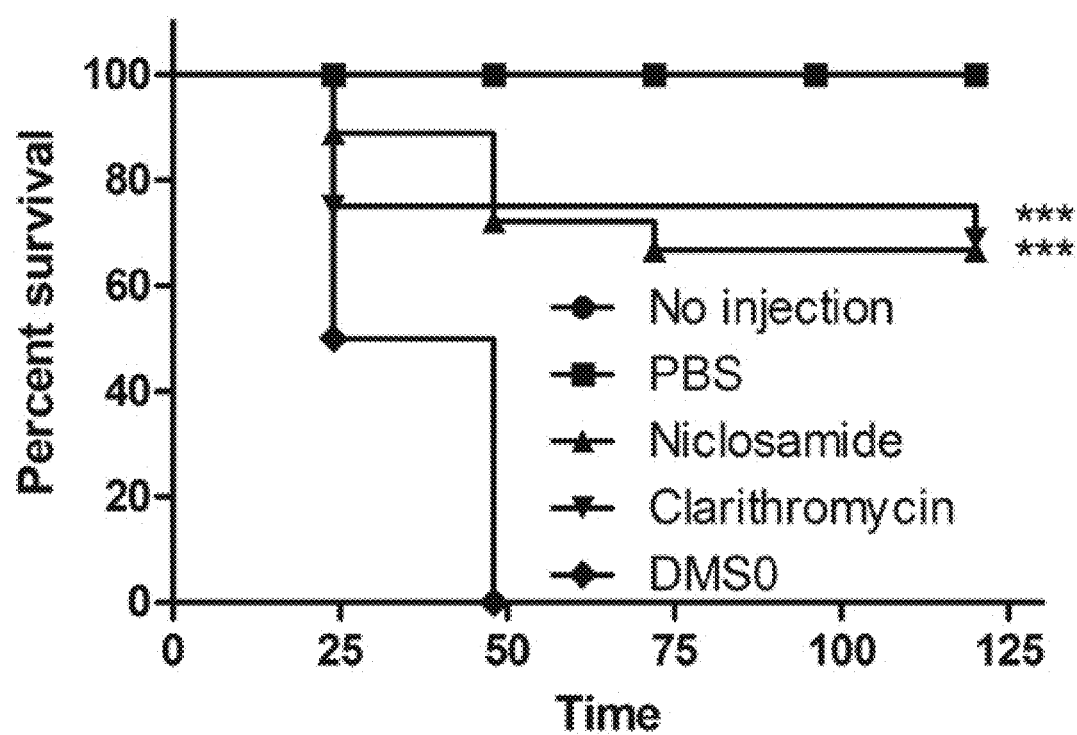
Figure 7A:
Figure 7B:
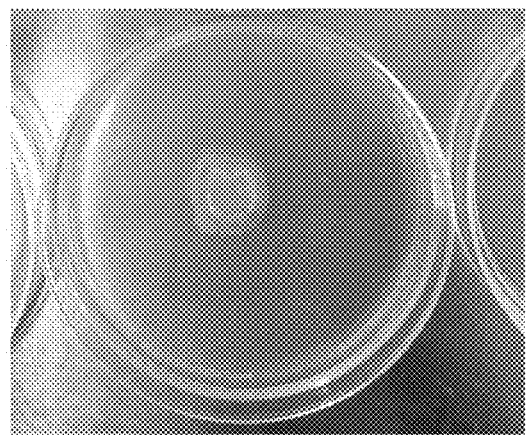
Figure 7C:
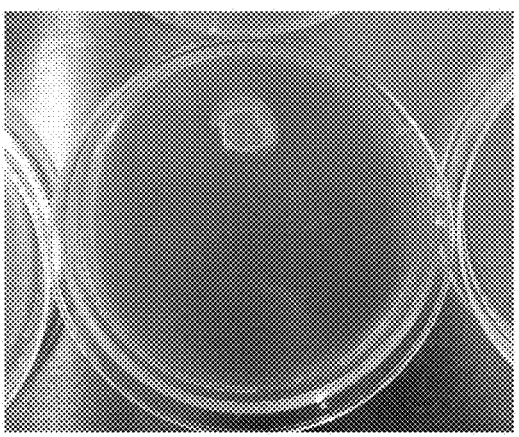
Figure 7D:
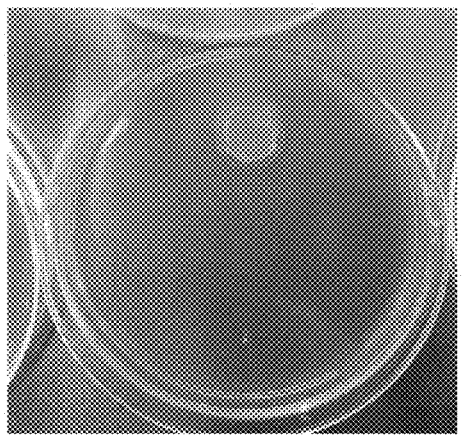
Figure 7E:
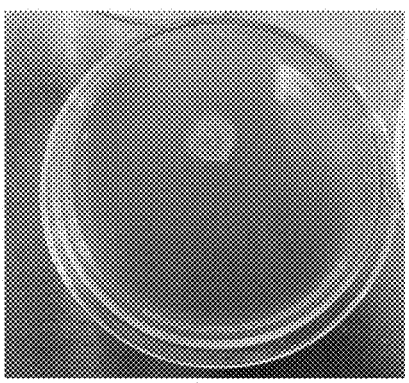

FIG. 6 shows survival curves in the in-vivo *Galleria mellonella* model for the evaluation of antimicrobial agents against *H. Pylon* infection. The y-axis shows the % survival and the x-axis time. Survival curves are shown for niclosamide (25 mg/kg) and a comparator clarithromycin (10 mg/kg). Also shown are control arms with no injection; a sham injection of phosphate buffered saline only and no antibiotic treatment ("PBS"); and inoculation with *H. Pylon* and a sham injection of DMSO ("DMSO"). In FIG. 6 the "no injection" group and the "PBS" group datapoints overlay each other and remained at 100% throughout the test FIG. 7 shows the results of a motility assay carried out to show the effect of different concentrations of niclosamide on the motility of *H. Pylon* bacteria. *H. Pylon* was cultured in a soft (0.4%) agar layer in the presence or absence of niclosamide placed on top of a pre-cast agar layer (1.5% agar). This figure illustrates the extent of the migration beyond the boundary of the soft agar top layer across the lower pre-cast agar layer. The extent of migration is illustrated by the spread of bacteria beyond the edge of the soft agar layer. Niclosamide treatment impeded *H. Pylon* swarming movement in a dose-dependent manner. In FIG. 7A was the DMSO (control); and FIG. 7B-E niclosamide containing soft agar. FIG. 7B 75 ng/mL; 7C 100 ng/mL; FIG. 7D 150 ng/mL; and FIG. 7E 200 ng/mL.

Figure 8:
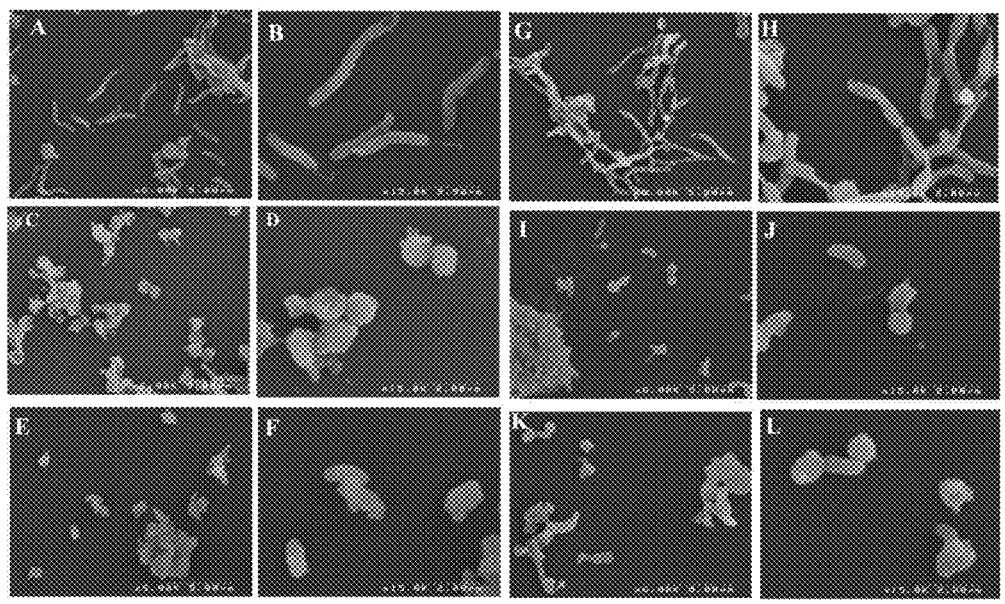

FIG. 8 shows scanning electron micrographs of *H. Pylon* that are untreated ((A) and (B)), or treated with niclosamide at: 1× MIC ((C) and (D)); 4×MIC ((E) and (F)); 8×MIC ((G) and (H)). FIG. 8 also shows the effect of the control antibiotics amoxicillin ((I) and (J) at 10× MIC) and carbonyl cyanide m-chlorophenylhydrazone (CCCP) ((k) and (I) at 10 μM) on *H. Pylon*.

Figure 9:
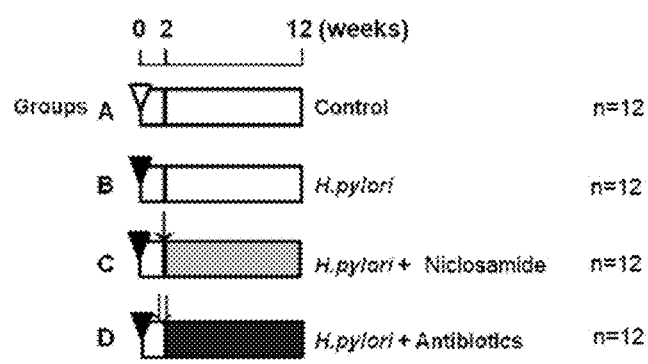

FIG. 9 is a schematic of a suitable 12 week study that could be carried out to assess the in vivo effects of a halogenated salicylanilide against H. pylon in a Mongolian gerbil animal model. In FIG. 9 ▼ indicates *H. pylori*-infection; ∇ indicates administration of culture broth; ↓ indicates administration of Niclosamide; ▽ indicates administration of antibiotics: clarithromycin (CAM), amoxicillin (AMPC), and/or a PPI (e.g. esomeprazole); "n" refers to the number of animals used in each arm of the study.

DETAILED DESCRIPTION

Definitions

"Dysplasia" refers to a non-cancer abnormality of development or of growth and differentiation of cells, for example in gastric epithelial cells. The cells often appear to be of an abnormal size or shape and/or pigmentation.

"Hyperplasia" refers to a preneoplastic increase in the number of cells in a tissue (increase cell proliferation), wherein the cells appear to be normal cells under an optical microscope.

"Neoplasm" refers to an abnormal cell growth in a tissue or organ and can be benign or malignant lesions.

"Proton pump inhibitor" "PPI" describe suppress gastric acid secretion by the specific inhibition of the H+,K+ATPase enzyme system (proton pump) at, in or near the secretory surface of the gastric parietal cells. Examples of proton pump inhibitors include benzimidazole and azabenzimidazole derivatives, for example omeprazole, hydroxyomeprazole, esomeprazole, lansoprazole, dexlansoprazole, pantoprazole, rabeprazole, dontoprazole, habeprazole, perprazole, tenatoprazole, ransoprazole, pariprazole, leminoprazole, or pharmaceutically acceptable salt, or solvate, or derivative thereof. Particular examples of PPIs include a compound selected from: omeprazole, esomeprazole, lansoprazole, dexlansoprazole, pantoprazole and rabeprazole, or pharmaceutically acceptable salt, or solvate, or derivative thereof.

PPIs are acid-labile weak bases. PPIs are generally formulated to protect the compound from degradation in gastric acid. Suitable formulations include enteric-coated or delayed release compositions, gelatin capsules or coated granules. PPIs may also be formulated with a basic compound such as a bicarbonate, to confer a temporary gastric pH increase and protection for the PPI. Certain PPI's, for example lansoprazole, pantoprazole, and esomeprazole are available as intravenous formulations.

Reference to administration "concurrently" or "concurrent use" herein includes the separate, simultaneous or sequential administration of the halogenated salicylanilide with another therapy. The other therapy may be administered to the subject by the same or different routes of administration to that of the halogenated salicylanilide. For example, the other therapy may be administered to the subject orally, intravenously, subcutaneously, or topically. The halogenated salicylanilide and the other therapy may be administered as a combined preparation; however, generally they will be administered as separate dosage forms to enable the dose and dosing regimen of each to be tailored accordingly. Concurrent use includes the administration of the halogenated salicylanilide before administration of the other therapy, administration of the halogenated salicylanilide substantially simultaneously with the other therapy or administration of the halogenated salicylanilide after administration of the other therapy. Where the halogenated salicylanilide and the other therapy are administered separately, the time period between administration of the two agents is such that the therapeutic benefit of the first agent is present when the second agent is administered to the subject. The interval between administrations will depend on the disease or medical condition being treated as well as the nature of the two therapeutic agents. For example, the interval between administration of the two agents may be 1 hour, 4 hours, 8 hours, 12 hours, 24 hours, 1 week, 2 weeks or 4 weeks.

Reference to a "halogenated salicylanilide, or a pharmaceutically acceptable salt or solvate thereof" is intended to encompass the halogenated salicylanilide, pharmaceutically acceptable salts of the halogenated salicylanilide, solvates (e.g. hydrates) of the halogenated salicylanilide salts and solvates (e.g. hydrates) of the halogenated salicylanilide.

References to "treating" or "treatment" include prophylaxis as well as the alleviation of established symptoms of a disease or medical condition. Thus, "treatment" as used herein includes therapeutic (curative) treatment, prophylactic (preventing) treatment and palliative (alleviating) treatment of the indicated states, disorders or conditions. "Treating" or "treatment" of a state, disorder or condition therefore includes: (1) preventing or delaying the appearance of clinical symptoms of the state, disorder or condition developing in a subject, for example a human, that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms. Accordingly, in the context of treating infections caused by *H. pylori* bacteria includes:

(i) the prevention of a disease caused by *H. pylori;*
(ii) the suppression of a disease caused by *H. pylori;*
(iii) the relief of symptoms of a disease caused by *H. pylori;*
(iv) inhibiting or preventing progression of a disease caused by *H. pylori.*
(v) the eradication of an asymptomatic *H. pylori* infection;
(vi) the eradication of a symptomatic *H. pylori* infection;
(vii) clearance of a *H. pylori* infection;
(viii) suppressing or reducing growth of a *H. pylori* bacteria in a subject;
(ix) preventing or reducing the risk of recurrence of an *H. pylori* infection in a subject.

Reference to "eradicating or eradication of a *H. pylori* infection" is intended to encompass "treatment" of an infection as defined above. However, in preferred embodiments, reference to "eradicate" or "eradication" refers to the complete elimination of all or substantially all of the *H. pylori* from the subject. Suitably the methods described herein act to remove substantially all viable *H. pylori* from the subject, thereby preventing or minimising the risk of recurrence of the *H. pylori* infection. Subjects can be tested following treatment to confirm if the *H. pylori* infection has been eradicated. Suitably a subject is tested for the presence of *H. pylori* at least 28 days, but preferably no more than 56 days after the last dose of the halogenated salicylanilide. The presence of *H. pylori* may be determined using known diagnostic methods, for example by taking endoscopic biopsies and culturing/histology, or more preferably, using a non-invasive method such as the urea breath test, serology or stool antigen test.

Reference to "infection" is intended to also encompass colonization of the subject with *Helicobacter*. Accordingly "infection" as used herein encompasses both non-symptomatic/pathogenic colonisation by bacteria as well as symptomatic infections unless stated otherwise.

As used herein, a "therapeutically effective amount" or "effective amount" means the amount of a compound that, when administered to a subject, for example a human, for treating a disease, is sufficient to effect such treatment for the disease. The "therapeutically effective amount" will vary depending on the particular halogenated salicylanilide, the disease and its severity and the age, weight, etc., of the subject to be treated.

"Minimum inhibitory concentration" (MIC) is the lowest concentration of an antibacterial agent that inhibits the visible growth of a microorganism after overnight incubation.

"Minimum bactericidal concentration" (MBC) is the lowest concentration of an antibacterial agent required to kill a particular bacterium.

"Bactericidal" refers to compounds that act to kill the bacteria.

Reference to a compound being "bacteriostatic" means that the compound is effective preventing or slowing the growth of a bacteria (i.e. maintains the bacteria in a stationary phase of growth), but does not necessarily kill the bacteria. Generally when an agent is bacteriostatic, if the treatment is stopped whilst the bacteria are still viable in the host the bacteria will start to grow again. Generally the duration of bacteriostatic treatment should be sufficiently long to provide the host defense mechanisms sufficient time to eradicate the bacteria causing the infection. The bacteriostatic or bactericidal effects of a compound on a bacteria may be determined using well-known in-vitro methods, for example the time to kill assay described in the Examples herein and Rajamuthiah. et al. (Repurposing salicylanilide anthelmintic drugs to combat drug resistant *Staphylococcus aureus*. PLoS One 10, 2015).

References to "synergy" of the halogenated salicylanilide with other therapeutic agents described herein refer to an activity which is greater than the sum of the individual agents used alone. The degree of antimicrobial synergy may be assessed by calculating the fractional inhibitory concentration index (FICI) using the checkerboard assay described in the Examples herein. For two agents A and B, the FICI is calculated as:

$$FICI = MIC_{A-B\ in\ combination}/(MIC_{A\ alone} + MIC_{B\ alone})$$

Synergy occurs when the FICI is ≤0.5; partial synergy for 0.5≤FICI≤1.0; no interaction 1.0>FICI; and antagonism FICI >4.0.

"Colony-forming unit (CFU)" is an estimate of the number of viable bacteria or fungal cells in a sample. Viable is defined as the ability to multiply via binary fission under the controlled conditions.

The term "halo" or "halogen" refers to one of the halogens, group 17 of the periodic table. In particular, the term refers to fluorine, chlorine, bromine and iodine.

The term "$C_m$-$C_n$" refers to a group with m to n carbon atoms.

The term "$C_1$-$C_6$alkyl" refers to a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. "$C_1$-$C_4$ alkyl" similarly refers to such groups containing up to 4 carbon atoms.

Where a moiety is substituted, it may be substituted at any point on the moiety where chemically possible and consistent with atomic valency requirements. The moiety may be substituted by one or more substituents, e.g. 1, 2, 3 or 4 substituents; optionally there are 1 or 2 substituents on a group. Where there are two or more substituents, the substituents may be the same or different.

Substituents are only present at positions where they are chemically possible, the person skilled in the art being able to decide (either experimentally or theoretically) without undue effort which substitutions are chemically possible and which are not.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention contemplates pharmaceutically acceptable salts of the halogenated salicylanilide compounds of the invention. These may include the acid addition and base salts of the compounds. These may be acid addition and base salts of the compounds. Suitable acid addition salts are formed from acids which form non-toxic salts. Suitable base salts are formed from bases which form non-toxic salts.

Pharmaceutically acceptable salts of the halogenated salicylanilide compounds may be prepared by for example, one or more of the following methods:
(i) by reacting the compound of the invention with the desired acid or base; or
(ii) by converting one salt of the compound of the invention to another by reaction with an appropriate acid or base or by means of a suitable ion exchange column.

These methods are typically carried out in solution. The resulting salt may precipitate out and be collected by filtration or may be recovered by evaporation of the solvent. The degree of ionisation in the resulting salt may vary from completely ionised to almost non-ionised.

It is also to be understood that certain compounds of the invention, or salts or solvates thereof, may exist in solvated as well as unsolvated forms such as, for example, hydrated forms. It is to be understood that the invention encompasses all such solvated forms that possess activity against *H. Pylori* bacteria.

It is also to be understood that the halogenated salicylanilides of the invention may exhibit polymorphism, and that the invention encompasses all such forms that possess activity against *H. Pylori* bacteria.

It is further to be understood that the halogenated salicylanilide may be used in the form of suitable pharmaceutically-acceptable pro-drug of the compound and that such prodrugs are intended to be encompassed by the invention. Accordingly, the halogenated salicylanilide may be administered in the form of a pro-drug, that is a compound that is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable solvate derivatives that may be formed at a hydroxy group in a compound.

Accordingly, the present invention includes the halogenated salicylanilides as defined hereinbefore when made available by organic synthesis and when made available within the human or animal body by way of cleavage of a pro-drug thereof. Accordingly, the present invention includes those halogenated salicylanilide compounds that are produced by organic synthetic means and also such compounds that are produced in the human or animal body by way of metabolism of a precursor compound, that is the halogenated salicylanilide may be a synthetically-produced compound or a metabolically-produced compound.

A suitable pharmaceutically-acceptable pro-drug of a halogenated salicylanilide compound is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

Adhesion of *H. pylori* to Gastric Epithelial Cells

Adhesion of *H. pylori* to gastric epithelial cells plays an important role in the initial stages of *H. pylori* infection of gastric epithelial cells and is implicated in the pathogenesis of *H. pylori* (Odenbreit. International journal of medical microbiology 295, 317-324 (2005)). A high proportion of the population are colonized by *H. pylori*, however, not all subjects will develop symptomatic pathological conditions such as gastritis, peptic ulcer disease or gastric cancer. The majority of *H. pylori* bacteria colonize the gastric mucosa, however, a proportion of the bacteria adhere to the surface of gastric mucosal epithelial cells (Hessey et al. Gut 1990; 31:134-138). Adhesion of *H. pylori* to epithelial cells results in damage to the epithelium, induces inflammation and enables the bacteria to deliver toxins to the gastric epithelial cells such as VacA and CagA (Amieva et al. Gastroenterology 2008; 134:306-323 and Enroth, International Encyclopedia of Public Health, 2nd edition, Volume 3, 527-531). CagA induces a Snail-mediated EMT (epithelial-mesenchymal transition), which is a hallmark of gastric cancer (Lee et al. Nature Communications, July 2014, 5:4423 I DOI: 10.1038/ncomms5423). The increased inflammation associated with bacterial adhesion to the gastric epithelium can lead to the development of for example gastritis, peptic ulcer disease and atrophic gastritis (a precursor to gastric cancer) (Guruge et al. Proc. Natl. Acad. Sci. USA 95 (1998) 3925-3929). Adhesion of *H. pylori* to gastric epithelial cells has been shown to increase the severity of *H. pylori* induced gastritis and associated pathogenesis, including the development of gastric cancer. These effects are thought to be mediated by the CagA toxin expressed by the bacteria bound to the gastric epithelial cells (McGuckin et al. Gastroenterology 2007; 133:1210-1218; Guruge et al. Proc. Natl. Acad. Sci. USA 1998; 95:3925-3930; and Censini et al. Proc. Nat. Acad. Sci. USA 1996; 93:14648-14653).

Accordingly, prevention or inhibition of adhesion of *H. pylori* to epithelial cells and/or removal of bacteria adhered to the cells may prevent or reduce the risk of pathogenesis associated with *H. pylori*. The Examples herein show that niclosamide is effective in the removal of *H. pylori* adhered to the gastric epithelial cells and may therefore be effective in preventing pathological effects associated with *H. pylori* infections. A therapy which is effective in removing bacteria adhered to gastric epithelial cells, or which prevents adherence of bacteria to such cells, may be effective to prevent or inhibit pathogenesis, without the need to completely eradicate *H. pylori* from the gastric mucosa. Inhibition of adhesion of the *H. pylori* and/or removal of bacteria adhered to gastric epithelial cells may also enhance the effectiveness of the halogenated salicylanilide eradicating the *H. pylori* thereby reducing the risk of recurrence of the infection.

Accordingly, also provided is a method for inhibiting the adhesion of *H. pylori* to gastric epithelial cells in a subject infected by *H. pylori*, the method comprising orally administering to the subject an effective amount of a halogenated salicylanilide, or a pharmaceutically acceptable salt or solvate thereof.

Also provided is a method for reducing or eliminating *H. pylori* adhered to gastric epithelial cells in a subject, the method comprising orally administering to the subject an effective amount of a halogenated salicylanilide, or a pharmaceutically acceptable salt or solvate thereof.

Also provided is a method for treating, preventing, or reducing the risk of developing, a pathological condition associated with *H. pylori* in a subject infected with *H. pylori* (e.g. gastric ulcer, duodenal ulcer, gastritis, atrophic gastritis or gastric cancer), the method comprising administering to the subject an effective amount of a halogenated salicylanilide, or a pharmaceutically acceptable salt or solvate thereof, wherein the method inhibits or prevents adhesion of *H. pylori* to gastric epithelial cells in the subject. It may be that the method prevents or reduces CagA induced EMT. It may be that the method prevents or reduces the risk of developing gastric cancer in the subject, wherein the method prevents or inhibits adhesion of *H. pylori* to gastric epithelial cells in the subject.

Invasion of Gastric Epithelial Cells by *H. pylori*

*H. pylori* is able to invade gastric epithelial cells and reside in those cells (Dubois et al Cell. Microbiol. 2007; 9:1108-1116). This can make the eradication of *H. pylori* infections difficult using conventional antibiotic treatments, because these may not be effective against those bacteria that have invaded into gastric epithelial cells (Deen et al. Autophagy. 2013 May; 9(5):639-5). Failure to eradicate intracellular *H. pylori* may increase the risk of the infection recurring and/or progression of *H. pylori* induced pathological conditions resulting from the invasion. Cellular invasion by *H. pylori* and intracellular expression of virulence genes such as vacA and cagA by *H. pylori* may be involved in gastric carcinogenesis (Dubois et al, supra).

The Examples herein illustrate that niclosamide eradicates intracellular *H. pylori* from gastric epithelial cells and is therefore expected to provide an effective therapy for the eradication of *H. pylori* infections. Accordingly, also provided is a method for eradicating a *H. pylori* infection in a subject, the method comprising orally administering to the subject an effective amount of a halogenated salicylanilide, or a pharmaceutically acceptable salt or solvate thereof, wherein the treatment reduces or eliminates intracellular *H. pylori* from gastric epithelial cells.

Also provided is also provided is a method for treating or preventing a disease or infection caused by or associated with *H. pylori* in a subject infected with *H. pylori*, the method comprising orally administering to the subject an effective amount of a halogenated salicylanilide, or a pharmaceutically acceptable salt or solvate thereof, wherein the treatment reduces or eliminates intracellular *H. pylori* from gastric epithelial cells Also provided is a method for preventing or reducing the invasion of *H. pylori* into gastric epithelial cells in a subject infected by *H. pylori*, the method comprising orally administering to the subject an effective amount of a halogenated salicylanilide, or a pharmaceutically acceptable salt or solvate thereof.

It may be that inhibiting invasion of *H. pylori* into gastric epithelial cells and/or eradicating *H. pylori* that have invaded gastric epithelial cells prevents or reduces the risk of the subject developing a pathological condition caused by or associated with the *H. pylori* infection, for example a peptic ulcer or gastric cancer.

Inhibition of IL-8

*H. pylori* infection induces IL-8 secretion which, in turn, initiates neutrophil chemotaxis and activation, ultimately causing mucosal damage (Yamaoka et al. Gut 41, 442-451 (1997)). IL-8 secretion is an important factor in the immunopathogenesis of conditions associated with *H. pylori* infections, for example peptic ulcer disease and gastric carcinogenesis. The Examples herein show that niclosamide is effective in reducing IL-8 secretion from *H. pylori* infected gastric mucosal cells.

Accordingly, also provided is a method for inhibiting *H. pylori* induced IL-8 secretion in a subject infected by *H. pylori*, the method comprising administering to the subject an effective amount of a halogenated salicylanilide, or a pharmaceutically acceptable salt or solvate thereof.

Also provided is a method for treating or preventing a disease or infection caused by or associated with *H. pylori* in a subject infected by *H. pylori*, the method comprising orally administering to the subject an effective amount of a halogenated salicylanilide, or a pharmaceutically acceptable salt or solvate thereof, wherein the method inhibits and/or reduces *H. pylori* induced IL-8 secretion in the subject.

Also provided is a method for treating of preventing atrophic gastritis in a subject infected by *H. pylori*, the method comprising orally administering to the subject an effective amount of a halogenated salicylanilide, or a pharmaceutically acceptable salt or solvate thereof. Suitably the method inhibits and/or reduces *H. pylori* induced IL-8 secretion in the subject.

Vacuolation

*H. pylori* bacteria secrete the toxin VacA. This toxin binds to gastric epithelial cells and is internalised resulting in vacuolation (Galmiche et al. Gut microbes 1, 392-395 (2010)). The vacuolation enhances the invasion of the *H. pylori* and provides an intracellular niche where the bacteria can reside and mediates long-term survival of the bacteria. *H. pylori* strains which express the VacA s1 or m1 are associated with an increased risk of gastric cancer (Matos et al. Eur J Gastroenterol Hepatol. 2013; 25(12):1431-1441). Preventing or inhibiting *H. pylori* mediated vacuolation of gastric epithelial cells may therefore be beneficial.

The Examples herein show that niclosamide down-regulated expression of VacA and prevented or inhibited vacuolation of gastric epithelium cells. Interestingly, these effects were observed even at sub MIC concentrations. Accordingly, it may be possible to treat a subject infected with *H. pylori* a low dose (i.e. sub MIC) to prevent or inhibit vacuolation and/or to reduce the pathogenicity of the *H. pylori* infection in the subject. It may be that the method comprises contacting the *H. pylori* bacteria with a halogenated salicylanilide, or a pharmaceutically acceptable salt or solvate thereof (e.g. niclosamide) at a concentration which is below the MIC of halogenated salicylanilide. Use of a low-dose of the halogenated salicylanilide may be sufficient to inhibit *H. pylori* mediated vacuolation without necessarily killing or eradicating the *H. pylori* bacteria present in the subject. It is also contemplated that higher doses of the halogenated salicylanilide are used to both inhibit vacuolation and to eradicate the *H. pylori* infection in the subject.

Accordingly there is provided a method for treating or preventing a disease or infection caused by or associated with *H. pylori* in a subject infected by *H. pylori*, the method comprising orally administering to the subject an effective amount of a halogenated salicylanilide, or a pharmaceutically acceptable salt or solvate thereof, wherein the method inhibits *H. pylori* mediated vacuolation of gastric epithelial cells.

*H. pylori* Motility

*Helicobacter pylori* is a flagellated bacteria. The flagella play an important role in the colonisation of the gastrointestinal mucosa and the persistence of the infection (Gu. Chin. J. Lab. Med. 2008; 31:733-736; and Ottemann et al. Infect Immun. 2002 April; 70(4):1984-90). The Examples herein show that niclosamide inhibits *H. pylori* motility, even at sub-MIC concentrations. Accordingly, the methods disclosed herein may prevent or inhibit *H. pylori* colonisation and the subsequent development of pathogenic conditions such as peptic ulcer disease or gastric cancer.

Virulent Strains of *H. pylori*

It may be that the *H. pylori* is a strain that expresses the CagA virulence factor. The expression of CagA is associated with the pathogenicity of the *H. pylori* and infection with such strains may be associated with a higher prevalence of, for example gastric cancer or peptic ulcer. CagA is a known oncoprotein which alters intracellular signal transduction pathways facilitating malignant transformation of gastric epithelial cells (Backert et al. Cancer Res. 2016 Jul. 15; 76(14):4028-31).

It may be that the method of treatments disclosed herein are directed to the treatment of subjects infected by *H. pylori* strains which express high levels of CagA. For example, a method of treating or preventing gastric cancer in a subject infected with *H. pylori* expressing CagA, the method comprising administering to the subject an effective amount of a halogenated salicylanilide, or a pharmaceutically acceptable salt or solvate thereof.

*H. pylori* expressing VacA s1 or m1 is associated with an increased risk of gastric cancer (Matos et al. supra). *H. pylori* strains which are simultaneously CagA and VacA s1/m1 genopositive are associated with a risk of gastric premalignant lesions from progressing to gastric cancer. Thus it may be that the treatments disclosed herein are used to treat subjects infected with *H. pylori* that expresses VacA s1 and/or VacA m1 and/or CagA. It may be that the *H. pylori* expresses VacAs1/m1 and CagA, particularly in the treatment of premalignant lesions to prevent oncogenesis of the lesion.

The expression of CagA and VacA by *H. Pylon* may be determined using known methods, for example VacA expression may be determined using gene expression assays as described in the Examples.

Disease or Infections Caused by or Associated with *H. pylori*

*H. Pylon* infections cause or are associated with numerous diseases and medical conditions. For example, a disease or medical condition selected from: dyspepsia, gastritis, peptic ulcer disease, gastric cancer and gastric mucosa-associated lymphoid tissue (MALT) lymphoma. Treatment of a subject infected with *H. Pylon* by oral administration of the halogenated salicylanilide, or a pharmaceutically acceptable salt or solvate thereof as described herein is expected to be beneficial in the treatment or prevention of such conditions. It may be that the method of treatment eradicates the *H. Pylon* from the subject. It may be that the method of treatment prevents the condition, for example by providing a prophylactic effect or by reducing the risk of developing a disease or condition associated with the *H. Pylon* infection. It may be that the method of treatment inhibits or reduces the risk of disease progression prevents the condition It may be that the method of treatment treats the condition, for example by alleviating one or more symptoms associated with the disease or reducing the clinical effects of the disease or curing the disease.

Non-Symptomatic Eradication of *H. Pylon*

The methods of treatment described herein may be for the treatment of an asymptomatic *H. Pylon* infection in a subject. The eradication of an *H. Pylon* infection in a subject prior to the emergence of symptoms minimises the pathogenicity of the bacteria and may be beneficial in preventing or reducing the risk of a pathogenic disease emerging. In particular, treatment of an asymptomatic *H. Pylon* infection in a subject may be beneficial in preventing or reducing the risk of the subject developing gastric cancer.

Accordingly in some embodiments there is provided a method for the eradication of an asymptomatic *H. Pylon* infection in a subject infected by *H. Pylon*, the method comprising orally administering to the subject an effective amount of a halogenated salicylanilide, or a pharmaceutically acceptable salt or solvate thereof. In this embodiment the treatment of an asymptomatic subject to eradicate the *H. Pylon* infection may inhibit or prevent atrophic gastritis, a known risk factor for gastric cancer. For example, early intervention to treat non-atrophic gastritis in a subject infected with *H. Pylon* may prevent or reduce the risk of the non-atrophic gastritis from progressing to atrophic gastritis.

Accordingly, in certain embodiments there is provided a method for the treatment of non-atrophic gastritis in a subject infected with *H. Pylon*, the method comprising orally administering to the subject an effective amount of a halogenated salicylanilide, or a pharmaceutically acceptable salt or solvate thereof. In certain embodiments there is provided a method for eradicating a *H. pylori* infection in a subject that has non-atrophic gastritis, the method comprising orally administering to the subject an effective amount of a halogenated salicylanilide, or a pharmaceutically acceptable salt or solvate thereof. It may be in these embodiments that the non-atrophic gastritis is asymptomatic.

Dyspepsia

In certain embodiments the method is for the treatment of functional dyspepsia in the subject. It may be that the method is for the eradication of *H. pylori* in a subject with functional dyspepsia.

"Functional dyspepsia" refers to chronic dyspepsia where there is no evidence of gastric lesions and is also known as non-ulcer dyspepsia, pseudo-ulcer syndrome, pyloro-duodenal irritability, nervous dyspepsia. Functional dyspepsia includes postprandial distress syndrome (PDS) and epigastric pain syndrome (EPS). Symptoms of functional dyspepsia include chronic and repetitive postprandial fullness, early satiation, epigastric pain, and epigastric burning.

It may be that the method of treatment prevents or inhibits the progression of functional dyspepsia to more serious *H. pylori* induced conditions such as chronic gastritis, atrophic gastritis, peptic ulcer disease or gastric cancer.

Gastritis

Gastritis refers to gastric inflammation, often accompanying structural mucosal changes (e.g. mucosal atrophy and/or epithelial metaplasia). A primary cause of gastritis is *H. pylori* infection. Gastritis, particularly chronic gastritis is associated with peptic ulcer disease and gastric cancer. *H. pylori* infection may lead to one or more conditions selected from: atrophic gastritis, intestinal metaplasia, gastric hyperplasia, gastric dysplasia, peptic ulcer disease, gastric adenocarcinoma as well as gastric Mucosa-Associated-Lymphoid-Tissue (MALT) lymphoma (Kuipers Basic Clin Pharmacol. Toxicol. 2006 September; 99(3):187-94)

Accordingly, in certain embodiments the method of treatment is for the treatment or prevention of gastritis in a subject infected with *H. pylori*. In certain embodiments the method of treatment is for the eradication of an *H. pylori* infection in a subject with gastritis.

The method is expected to be beneficial in the treatment of gastritis induced by or associated with *H. pylori* (i.e. *H. pylori* gastritis). The gastritis may be chronic active gastritis, chronic persistent gastritis, atrophic gastritis, acute haemorrhagic gastritis, chronic superficial gastritis, or endoscopic gastritis. Endoscopic gastritis includes signs of gastritis identified using endoscopy. Typical endoscopic findings of acute *H. pylori* infection include haemorrhagic spots on the fundus and/or high-body, nodular gastritis, and hypertrophic gastric rugae. Gastritis may also be diagnosed using well-known histological assessment of biopsy samples.

The gastritis may be pan-gastritis affecting substantially the whole of the stomach. In some embodiments the gastritis affects only a part of the stomach, for example it may be that the gastritis is antrum gastritis or corpus gastritis. In some embodiments the gastritis is corpus gastritis.

Peptic Ulcer Disease

It is well-known that *H. pylori* infection is associated with the development of peptic ulcer disease (including gastric and duodenal ulcers). *H. pylori* infection is also implicated in bleeding of peptic ulcers (Shimada et al. Nihon Rinsho 2007 October; 65(10):1824-9).

In certain embodiments the method of treatment is for the treatment or prevention of peptic ulcer disease in a subject infected with *H. pylori*. In certain embodiments the method is for the eradication of an *H. pylori* infection in a subject with peptic ulcer disease. It may be that the peptic ulcer disease is gastric ulcer. It may be that the peptic ulcer disease is duodenal ulcer. It may be that the method is for the treatment or prevention of bleeding in peptic ulcer disease (for example to treat or prevent bleeding of a gastric ulcer; or to treat or prevent bleeding of a duodenal ulcer).

The chronic use of non-steroidal anti-inflammatory drugs (NSAIDs) is associated with gastric toxicity, particularly peptic ulcer disease, corpus gastritis and gastric atrophy. The undesirable side-effects of NSAIDs are amplified in subjects infected with *H. pylori*. (Maastricht IV/Florence Consensus Report, Gut 2012: 61, 646-664). Accordingly, treatment of subjects with an orally administered halogenated salicylanilide using the methods of treatment described herein to eradicate an *H. pylori* infection is expected to be beneficial in the treatment or prevention of peptic ulcer disease in subjects that are treated with an NSAID.

In certain embodiments the method of treatment is for the prevention or treatment of peptic ulcer disease (e.g. gastric or duodenal ulcers) in a subject infected with *H. pylori*, and wherein the subject is receiving NSAID therapy, the method comprising orally administering to the subject an effective amount of a halogenated salicylanilide, or a pharmaceutically acceptable salt or solvate thereof.

In certain embodiments the method of treatment is for the eradication of a *H. pylori* infection in a subject that is being treated with an NSAID, the method comprising orally administering to the subject a halogenated salicylanilide, or a pharmaceutically acceptable salt or solvate thereof. Eradication of the *H. Pylon* is expected to prevent or reduce the risk of the subject developing peptic ulcer disease.

Suitably in these embodiments the subject is receiving chronic NSAID therapy. For example the subject is treated with the NSAID for more than 1 week, 2 weeks, 3 weeks, 4 weeks, 3 months, 6 months or more than 1 year.

In certain embodiments it may be beneficial to eradicate the *H. Pylon* in the subject by oral administration of the halogenated salicylanilide before initiating NSAID therapy (particularly chronic NSAID therapy). It may be that eradication of the *H. Pylon* infection prior to initiating NSAID therapy may prevent or reduce the risk of NSAID induced bleeding of gastric or duodenal ulcers. It is also contemplated that eradication of the *H. Pylon* infection could take place concurrently with the NSAID therapy.

Subjects that have a history of peptic ulcer disease are at particular risk of recurrence of the peptic ulcer disease when chronically treated with an NSAID therapy (Maastricht IV, supra). Eradication of *H. Pylon* infection in a subject with a history of peptic ulcer disease may therefore be beneficial. Accordingly in certain embodiments there is provided a method of eradicating a *H. Pylon* infection in a subject that has had previous peptic ulcer disease, the method comprising orally administering to the subject an effective amount of a halogenated salicylanilide, or a pharmaceutically acceptable salt or solvate thereof. The method may further comprise treating the subject with an NSAID therapy (suitably as a chronic therapy) after the *H. Pylon* infection has been eradicated.

Also contemplated is testing a subject that is being treated with chronic NSAID therapy for the presence of an *H. Pylon* infection and when an infection is identified orally administering to the subject an effective amount of a halogenated salicylanilide, or a pharmaceutically acceptable salt or solvate thereof to eradicate the *H. Pylon* infection. Suitable methods for testing for and diagnosing an *H. Pylon* infection are well known, including the methods described herein.

In the embodiments above relating to NSAID therapy, the subject may be treated concurrently with a PPI (e.g. a PPI as described herein, such as omeprazole or pantoprazole) and the NSAID. In certain embodiments the subject is treated by oral administration of the halogenated salicylanilide to eradicate a *H. Pylon* infection before commencing combined PPI and NSAID therapy.

NSAID inhibition of COX-1 in the gastrointestinal tract leads to a reduction of prostaglandin secretion resulting in damage to gastric mucosa. Inhibition of COX-2 may also play a role in mucosal injury, although this is thought to be less problematic than COX-1 inhibition. Thus in certain embodiments the NSAID may be non-selective COX-2 inhibitor or a selective COX-2 inhibitor. Examples of NSAIDs include a compound selected from: diclofenac, meloxicam, ketoprofen, etodolac, fenoprofen, flurbiprofen, mefenamic acid, nabumetone, oxaprozin, piroxicam, sulindac, tolmetin, naproxen, indomethacin and diflunisal, iroxicam, ketorolac, aceclofenac, ibuprofen, aspirin and celecoxib. In some embodiments the NSAID is a non-selective NSAID selected from Diclofenac, meloxicam, ketoprofen, naproxen, indomethacin and diflunisal. In some embodiments the NSAID is selected from naproxen, indomethacin and diflunisal. In some embodiments the NSAID is aspirin.

In some embodiments the NSAID is not a COX-2 selective NSAID, for example, the NSAID is not celecoxib.

Gastric Cancer

*H. pylori* infection is a strongly associated with the development of gastric cancer and the World Health Organisation (WHO) has classified *H. pylori* as a class I gastric carcinogen (Peek et al supra.).

In certain embodiments there is provided a method for the treatment or prevention of gastric cancer in a subject infected with *H. pylori*, the method comprising orally administering to the subject an effective amount of a halogenated salicylanilide, or a pharmaceutically acceptable salt or solvate thereof.

Gastric carcinogenesis is reversible at the early stages and eradication of *H. pylori* infections before gastric damage induced by the *H. pylori* has become malignant may prevent or reduce the risk of a subject developing gastric cancer. In certain embodiments there is provided a method of preventing or reducing the risk of a *H. pylori* infected subject developing gastric cancer, the method comprising orally administering to the subject an effective amount of a halogenated salicylanilide, or a pharmaceutically acceptable salt or solvate thereof.

Treatment of *H. pylori* induced premalignant lesions in the gastric mucosa is important to prevent carcinogenesis of the lesion and the emergence of gastric cancer.

The early stages of *H. pylori* infection induce gastritis and mucosal damage. Corpus gastritis and the development of atrophic gastritis are particular risk factors for the development of *H. pylori* induced gastric cancer. Subjects with severe atrophic gastritis (with or without intestinal metaplasia) in the corpus or with severe corpus predominant gastritis are those at highest risk for progression to gastric cancer (Correa. Gastroenterol. Clin. North Am. 2013; 42:211-17).

The chronic inflammation induced by the *H. pylori* also results in the development of gastric epithelial dysplasia, a premalignant lesion. Once a gastric neoplasm becomes malignant, subsequent eradication of *H. pylori* infection is less likely to be effective in treating or inhibiting progression of the cancer.

Accordingly, in certain embodiments there is provided a method for treating a premalignant gastric epithelial lesion in a subject infected with *H. pylori*, the method comprising orally administering to the subject an effective amount of a halogenated salicylanilide, or a pharmaceutically acceptable salt or solvate thereof.

In certain embodiments there is provided a method for eradicating a *H. pylori* infection in a subject that has a premalignant gastric epithelial lesion, the method comprising orally administering to the subject an effective amount of a halogenated salicylanilide, or a pharmaceutically acceptable salt or solvate thereof.

It may be that the premalignant gastric epithelial lesion is gastric epithelial dysplasia, for example a high-grade gastric epithelial dysplasia. The grading of dysplasia may be determined according to known methods, for example according to the WHO classification (Yakirevich et al. Gastroenterol. Clin. North Am. 2013 June; 42(2):261-84).

It may be that the premalignant gastric epithelial lesion is gastric epithelial hyperplasia.

It has been shown that subjects infected with *H. pylori* that have undergone resection of a premalignant gastric lesion are at a high risk of developing metachronous gastric lesions, including gastric cancer. Eradication of *H. pylori* can prevent or reduce the risk of developing metachronous gastric lesions.

In certain embodiments there is provided a method for eradicating an *H. pylori* infection in a subject, wherein the subject has undergone resection of a premalignant gastric lesion (e.g. gastric epithelial dysplasia), the method comprising orally administering to the subject an effective amount of a halogenated salicylanilide, or a pharmaceutically acceptable salt or solvate thereof.

In certain embodiments there is provided a method for preventing or reducing the risk of metachronous gastric lesions in a subject that has undergone resection of a premalignant gastric lesion (e.g. gastric epithelial dysplasia) and wherein the subject is infected by *H. pylori*, the method comprising orally administering to the subject an effective amount of a halogenated salicylanilide, or a pharmaceutically acceptable salt or solvate thereof.

Studies have demonstrated that *H. pylori* eradication can reduce the development of metachronous gastric cancer after endoscopic resection of early gastric cancer (EGC) (Uemura et al. Cancer Epidemiol Biomarkers Prev. 1997 August; 6(8):639-42). Metachronous cancer refers to a multiple primary tumours developing at intervals, for example the development of a second gastric neoplasm following resection of a primary gastric neoplasm.

Accordingly, the method may be for use in the eradication of an *H. pylori* infection in a subject after resection (e.g. endoscopic resection) of EGC, the method comprising the method comprising orally administering to the subject an effective amount of a halogenated salicylanilide, or a pharmaceutically acceptable salt or solvate thereof.

In certain embodiments there is provided a method for preventing or reducing the risk of metachronous gastric in a subject that has undergone resection (e.g. endoscopic resection) of EGC and wherein the subject is infected with *H. pylori*, the method comprising orally administering to the subject an effective amount of a halogenated salicylanilide, or a pharmaceutically acceptable salt or solvate thereof.

Early gastric cancer includes, for example, gastric cancer limited to the gastric mucosa and/or submucosa.

Pre-cancerous gastric epithelial lesions and early gastric cancer can be diagnosed using known methods, for example endoscopy including white light endoscopy, magnification chromoendoscopy and/or narrow-band imaging endoscopy.

The strong link between *H. pylori* and gastric cancer and the evidence indicating that eradication of the infection early is important to prevent oncogenesis and the development of gastric cancer, may warrant prophylactic treatment of subjects to prevent or reduce the risk of developing gastric cancer. So called "test and treat" methods have been proposed wherein a subject is tested for the presence of *H. pylori* and the subject is treated to eradicate the infection without any further diagnosis of the gastric damage and inflammation caused by the *H. pylori* bacteria.

Accordingly, in some embodiments there is provided a method for the prophylactic treatment or prevention of gastric cancer in a subject, the method comprising testing the subject for the presence of a *H. pylori* infection and if an infection is detected orally administering to the subject an effective amount of a halogenated salicylanilide, or a pharmaceutically acceptable salt or solvate thereof.

In some embodiments there is provided a method for the prophylactic treatment or prevention of gastric cancer in a subject that has a *H. pylori* infection, the method comprising orally administering to the subject an effective amount of a halogenated salicylanilide, or a pharmaceutically acceptable salt or solvate thereof.

The methods for the treatment or prevention of gastric cancer described herein a particularly suitable for use in the treatment of subjects that are at a high risk of developing gastric cancer. High risk factors include subjects with one or more of the following characteristics:
- first-degree relatives of family members with a diagnosis of gastric cancer;
- previous gastric neoplasia treated by resection;
- gastritis, including severe pan-gastritis, corpus-predominant gastritis, or severe atrophy;
- subjects with chronic gastric acid inhibition for more than 1 year;
- subjects with environmental risk factors for gastric cancer (e.g. heavy smoking, high exposure to dust, coal, quartz and/or cement)

Mucosal-Associated-Lymphoid-Type (MALT) Lymphoma

Mucosal-associated-lymphoid-type (MALT) lymphoma is a non-Hodgkin lymphoma which originates from B cells in the marginal zone of the MALT. MALT lymphoma is most common in the stomach. There is strong evidence that gastric MALT lymphoma is caused by *H. pylori* (Pereira et al. World J Gastroenterol. 2014 Jan. 21; 20(3):684-98).

Accordingly, in certain embodiments there is provided a method for the treatment or prevention of gastric MALT lymphoma in a subject infected by *H. pylori*, the method comprising orally administering to the subject an effective amount of a halogenated salicylanilide, or a pharmaceutically acceptable salt or solvate thereof.

Colorectal Cancer

*H. pylori* may be associated with the development of colorectal cancer and has been implicated in colorectal carcinogenesis. Although there are some doubts that *H. pylori* has a direct causal link to colorectal cancer there is evidence that it is associated with potentially oncogenic interactions that could result in the development of colorectal cancer, including induction of inflammation of the colonic mucosa and the release of toxins (Papastergiou et al. World J Gastroenterol. 2016; 22(2):649-58).

In certain embodiments there is provided a method for the treatment or prevention of colorectal carcinoma in a subject infected with *H. pylori*, the method comprising orally administering to the subject an effective amount of a halogenated salicylanilide, or a pharmaceutically acceptable salt or solvate thereof.

In certain embodiments there is provided the eradication of a *H. pylori* infection in a subject with colorectal carcinoma, the method comprising orally administering to the subject an effective amount of a halogenated salicylanilide, or a pharmaceutically acceptable salt or solvate thereof.

Suitably the subject is treated to eradicate a *H. pylori* infection before the subject has developed colorectal cancer. For example treating subjects with premalignant lesions in colorectal tissue to eradicate *H. pylori* may be effective in preventing the oncogenesis of the lesion to a malignant tumour.

In certain embodiments there is provided a method for the treatment of a premalignant colorectal lesion in a subject infected with *H. pylori*, the method comprising orally administering to the subject an effective amount of a halogenated salicylanilide, or a pharmaceutically acceptable salt or solvate thereof.

In certain embodiments there is provided a method for the eradication of a *H. pylori* infection in a subject with a premalignant colorectal lesion, the method comprising orally administering to the subject an effective amount of a halogenated salicylanilide, or a pharmaceutically acceptable salt or solvate thereof.

There is some evidence suggesting that the risk of developing colorectal cancer is higher in subjects that have *H. pylori* induced gastritis (e.g. atrophic gastritis) and/or premalignant gastric lesions (e.g. gastric epithelial dysplasia).

Accordingly in some embodiments there is provided a method for the treatment of a premalignant colorectal lesion in a subject infected with *H. pylori*, wherein the subject has gastritis (e.g. atrophic gastritis) and/or premalignant gastric lesions (e.g. gastric epithelial dysplasia), the method comprising orally administering to the subject an effective amount of a halogenated salicylanilide, or a pharmaceutically acceptable salt or solvate thereof.

In certain embodiments there is provided a method for the eradication of a *H. pylori* infection in a subject with a premalignant colorectal lesion, wherein the subject has gastritis (e.g. atrophic gastritis) and/or premalignant gastric lesions (e.g. gastric epithelial dysplasia), the method comprising orally administering to the subject an effective amount of a halogenated salicylanilide, or a pharmaceutically acceptable salt or solvate thereof.

In these embodiments it may be that the premalignant colorectal lesion is a neoplastic polyp (e.g. tubular and/or villous adenomas).

Extra-Gastric Diseases

*H. pylori* infection is associated with certain extra-gastric medical conditions, particularly iron-deficiency anaemia, idiopathic thrombocytopenic purpura and vitamin B12 deficiency (Maastricht Guidelines, supra).

In certain embodiments there is provided a method for the treatment or prevention of an extra-gastric medical condition associated with *H. pylori* in a subject infected with H. pylori, the method comprising orally administering to the subject an effective amount of a halogenated salicylanilide, or a pharmaceutically acceptable salt or solvate thereof. It may be that the extra-gastric condition is selected from: iron-deficiency anaemia, idiopathic thrombocytopenic purpura and vitamin B12 deficiency.

It is to be understood that the disease or infections caused by or associated with *H. pylori* described above and herein may be treated using any of the methods disclosed herein. For example, the method could be oral administration of the halogenated salicylanilide alone of concurrently with a PPI inhibitor or a nitroimidazole antibiotic (e.g. metronidazole).

Diagnosis of *H. pylori* Infection

The presence of a *H. pylori* infection in the subject may be determined using well known diagnostic methods. Diagnosis may be via a direct or indirect diagnostic methods. Suitable direct testing methods include test carried out on a biopsy or by indirect methods. Examples of suitable diagnostic methods include those set out in Wang et al. World journal of gastroenterology vol. 21, 40 (2015):11221-35.

Direct testing for *H. pylori* is generally performed using endoscopic methods to obtain a biopsy sample of gastric mucosal tissue and analysis of the sample for evidence of *H. pylori* infection. This can be achieved using for example histology methods, culturing of the sample, rapid urease test or PCR methods.

The rapid urease test relies upon secretion of urease enzymes from the *H. pylori* bacteria. A biopsy sample is cultured in a medium containing urea. The urease produced by the bacteria hydrolyses the urea to ammonia, which can be detected in the medium, typically by detecting the increase in pH resulting from the ammonia (Uotani et al. *Ann Transl Med.* 2015; 3(1):9).

When histological methods are used it is recommended that PPI therapy is stopped for at least 2 weeks prior to obtaining endoscopic samples to minimise the risk of erroneous diagnosis (Malfertheiner et al. Gut. 2012 May; 61(5): 646-64).

Culturing methods to detect *H. pylori* can also be used to assess the susceptibility of particular *H. pylori* to antibiotic treatment. In certain embodiments of the methods described herein it may be that the *H. pylori* infecting the subject are tested for susceptibility to the halogenated salicylanilide prior to orally administering the halogenated salicylanilide. This will further reduce the likelihood of *H. pylori* resistance to the halogenated salicylanilide emerging.

PCR methods to detect *H. pylori* can also be used on other biological samples, including saliva, gastric fluid and stool samples.

Indirect testing does not require a biopsy sample and as such may be preferred, because it uses non-invasive methods. Suitable indirect methods include the urea breath test, the stool antigen test and serology. The most common indirect method used is the urea breath test (UBT), which utilises the urease enzyme produced by the *H. pylori* to detect infection. A subject ingests $^{13}C$ or $^{14}C$-labeled urea which is hydrolysed to labelled $CO_2$ in the stomach by the *H. pylori* urease. The labelled $CO_2$ is absorbed into the blood and is exhaled. The exhaled labelled $CO_2$ can then be detected, thereby identifying an *H. pylori* infection. The UBT has been shown to be a very accurate test for *H. pylori* infection (Ferwana et al. World J. Gastroenterol. 2015 Jan. 28; 21(4):1305-14).

In the stool antigen test (SAT), detection of *H. pylori* antigen in the stool sample is used to diagnose infection. It is recommended that ELISA is used to detect the *H. pylori* antigen (Maastricht Consensus Report, supra).

Serology is also a suitable non-invasive method for the detection of *H. pylori*. The presence of serum IgG to *H. pylori* may be detected using known methods, preferably ELISA.

In some embodiments the subject is tested for the presence of a *H. pylori* infection and when an infection is detected the subject is treated with the halogenated salicylanilide in accordance with any of the methods described herein. The subject may be tested for the presence of an *H. pylori* infection using any known method, including the invasive and non-invasive methods described herein.

In some embodiments it may be that *H. pylori* isolated from the subject (e.g. following biopsy) are cultured and then tested for susceptibility to the halogenated salicylanilide prior to initiating treatment of the subject with the halogenated salicylanilide.

In some embodiments the subject is tested for the presence of *H. pylori* after completing a method of treatment described herein. Such post-treatment testing may be important to confirm that the treatment has been effective against the *H. pylori* infection. For example to confirm that the treatment has completely eradicated the *H. pylori* infection. Suitably the subject is tested at least 28 days, preferably 28 to 56 days following the last dose of the halogenated salicylanilide administered to the subject. This minimises the risk of "false negative" results, because the treatment-free period prior to testing is generally sufficient time for the *H. pylori* infection to re-establish itself in the event that the treatment does not completely eradicate the *H. pylori*.

Halogenated Salicylanilide

The halogenated salicylanilide may be of the formula (I), or a pharmaceutically acceptable salt or solvate thereof:

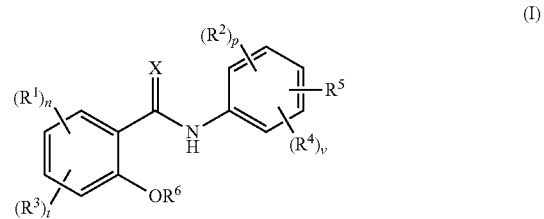

(I)

wherein, X, $R^1$, $R^2$, $R^3$, $R^4$, $R^5$, $R^6$, n, p, t and v are as hereinbefore defined.

The following statements in the numbered paragraphs below apply to compounds of the formulae (I) or (II). These statements are independent and interchangeable. In other words, any of the features described in any one of the following statements may (where chemically allowable) be combined with the features described in one or more other statements below. In particular, where a compound is exemplified or illustrated in this specification, any two or more of the statements below which describe a feature of that compound, expressed at any level of generality, may be combined so as to represent subject matter which is contemplated as forming part of the disclosure of this invention in this specification.

1. X is O.
2. $R^1$ and $R^2$ are at each occurrence independently selected from fluoro, chloro, bromo and iodo.
3. $R^1$ and $R^2$ are at each occurrence independently selected from chloro, bromo and iodo.
4. $R^1$ is chloro.
5. $R^1$ is bromo.
6. $R^1$ is iodo.
7. $R^2$ is chloro.
8. $R^2$ is bromo.
9. $R^2$ is iodo.
10. $R^3$ and $R^4$ are at each occurrence independently selected from H, $C_{1-4}$ alkyl, —$OR^{41}$, —$NO_2$ and —CN.
11. $R^3$ and $R^4$ are at each occurrence independently selected from H, $C_{1-4}$ alkyl, —$OR^{41}$ and —$NO_2$.
12. $R^3$ and $R^4$ are at each occurrence independently selected from H, $C_{1-4}$ alkyl, —OH, —OMe, —$NO_2$ and —CN, for example H, $C_{1-4}$ alkyl, —OH or —$NO_2$.
13. $R^5$ is H.
14. $R^5$ is -$L^1$-$R^7$.
15. $L^1$ is selected from —O—, —$CH_2$— and —CH(CN)—, for example —O— or —CH(CN)—.
16. $R^7$ is phenyl, unsubstituted or substituted with 1, 2, or 3 groups selected from halo, $C_{1-4}$ alkyl and —CN
17. $R^7$ is phenyl unsubstituted or substituted with 1, 2, or 3 groups (for example 1 or 2 groups) selected from halo.
18. $R^7$ is unsubstituted phenyl.
19. $L^1$ is selected from —O— and —CH(CN)—; and $R^7$ is phenyl unsubstituted or substituted with 1, 2, or 3 groups selected from halo.
20. $R^6$ is H.
21. $R^6$ is —$C(O)R^{42}$, for example —$C(O)CH_3$.
22. t=0 or 1.
23. t=0.
24. v=0 or 1.
25. v=0.
26. o is 1.
27. v=1 and $R^4$ is selected from —OH, $C_{1-4}$alkyl and —$NO_2$.
28. A compound of any of formulae (I) or (II), or a pharmaceutically acceptable salt thereof.

Particular compounds are compounds of formula (I) or formula (II), or a pharmaceutically acceptable salt or solvate thereof wherein:

X is O;

$R^1$ and $R^2$ are at each occurrence independently selected from halo;

$R^3$ and $R^4$ are at each occurrence independently selected from H, $C_{1-4}$ alkyl, —$OR^{41}$, —$NO_2$ and CN;

$R^5$ is H or -$L^1$-$R^7$;

$R^6$ is H or —$C(O)R^{42}$;

$L^1$ is selected from 0 and —CH(CN)—;

$R^7$ is phenyl unsubstituted or substituted with 1, 2, or 3 groups selected from halo;

$R^{41}$ and $R^{42}$ are at each occurrence independently selected from H and $C_{1-4}$ alkyl;

n and p are each independently selected from 0, 1, 2, 3 or 4, with the proviso that n+p is at least 1;

t and v are independently selected from 0, 1 and 2.

or a pharmaceutically acceptable salt, or solvate thereof.

The halogenated salicylanilide may be selected from:

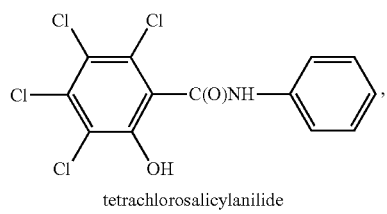
tetrachlorosalicylanilide

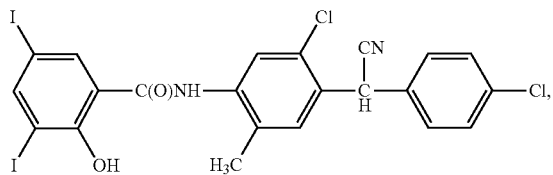
closantel

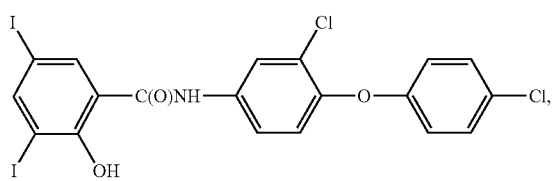
rafoxanide

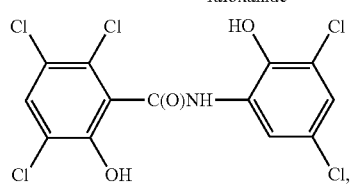
oxyclosanide

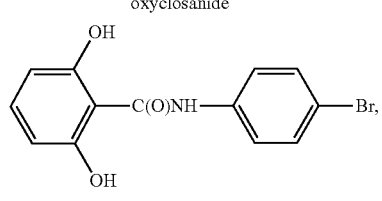
resorantel

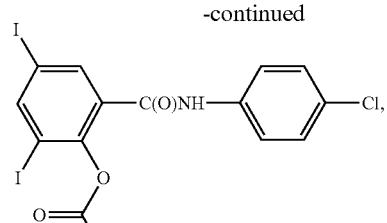
clioxanide

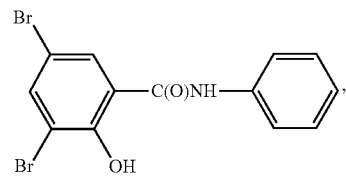
dibromosalan

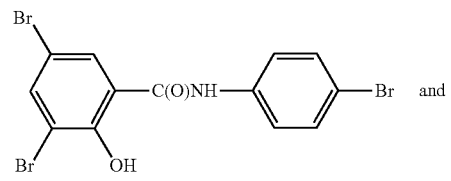
tribromosalan

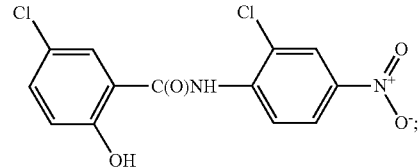
niclosamide or a pharmaceutically acceptable salt or solvate thereof.

The halogenated salicylanilide may be selected from the group consisting of niclosamide, closantel, oxyclozanide, rafoxanide, or a pharmaceutically acceptable salt or solvate thereof.

The halogenated salicylanilide may be selected from oxyclozanide and niclosamide, or a pharmaceutically acceptable salt or solvate thereof.

The halogenated salicylanilide may be closantel, or a pharmaceutically acceptable salt or solvate thereof, e.g. the halogenated salicylanilide is closantel.

The halogenated salicylanilide may be rafoxanide, or a pharmaceutically acceptable salt or solvate thereof, e.g. the halogenated salicylanilide is rafoxanide.

The halogenated salicylanilide may be oxyclozanide.

The halogenated salicylanilide may be niclosamide, or a pharmaceutically acceptable salt or solvate thereof.

In certain embodiments the halogenated salicylanilide is niclosamide.

It is to be understood that any of the halogenated salicylanilides, in particular oxyclozanide, niclosamide, rafoxanide, or closantel, or a pharmaceutically acceptable salt or solvate thereof, described in this section or elsewhere in the application may be used in any of the treatments described herein.

Synthesis

The halogenated salicylanilides described herein are known or can be synthesised using known methods. For example, compounds of the formula (I) herein may be prepared by coupling an amine of the formula (II) with an acid of formula (III) (or an activated for of the acid, e.g. an acyl halide):

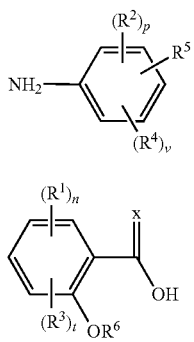

(II)

(III)

Necessary starting materials are known or can be prepared using standard procedures of organic chemistry.

Bacterial Efflux Pump Inhibitor

As mentioned above, WO 2016/080846 discloses certain salicylamide compounds and at least one efflux pump inhibitor for treatment of an infection caused by Gram negative bacteria. WO 2016/080846 discloses the following classes of efflux pump compounds:

alkoxyquinoline derivatives, e.g. 2,8-dimethyl-4-(2'-pyrrolidinoethyl)-oxyquinoline;
piperidine and piperidine analogues;
phenothiazines, e.g. chloropromazine;
monoterpene derivatives, e.g. geranylamine; and
arginine derivatives (see U.S. Pat. No. 6,251,869);

The following compounds are disclosed in WO 2016/080846 as examples of bacterial efflux pump inhibitors: (2R,4S)-4-(2-aminoacetamido)-N-[(1R-)-3-phenyl-1-(3-quinolylcarbamoyl)propyl]-2-pyrrolidinecarboxamide; (2R, 4S)-4-(2-aminoacetamido)-N-[(1R)-3-phenyl-1-(3-phenyl) propylcarbamoyl] propyl]-2-pyrrolidinecarboxamide; (2S, 4R)-4-(2-aminoacetamido)-N-[(1R)-3-phenyl-1-(3-quinolylcarbamoyl)propyl]-2-pyrrolidinecarboxamide; (2S, 4R)-4-(2-aminopropionamido]-N-[(1R)-3-phenyl-1-(3-quinolylcarbamoyl)propyl]-2-pyrrolidinecarboxamide; (2S, 4R)-4-(aminompropionamido)-N-[(1R)-3-phenyl-1-(3-quinolylcarbamolyl)propyl]-2-pyrrolidinecarboxamide; (2S, 4R)-4-[3-(aminopropionamidop-N—R1R)-3-phenyl-1-(3-quinolylcarbamoyl)propyl]-2-pyrrolidinecarboxamide; (2S, 4R)-4-(amino-N-[(1R)-3-phenyl-(3-quinolylcarbamoyl) propyl]-2-pyrrolidinecarboxamide; (2S,4R)-4-(aminoacetamido)-N-[(1R)-3-methyl-1-[(3-quinolylcarbamoyl) butyl]-2-pyrrolidinecarboxamide; (2S,4R)-4-(2-amino-N-methylacetamido)-N-[(1R)-3-phenyl-1-(3-quinolylcarbamoyl)propyl]-2-pyrrolidinecarboxamide; (2S,4R)-4-(2-aminoacetamido)-N-[(1R)-3-3-methyl-1-(6-methoxy-8-methyl-3-quinolylcarbamoyl)butyl]-2-pyrrolidinecarboxamide; (2S,4R)-4-(2-aminoacetamido)-N-[(1R)-3-phenyl-1-(6,7-dimethyl-3-quinolylcarbamoyl)propyl]-2-pyrrolidinecarboxamide; (2S,4R)-4-(2-aminoacetamido)-N-[(1R)-2-(4-methoxyphenyl)-1-(3-quinolylcarbamoyl)ethyl]-2-pyrrolidinecarboxamide; (2R,4R)-4-(aminomethyl)-N-[(1R)-3-methyl-1-quinoylcarbamoyl)bulyl]-2-pyrrolidinecarboxamide; (2R,4R)-4-aminomethyl)-N-[(1R)-3-phenyl-1-(6-ethyl-3-quinolylcarbamoyl)propyl]-2-pyrrolidinecarboxamide; (2S,4R)-4-(2-aminoacetamido)-N-methyl-N-[(1R)-3-phenyl-1-(3-quinolylcarbamoyl)propyl]-2-pyrrolidinecarboxamide; (2R,4R)-4-(aminomethyl)-N-[(1R)-3-phenyl-1-(3-quinolylcarbamoyl)propyl]-2-pyrrolidinecarboxamide; (2R,4R)-4-(2-aminoacetamido)-N-[(1R)-3-phenyl-1-(3-quinolylcarbamoyl)propyl]-2-pyrrolidinecarboxamide; (2S,4R)-4-(2-aminoacetamido)-N-[(1R)-3-phenyl-1-(6-ethyl-3-quinolylcarbamoyl)propyl]-2-pyrrolidinecarboxamide; (2S,4R)-4-(2-aminoacetamido)-N-[(1R)-3-methyl-1-(6-ethyl-3-quinolylcarbamoyl)butyl]-2-pyrrolidinecarboxamide; (2R,4R)-4-(2-aminoacetamido)-N-[(1R)-2-(4-fluorophenyl)-1-(3-quinolylcarbamoyl)ethyl]-2-pyrrolidinecarboxamide; (2S,4R)-4-(2-aminoacetamido)-N-[(1R)-2-(4-fluorophenyl-(3-quinolylcarbamoyl)ethyl]-2-pyrrolidinecarboxamide; (2S,4R)-1-(2-aminoacetamido)-N-[(1R)-3-phenyl-1-(6-methoxy-8-methyl-3-quinolylcarbamoyl) propyl]2-pyrrolidinecarboxamide; (2S,4R)-4-(2-aminoacetamido)-N-[1R)-2-(4-hydroxyphenyl)-1-(3-quinolylcarbamoyl)ethyl]-2-pyrrolidinecarboxamide; (2S,4S)-4-(aminomethyl)-N-[(1R)-3-phenyl-1-(3-quinolylcarbamoyl)propyl]-2-pyrrolidinecarboxamide; (2R,4R)-4-(aminomethyl)-N-[(1R)-2-(4-hydroxyphenyl)-1-(6-ethyl-3-quinolylcarbamoyl)ethyl]-2-pyrrolidinecarboxamide; (2S,4R)-4-(2-aminoacetamido)-N-[(1R)-3-phenyl-1-(5-chloro-2-hydroxyphenylcarbamoyl)propyl]-2-pyrrolidinecarboxamide; (2S,4R)-4-(2-aminoacetamido)-N-[(1R)-3-phenyl-1-(4,5-dimethyl-2-hydroxyphenylcarbamoyl)propyl]-2-pyrrolidinecarboxamide; (2S,4R)-4-(2-aminoacetamido)-N-[(1R)-3-phenyl-1-(2-hydroxy-5-methylphenylcarbamoyl)propyl]-2-pyrrolidinecarboxamide; (2R,4R)-4-(aminomethyl)-N-[(1R)-3-phenyl-1-(6-quinolylcarbamoyl)propyl]-2-pyrrolidinecarboxamide; (2R,4R)-4-(aminomethyl)-N-[(1R)-3-phenyl-1-(8-quinolylcarbamoy propyl]-2-pyrrolidinecarboxamide; (2R,4R)-4-(aminomethyl)-N-[(1R)-2-(4-fluorophney)-1-(3-quinolylcarbamoyl)ethyl]-2-pyrrolidinecarboxamide; (2R,4R)-4-(aminomethyl)-N-[(1R)-3-phenyl-1-[3-quinolylmethyl)carbamoyl]propyl]-2-pyrrolidinecarboxamide; (2R,4R)-4-(aminomethyl)-N-methyl-N-[(1R)-3-phenyl-1-(3-quinolylcarbamoyl)propyl]-2-pyrrolidinecarboxamide; (2R,4R)-4-(aminomethyl)-N-[(1R)-3-methyl-1-(3-quinolylcarbamoly)butyl]-2-pyrrolidinecarboxamide; (2R,4R)-4-(aminomethyl)-N-[(1R)-3-phenyl-1-(6-fluoro-3-quinolylcarbamoyl)propyl]-2-pyrrolidinecarboxamide; (2R,4R)-4-(aminomethyl)-N-[(1R)-4-rnethyl-1-(3-quinolylcarbamoyl)pentyl]-2-pyrrolidinecarboxamide; (2R,4R)-4-(aminomethyl)-N-[(1R)-3-phenyl-1-(5-fluoro-2-hydroxyphenylcarbamoyl) propyl]-2-pyrrolidinecarboxamide; (2R,4R)-4-(aminomethyl)-N-[(1R)-3-phenyl-1-(2-hydroxy-5-methylphenylcarbamoyl)propyl]-2-pyrrolidinecarboxamide; (2R,4R)-4-(aminomethyl)-N-[(1R)-3-phenyl-1-(5-chloro-2-hydroxyphenylcarbamoyl)propyl]-2-pyrrolidinecarboxamide; (2R, 4R)-4-(aminomethyl)-N-methyl-N-[(1R)-3-methyl-1-(6-ethyl-3-quinolylcarbamoyl)butyl]-2-pyrrolidinecarboxamide; (2R,4S)-4-(2-aminoacetamido)-N-(2-phenylethyl)-N-(3-quinolylcarbamoyl)ethyl]-2-pyrrolidinecarboxamide; (2R,4S)-4-[(2R)-2-aminopropionamido]-N-(2-phenylethyl)-N-(3-quinolylcarbamoyl)ethyl]-2-pyrrolidinecarboxamide; (2S,4R)-4-(2-aminoacetamido)-N-(2-phenylethyl)-N-(3-quinolylcarbamoyl)ethyl]-2-pyrrolidinecarboxamide; (2R,4S)-4-(2-aminoacetamido)-N-(2-methylpropyl)-N-(7-ethyl-3-quinolylcarbamoyl)ethyl]-2-pyrrolidinecarboxamide; (2R,4R)-4-(aminomethyl)-N-(2-phenylethyl)-N-(3-quinolylcarbamoyl)ethyl]-2-pyrrolidinecarboxamide; (2R,4R)-4-(2-aminoacetamido)-N-(2-phenylethyl)-N-(3-quinolylcarbamoyl)methyl]-2-pyrrolidinecarboxamide; (2R,4S)-4-[(2R)-2-aminopropionamido]-N-(3,3-dimethylbutyl)-N-(3-quinolylcarbamoyl)methyl]-2-pyrrolidinecarboxamide; (2R, 4R)-4-(aminomethyl)-N-[(1R)-3-phenyl-1-[(2-quinolyloxy) methyl]propyl]-2-pyrrolidinecarboxamide; (2R,4S)-4-(2-aminoacetamido)-N-[(1R)-3-methyl-1-[(2-naphthyloxy)

methyl]butyl]-2-pyrrolidinecarboxamide; (2S,4R)-4-(2-aminoacetamido)-N-[(1R)-3-phenyl-1-[(4-chlorophenylthio)methyl]propyl]-2-pyrrolidinecarboxamide; (2S,4R)-4-[(2R)-2-aminopropionamido]-N-[(1R)-3-phenyl-1-[(4-chlorophenylthio)methyl]propyl]-2-pyrrolidinecarboxamide; (2R,4S)-4-[(2R)-2-aminopropionamido]-N-[(1R)-3-phenyl-1-[(4-chlorophenylthio)methyl]propyl]-2-pyrrolidinecarboxamide; (2S,4R)-4-(2-aminoacetamido)-N-[(1R)-3-phenyl-1-[(3-quinolylthio)methyl]propyl]-2-pyrrolidinecarboxamide; (2S,4R)-4-(2-aminoacetamido)-N-[(1R)-3-phenyl-1-[(quinolyloxy)methyl]propyl]-2-pyrrolidinecarboxamide; (2S,4R)-4-(2-aminoacetamido)-N-[(1R)-3-phenyl-1-[(2-quinolylthio)methyl]propyl]-2-pyrrolidinecarobxamide; (2S,4R)-4-(2-aminoacetamido)-N-[(1R)-3-phenyl-1-(phenylthiomethyl)propyl]-2-pyrrolidinecarboxamide; (2S,4R)-4-(2-aminoacetamido)-N-[(1R)-3-phenyl-1-[(4-fluorophenylthio)methyl]propyl]-2-pyrrolidinecarboxamide; (2S,4R)-4-(2-aminoacetamido)-N-[(1R)-3-methyl-1-[(2-quinolyloxy)methyl]butyl]-2-pyrrolidinecarboxamide; (2R,4R)-4-(aminomethyl)-N-[(1R)-3-methyl-1-[(3-quinolyloxy)methyl]butyl]-2-pyrrolidinecarboxamide; (2S,4R)-4-(2-aminoacetamido)-N-[(1R)-3-methyl-1-[(4-chlorophenylthio)methyl]butyl]-2-pyrrolidinecarboxamide; (2R,4R)-4-(aminomethyl)-N-[(1R)-3-methyl-1-[(4-chlorophenylthio)methyl]butyl]-2-pyrrolidinecarboxamide; (2R,4R)-4-(aminomethyl)-N-[(2S)-2-(6-methyl-3-quinolylcarboxamido)-4-phenylbutyl]-2-pyrrolidinecarboxamide; (2R,4R)-4-(aminomethyl)-N-[(1R)-3-phenyl-1-[(6-methyl-3-quinolylcarboxamido)methyl]propyl]-2-pyrrolidinecarboxamide; (2S,4R)-4-(2-aminoacetamido)-N-[(1R)-1-[(RS)-(5,6-dimethyl-2-benzoxazolyl)hydroxymethyl]-3-phenylpropyl]-2-pyrrolidinecarboxamide; (2S,4R)-4-[(2R)-2-aminopropionamido]-N-[(1R)-1-[(RS)-(5,6-dimethyl-2-benzoxazolyl)hydroxymethyl]-3-phenylpropyl]-2-pyrrolidinecarboxamide; (2R,4S)-4-[(2R)-2-aminopropionamido]-N-[(1R)-1-[(RS)-(5,6-dimethyl-2-benzoxazolyl)hydroxymethyl]-3-phenylpropyl]-2-pyrrolidinecarboxamide; (2S,4R)-4-(2-aminoacetamido)-N-[(1R)-1-[5,6-dimethyl-2-benzoxazolyl)hydroxymethyl]-3-phenylpropyl]-2-pyrrolidinecarboxamide; (2R,4R)-4-(aminomethyl)-N-[(1R)-1-[(RS)-(5-1,1-dimethyl)ethyl-2-benzoxazolyl)hydroxymethyl]-3-phenylpropyl]-2-pyrrolidinecarboxamide; (2R,4R)-4-(aminomethyl)-2-[((1S)-3-phenyl-1-(3-quinolylcarbamoyl)propyl)oxymethyl]-pyrrolidine; (2R,4R)-4-(aminomethyl)-2-[((1R)-3-phenyl-1-(3-quinolylcarbamoyl)propyl)-oxymethyl]pyrrolidine; (2R,4R)-4-(aminomethyl)-2-(2-quinolyloxymethyl)pyrrolidine; (2R,4R)-4-(aminomethyl)-2-(6-methyl-3-quinolylcarboxamidomethyl)pyrrolidine; (2S,4R)-4-(2-aminoacetamido)-2-(5-benzyl-2-benzmidazolyl)pyrrolidine; (2R,4R)-4-(aminomethyl)-2-(5-benzyl-2-benzimidazolyl)pyrrolidine; (2S,4R)-4-(2-aminoacetamido)-2-(1-(2-phenyl)ethyl-2-benzimidazolyl)pyrrolidine; (2S,4R)-4-(2-aminoacetamido)-2-(1-(3-aminopropyl)-2-benzimidazolyl)pyrrolidine; (2S,4R)-4-(2-aminoacetamido)-N-[(1R)-1-(2-benzoxazolyl)-3-phenylpropyl]-2-pyrrolidinecarboxamide; (2S,4R)-4-(2-aminoacetamido-N-[(1S)-1-(2-benzimidazolyl)-3-phenylpropyl]-2-pyrrolidinecarboxamide; (2S,4R)-4-(2-aminoacetamido)-N-[(5-benzyl-2-benzimidazolyl)methyl]-2-pyrrolidinecarboxamide; (2S,4R)-4-(2-aminoacetamido)-N-[(1-(2-phenyl)ethyl-2-benzimidazolyl)methyl]-2-pyrrolidinexarboxamide; (2S,4R)-4-(2-aminoacetamido)-N-[(5-1,1-dimethyl)ethyl-2-benzimidazolyl)methyl]-2-pyrrolidinecarboxamide; (2S,4R)-4-(2-aminoacetamido)-N-[(5-(1 hydroxy-1-phenyl)methyl-2-benzimidazolyl)methyl]-2-pyrrolidinecarboxaniide; (2S,4R)-4-(2-aminoacetamido)-N-[(15)-1-(5-benzyl-2-benzimidazolyl)ethyl]-2-pyrrolidinecarboxamide; (2S,4R)-4-(2-aminoacetamido)-N-[(1R)-1-(2-benzthiazolyl)-3-phenylpropyl]-2-pyrrolidinecarboxamide; (2S,4R)-4-(2-aminoacetamido)-N-[(1S)-1-(2-benzoxazolyl)-3-phenylpropyl]-2-pyrrolidinecarboxamide; (2R,4R)-4-(aminomethyl)-N-[(5-benzyl-2-benzimidazolyl)methyl]-2-pyrrolidinecarboxamide; (2R,4S)-4-(aminomethyl)-N-[(5-benzyl-2-benzimidazolyl)methyl]-2-pyrrolidinecarboxamide; (2R,4R)-4-(aminomethyl)-N-[(5-phenyloxy-2-benzimidazolyl)methyl]-2-pyrrolidinecarboxamide; (2R,4R)-4-(aminomethyl)-N-[(5-phenyl-2-benzimidaxolyl)methyl]-2-pyrrolidinecarboxamide; (2S,4R)-4-(2-aminoethylthio)-N-[(1R)-3-phenyl-1-(3-quinolylcarbamoyl)propyl]-2-pyrrolidinecarboxamide; (2S,4R)-4-(2-aminoethyloxy)-N-[(1R)-3-phenyl-1-(3-quinolylcarbamoyl)propyl]-2-pyrrolidinecarboxamide; (2S,4R)-4-(2-aminoethyloxy)-N-(6-(1,1-dimethyl)ethyl-3-quinolyl)-2-pyrrolidinecarboxamide; (2S,4RS)-4-(3-aminopropyl)-N-[(1R)-3-phenyl-1-(3-quinolylcarbamoyl)propyl]-2-pyrrolidinecarboxamide; (2S,4R)-4-(2-aminoacetamido)-N-[5-(p-chlorophenyl)tetrahydro-3-thienyl]-2-pyrrolidinecarboxamide; (2S,4R)-4-(guanadinyl)-N-[(1R)-3-phenyl-1-(3-quinolylcarbamoyl)propyl]-2-pyrrolidinecarboxamide; (2S,4R)-4-(2-aminoacetamido)-N-[7-ethyl-3-quinolyl]-2-pyrrolidinecarboxamide; (2R,4R)-4-(aminomethyl)-N-[6-(l,l-dimethyl)ethyl-3-quinolyl]-2-pyrrolidinecarboxamide; (2S,4R)-4-(2-aminoacetamido)-N-(5-benzyl-2-hydroxyphenyl)-2-pyrrolidinecarboxamide; (2S,4R)-4-(2-aminoacetamido)-N-[4-benzyl-2-benzimidazolyl)ethyl]-2-pyrrolidinecarboxamide; (2R,4R)-4-(aminomethyl)-N-(6-ethyl-3-quinolyl)-2-pyrrolidinecarboxamide; (2R,4R)-4-(aminomethyl)-N-(5-benzyl-2-benzimidazolyl)-2-pyrrolidinecarboxamide; (2S,4R)-4-(2-aminoacetamido)-N-(5-benzyl-2-benzimidazolyl)-2-pyrrolidinecarboxamide; (2R,4R)-4-(aminomethyl)-N-[(1R)-3-phenyl-1-[(3-quinolylcarboxamido)methyl]propyl]-2-pyrrolidinecarboxamide; trans-4-glycylamino-D-prolyl-D-proline-(6-isopropyl)-3-quinolylamide; trans-4-amino-L-prolyl-trans-4-((R)-2-hydroxy-4-phenylbutyrylamino-L-proline 3-quinolylamide; trans-4-glycylamino-L-prolyl-trans-4-((R)-2-hydroxy-4-phenylbutrylamino)-L-proline 3-quinolylamide; cis-4-glycylamino-L-prolyl-trans-4-((R)-2-hydroxy-4-phenylbutyrylamino)-L-proline 3-quinolylamide; trans-4-glycylamino-D-prolyl-trans-4-((R)-2-hydroxy-4-phenylbutyrylamino)-L-proline 3-quinolylamide; trans-4-(N-methylglycylamino)-L-prolyl-trans-4-((R)-2-hydroxy-4-phenylbutyrylamino)-L-proline 3-quinolylamide; trans-4-((S)-3-amino-2-hydroxypropionylamino)-L-prolyl-trans-4-((R)-2-hydroxy-4-phenylbutyrylamino)-L-proline-3-quinolylamide; trans-4-aminomethyl-L-prolyl-trans-4-((R)-2-hydroxy-4-phenylbutyrylamino)-L-proline 3-quinolylamide; 4-(2-aminoethyl)-L-prolyl-trans-4-((R)-2-hydroxy-4-phenylbutyrylamino)-L-proline 3-quinolylamide; 1-(N-methylglycyl)-trans-4-amino-L-prolyl-trans-4-((R)-2-hydroxy-4-phenylbutyrylamino)-L-proline 3-quinolylamide; trans-4-amino-L-pipecolinoyl-trans-4-((R)-2-hydroxy-4-phenylbutyrylamino)-L-proline 3-quinolylamide; cis-4-amino-L-pipecolinoyl-trans-4-((R)-2-hydroxy-4-phenylbutyrylamino)-L-proline 3-quinolylamide; trans-4-glycylamino-L-pipecolinoyl-trans-4-((R)-2-hydroxy-4-phenylbutyrylamino)-L-proline 3-quinolylamide; cis-4-glycylamino-L-pipecolinoyol-trans-4-((R)-2-hydroxy-4-phenylbutyrylamino)-L-proline 3-quinolylamide; D-ornithyl-trans-4-(4-phenylbutanoyl)amino-L-proline-5-indanylamide; L-ornithyl-cis-4-(4-phenylbutanoyl)amino-L-proline-5-indanylamide; D-ornithyl-cis-4-(4-phenylbutanoyl)amino-L-proline 5-indanylamide; 4-hydroxy-L-ornithyl-trans-4-(4-phenylbutanoyl)amino-L-proline 5-indanylamide; trans-4-glycylamino-L-prolyl-D- homophenylalanine 3-quinolylamide; trans-4-amino-L-prolyl-D-homophenylalanine 3-quinolylamide; trans-4-glycylamino-L-prolyl-D-homophenylalanine 5-indanylamide; trans-4-glycylamino-L-prolyl-D-homophenylalanine 3,4-dimethylphenylamide; trans-4-glycylamino-L-prolyl-D-homophenylalanine 3,5-dimethylphenylamide; trans-4-glycylamino-L-prolyl-D-homophenylalanine 4-chloro-3-methylphenylamide; trans-4-glycylamino-L-prolylglycine 4-benzylphenylamide; trans-4-glyclamino-L-proline 4-phenoxyphenylamide; trans-4-glycylamino-L-proline 4-(4'-methylphenoxy)phenylamide; trans-4-glycylamino-L-proline 4-(4'-chlorophenoxy)phenylamide; trans-4-glycylamino-L-proline 4-phenylaminophenylamide; trans-4-glycylamino-L-proline 3-biphenylamide; trans-4-glycylamino-D-proline 3-biphenylamide; trans-4-glycylamino-L-proline 4-benzylphenylamide; trans-4-glycylamino-L-proline 4-tert-butylphenylamide; trans-4-glycylamino-L-proline 4-phenylbenzylamide; trans-4-glycylamino-L-proline 4-benzyloxyphenylamide; trans-4-glycylamino-L-proline 3-benzyloxyphenylamide; trans-4-glycylamino-L-proline 4-(phenylthiomethyl)phenylamide; trans-4-glycylamino-L-proline 4-benzylthiophenylamide; trans-4-((S)-3-amino-2-hydoxypropionylamino)-L-proline 4-phenoxyphenylamide; trans-4-(2-aminoethylsulfonylamino)-L-proline 4-phenoxyphenylamide; trans-4-glycylamino-L-proline 4-phenylthiazol-2-ylamide; trans-4-glycylamino-L-proline 3-(6-benzyl)quinolylamide; trans-4-amino-L-pipecolinoyl-(4-phenoxyphenyl)amide; trans-4-glycylamino-L-pipecolinoyl 4-phenoxyphenylamide; trans-4-aminomethyl-L-proline 4-phenoxyphenylamide; 1-(trans-4-glycylamino-L-prolyl)-4-(3-chlorophenyl)piperazine; 1-[trans-4-(2S)-3-amino-2-hydroxypropionylamino)-D-prolyl]-4-(3-chloro-2-methylphenyl)piperazine; 1-(N-trans-4-glycylamino-L-prolyl)-4-(4-chlorophenyl)piperazine; 1-(trans-4-glycylamino-L-prolyl)-4-(2-chlorophenyl)piperazine; 1-(trans-4-aminomethyl-L-prolyl)-4-(3-chloro-2-methylphenyl)piperazine; 1-(trans-4-glycylamino-L-prolyl)-4-(4-phenylbutanoyl)piperazine; (2R)-4-benzyl-1-(trans-4-glycylamino-D-prolyl)-2-phenethylpiperazine; 1-(trans-4-glycylamino-L-prolyl)-4-(4-benzyloxyphenoxy)piperidine; 1-(trans-4-glycylamino-L-prolyl)-4-(3,5-dichlorophenoxy)piperidine; 1-(trans-4-glycylamino-D-prolyl)-4-(3,5-dichlorophenoxy)piperidine; trans-4-glycylamino-L-prolyl-4-(2-chloro-5-methylphenoxy)piperidine; (2S,4R)-4-glycylamino-2-(4-biphenyloxy)methylpyrrolidine; (2S,4R)-4-glycylamino-2-(3-biphenyloxy)methylpyrrolidine; (2R,4S)-4-glycylamino-2-(4-biphenyloxy)methylpyrrolidine; (2R,4S)-4-glycylamino-2-(3-biphenyloxy)methylpyrrolidine, trans-4-(3-biphenyloxy)-L-proline 2-aminoethylamide; (2S,4R)-2-(2-amino-1-hydroxyethyl)-4-(3-biphenyloxy)pyrrolidine; 1-(N-trans-4-glycylamino-L-prolylamino)-3-(4-phenylpropanoylamino)benzene; 2-(trans-4-glycylanino-L-prolylamino)-6-(4-phenylpropanoylamino)pyridine; (2S,4R)-4-glycylamino-2-((E and Z)-4-phenylstyryl)pyrrolidine; globomycin (glycine, N—(N—(N—(N—(N-(3-hydroxy-2-methyl-1-oxononyl)-N-methylleucyl)-L-alloisoleucyl)-L-seryl)-L-allothreonyl)-, rho-lactone); carbonyl cyanide m-chlorophenylhydrazone (CCCP); pyridoquinolone; MC-04,124 ((2R,4R)-4-(aminomethyl)-N-[(2R)-1-oxo-4-phenyl-1-(quinolin-6-ylamino) butan-2-yl]pyrrolidine-2-carboxamide); or MC-02,595 (D-ornithine-D-homophenylalanine-3-aminoquinoline).

Contrary to the disclosure in WO 2016/080846, the inventors have found that halogenated salicylanilides (e.g. niclosamide, oxyclozanide, rafoxanide, and closantel) are effective against H. pylori without the need for a bacterial efflux inhibitor. This simplifies the treatment and minimises subject exposure to additional agents such as bacterial efflux pump inhibitor. Accordingly in certain embodiments, the halogenated salicylanilide, (e.g. niclosamide, oxyclozanide, rafoxanide, or closantel), is used in the absence of concurrent administration with a bacterial efflux inhibitor, in particular any of the bacterial efflux inhibitors disclosed in WO 2016/080846, in the uses, methods, compositions and devices as disclosed herein.

Agents that Increase the Permeability of a Bacterial Cell Membrane

WO 2017/200396 refers to polymyxins, such as polymyxin B, structural/functional analogues of polymyxin B, polymyxin E (i.e. colistin), structural/functional analogues of polymyxin E, and cationic or anionic peptides that disrupt cell membrane homeostasis and/or polarity, e.g. gramicidin, as examples of agents that increase the permeability of the bacterial cell membrane.

Further examples of agents that in WO 2017/200396 are asserted to increase the permeability of bacterial cell membranes are hyperosmotic solutions, calcium ion chelators, surfactants, and/or polarity and receptor mediated permeabilizing agents including drug based agents that increase permeability of a bacterial cell membrane, as well as combinations thereof.

Examples of calcium ion chelators mentioned in WO 2017/200396 are iminodiacetic acid (IDA), nitriloacetic acid (NTA), ethylenediaminomonoacetic acid (EDMA), ethylenediaminodiacetic acid (EDDA), and ethylenediaminotetraacetic acid (EDTA).

Examples of ionic surfactants mentioned in WO 2017/200396 are sodium taurodihydrofusidate, sodium salicylate, sodium caprate, and sodium glycocholate.

Examples of non-ionic surfactants mentioned in WO 2017/200396 are cholylsarcosine, isopropyl myristate, partially hydrolyzed triglycerides, fatty-acid sugar derivatives, and oleic acid derivatives.

Reference is in WO 2017/200396 made to Hurdle et al. (2011) and Guihelemelli et al. (2013) for examples of cationic or anionic peptides that disrupt cell membrane homeostasis and/or polarity.

Examples of drug based agents that increase permeability of a bacterial cell membrane mentioned in WO 2017/200396 are polymyxins. Structural/functional analogues of polymyxin B, which differ in the N-terminal fatty acyl group and amino acid residue at position-6 and position-7 are mentioned. Structural/functional analogues of polymyxin E, which differ in the N-terminal fatty acyl group and amino acid residue at position-6 and position-7 are mentioned.

Contrary to the disclosure in WO 2017/200396, the inventors have found that halogenated salicylanilides (e.g. niclosamide, oxyclozanide, rafoxanide, and closantel), are effective against H. pylori in the absence of concurrent administration of an agent selected from the group consisting of polymyxins and gramicidin. Accordingly in certain embodiments, the halogenated salicylanilide (e.g. niclosamide, oxyclozanide, rafoxanide, or closantel) is used in the absence of concurrent administration with an agent that increases the permeability of a bacterial cell membrane, in particular any of the permeability enhancers disclosed in WO 2017/200396, in the uses, methods, compositions and devices as disclosed herein.

Pharmaceutical Compositions

The halogenated salicylanilide may be administered to the subject in the form of a pharmaceutical composition, such as a topical formulation, comprising the halogenated salicylanilide, or a pharmaceutically acceptable salt or solvate thereof, and a pharmaceutically acceptable excipient. The composition may be in a form suitable for oral use (for example as tablets, lozenges, hard or soft capsules, aqueous or oily suspensions, emulsions, dispersible powders or granules, syrups or elixirs). For example, the composition may be in the form of an oral tablet, capsule or granule composition comprising the halogenated salicylanilide or a pharmaceutically acceptable salt or solvate thereof, a filler (e.g. corn starch), a binder (e.g. polyvinylpyrrolidone) and a lubricant (e.g. magnesium stearate).

Dosage

The amount of the halogenated salicylanilide that is combined with one or more excipients to produce a single dosage form will necessarily vary depending upon the subject treated and the nature of the disease or infection being treated particular route of administration.

For example, a formulation in a unit dose form such as a tablet or capsule intended for oral administration or another dose form to be administered parenterally to humans will generally contain, for example, from 0.1 mg to 5 mg, for example from 0.5 mg to 5 g, from 0.5 to 2 000 mg or from 10 to 500 mg of the halogenated salicylanilide, or a pharmaceutically acceptable salt or solvate thereof, compounded with an appropriate and convenient amount of excipients which may vary from about 5 to about 98 percent by weight of the total composition.

The dose of the halogenated salicylanilide (e.g. oxyclozanide, niclosamide, rafoxanide, or closantel), or a pharmaceutically acceptable salt or solvate thereof, administered to a subject for the treatment of the diseases or infections caused by or associated with $H.$ $pylori$ described herein, will naturally vary according to the nature and severity of the conditions, the age and sex of the animal or subject and the route of administration, according to well-known principles of medicine.

The halogenated salicylanilide (e.g. oxyclozanide, niclosamide, rafoxanide, or closantel), or a pharmaceutically acceptable salt or solvate thereof, may be administered in a dose of about 0.001 to about 75 mg/kg, for example from about 0.013 to about 66.7 mg/kg, about 0.5 to about 30 mg/kg or from about 2.5 to about 30 mg/kg. The halogenated salicylanilide, or a pharmaceutically acceptable salt or solvate thereof, may be administered within these dosage ranges to the subject from 1 to 4 times per day.

Subjects

The subject treated with the halogenated salicylanilide may be a warm-blooded animal, preferably the subject is a human. Also contemplated is the treatment of a non-human subject such as a warm blooded non-human mammal. For example, the subject may be a companion animal such as a cat, dog or horse. In some embodiments, the subject is a dog or a cat. In some embodiments the subject is a dog.

EXAMPLES

The invention is further illustrated by the following examples.

Example 1: Antibacterial Susceptibility

A pilot screening for anti-$H.$ $pylori$ activity by a broth microdilution assay using the halogenated salicylanilides niclosamide, oxyclozanide rafoxanide and closantel.

The $H.$ $pylori$ reference strain 60190 (ATCC 49503) was purchased from American Type Culture Collection (ATCC). Bacteria were cultured on $Brucella$ agar (Becton Dickinson, Braintree, Mass., USA) supplemented with 10% fetal bovine serum (FBS; Gibco, Long Island, N.Y., USA) and $H.$ $pylori$ selective supplement (vancomycin—10.0 mg/l, cefsulodin—5.0 mg/l, trimethoprim—5.0 mg/l, amphotericin B—5.0 mg/l) (Oxoid, Hampshire, UK) and maintained in humidified incubators at 37° C. under an atmosphere of 5% $CO_2$.

In vitro antibacterial activity was tested using the broth microdilution assay Milkier, M. A. Methods for dilution antimicrobial susceptibility tests for bacteria that grow aerobically: approved standard. (Clinical and Laboratory Standards Institute, 2006). Experiments were carried out in triplicate using Müller-Hinton broth (BD Biosciences, Franklin Lakes, N.J., USA) supplemented with 10% FBS in 96-well plates (BD Biosciences) at a total assay volume of 100 µL. Two-fold serial dilutions were prepared between the concentration range 0.01-64 µg/mL. An initial bacterial inoculum was adjusted to OD600=0.06 and incubated with test compounds at 37° C. for 3 days in humidified incubators under the 5% CO2 atmosphere. OD600 was measured and the lowest concentration of compound that inhibited bacterial growth was reported as the MIC.

The halogenated salicylanilides niclosamide, oxyclozanide, rafoxanide and closantel inhibited the growth of $H.$ $pylori$ strain 60190. More specifically, the minimum inhibitory concentration (MIC) of niclosamide, oxyclozanide, rafoxanide, and closantel were 0.25, 2.0, 4.0 and 16 µg/mL, respectively (Table 1) and the minimum bactericidal concentration (MBC) of niclosamide, oxyclozanide, rafoxanide, and closantel against $H.$ $pylori$ were 0.5, 4.0, 8.0 and 16 µg/mL, respectively (Table 1). The MIC and MBC of amoxicillin and clarithromycin were measured as comparators.

TABLE 1

| Antimicrobial agent | MIC µg/mL | MBC µg/mL |
| --- | --- | --- |
| Niclosamide | 0.25 | 0.5 |
| Oxyclonazide | 2.0 | 4.0 |
| Rafoxanide | 4.0 | 8.0 |
| Closantel | 16 | 16.0 |
| Amoxicillin | 0.01 | 0.5 |
| Clarithromycin | 0.0025 | 0.25 |

Niclosamide was also tested against $H.$ $pylori$ strains 49503, 43504 and 51932 using the same method. The MIC (µg/mL) is shown in Table 2:

TABLE 2

| Strain | Niclosamide MIC (µg/mL) | Amoxicillin MIC (µg/mL) | Clarithromycin MIC (µg/mL) |
| --- | --- | --- | --- |
| $H.$ $Pylori$ 49503 | 0.25 | 0.01 | 0.0025 |
| $H.$ $Pylori$ 43504 | 0.125 | 0.03 | 0.005 |
| $H.$ $Pylori$ 51932 | 0.5 | 0.01 | 0.005 |

Example 2: Time to Kill Assay

The MIC of niclosamide was the lowest of the halogenated salicylanilides tested (0.25 µg/mL against strain 60190, see Table 1). Niclosamide was therefore tested time to kill assays were used to confirm the killing properties of niclosamide against $H.$ $pylori$. Agar grown $H.$ $pylori$ bacteria (strain 60190) were suspended in fresh Mueller Hinton Broth (MHB) with 10% Fetal bovine serum (FBS) to a density of $10^9$ cells/mL and placed into 10 mL tubes (BD Biosciences). Test compounds were then added at the 4×MIC and incubated with agitation at 37° C. under microaerophilic conditions. Aliquots were periodically drawn from the tubes, serially diluted and plated onto *Brucella* agar (BD Biosciences) supplemented with 10% FBS. CFUs were counted after a 3-day incubation and assays were carried out in duplicate.

Figure 1:
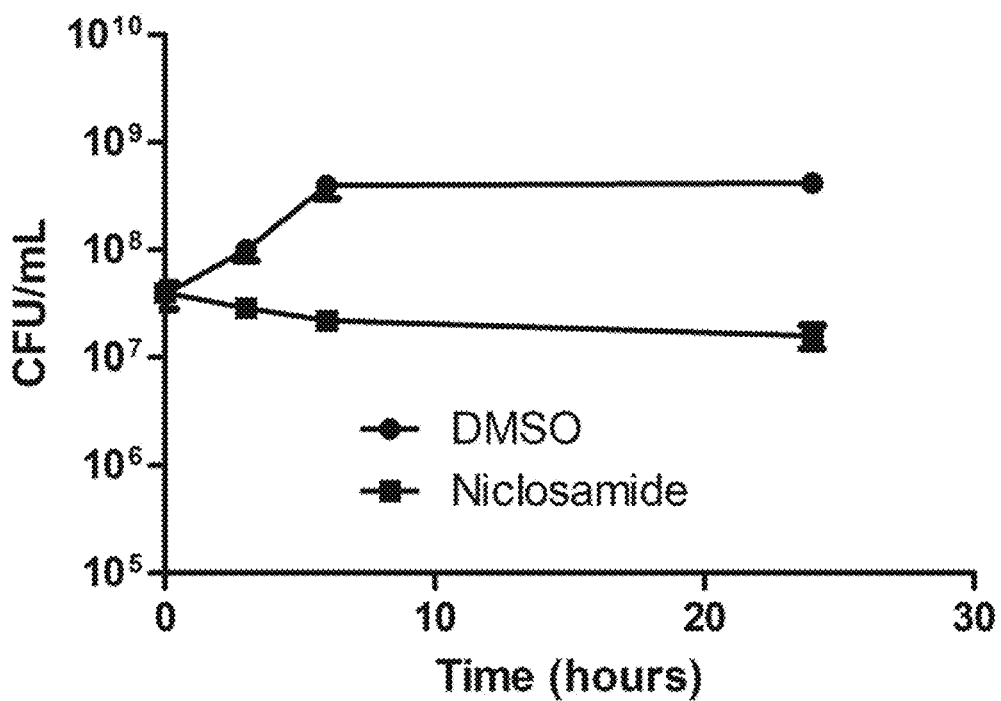
FIG. 1 shows the killing kinetics of niclosamide on *H. pylori* at 4×MIC (1 µg/mL) in a time to kill assay and was found to be bacteriostatic.

Bacterial cells ($10^9$/mL) exposed to the niclosamide at 4×MIC showed potent inhibition of the bacterial cell division relative to DMSO controls (FIG. 1) and shows that niclosamide is bacteriostatic against *H. pylori*. Of note, clarithromycin, a commonly prescribed antibiotic for *H. pylori* treatment, is also bacteriostatic (De Francesco et al. World journal of gastrointestinal pathophysiology 2, 35 (2011)).

Example 3: Effect of pH on MIC

The broth microdilution assay described in Example 1 was used to demonstrate the stability of niclosamide, amoxicillin and clarithromycin at low pH using MHB supplemented with 10% FBS against *H. pylori* (strain 60190). The pH was adjusted to acidic condition with 1 N HCl. The minimal bactericidal concentration (MBC) was determined by plating 5 μL of broth culture from the MIC assay onto Müller-Hinton agar (BD Biosciences) supplemented with 10% FBS. After 72 h, the lowest concentration at which colonies were not observed was reported as the MBC.

Figure 2:
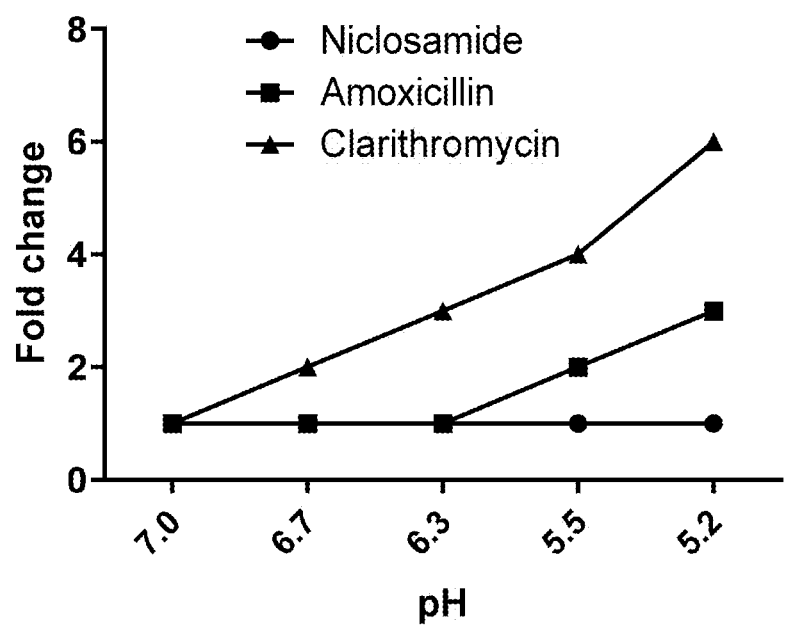
FIG. 2 shows the effect of pH on the MIC of niclosamide, amoxicillin and clarithromycin. The y-axis shows the fold change in MIC compared to the MIC at pH 7.0.

The antibacterial potential of niclosamide did not change in acidic pH (tested between pH 7.0 to 5.2) (FIG. 2). The MIC of niclosamide in low pH remained the same as in neutral pH (MIC 0.25 μg/mL) indicating that niclosamide is expected to retain activity in the low pH environment of the gastric mucosa. In contrast, the MIC of the standard antibiotics amoxicillin and clarithromycin increased at acidic pH.

Example 4: Multi-step Mutation Frequency

To determine whether *H. pylori* can develop resistance against niclosamide, bacterial cells were suspended in MHB with 10% FBS at OD600=0.06 in the presence of serially diluted niclosamide and incubated, as described in the antibiotic susceptibility assays sub-section. The standard antibiotics amoxicillin and clarithromycin were used as controls. From the highest drug concentration allowing visible growth at sub-MIC concentration, aliquots were diluted (1:40) into fresh medium. These were used to inoculate the second set of serial drug dilutions as described by Dalhoff et al. (Clin Infect Ds. 2001 Mar. 15; 32 Suppl, 1:S16-22). After a 3-day incubation, *H. pylori* bacteria (strain 60190) were passaged sequentially over 30 days and the OD was recorded.

Figure 3:
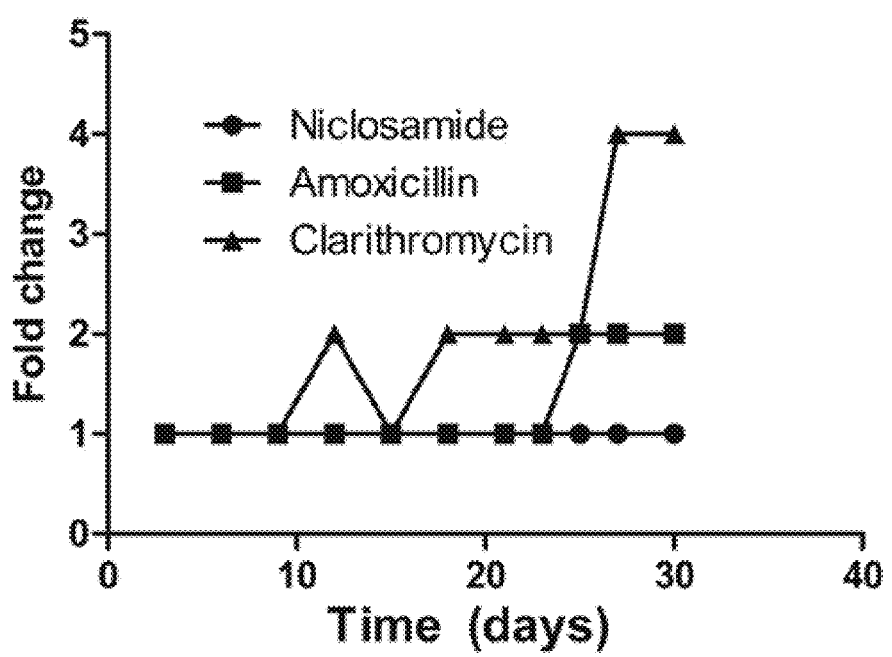
FIG. 3 shows the mutation frequency of *H. pylori* to niclosamide. *H. pylori* were cultured with the amoxicillin, clarithromycin or niclosamide for 30 days. The y-axis shows the fold increase in MIC compared to the MIC at the start of the study.

The MIC increased 2-fold for clarithromycin and amoxicillin, while that of niclosamide remained constant through at least 10 passages (FIG. 3). Similarly, the MIC to amoxicillin and clarithromycin increased when *H. pylori* bacteria were exposed to these agents for more than 15 days and 24 days, respectively. More specifically, during continuous passage with amoxicillin and clarithromycin, the MIC increased by 2-fold and 4-fold, respectively (FIG. 3). In contrast the MIC to niclosamide remained unchanged, indicating a low risk of emerging resistance to niclosamide during *H. pylori* treatment.

Example 5: Niclosamide Inhibits Cellular Adhesion and Invasion of *H. pylori* Adhesion The AGS (Gastric adenocarcinoma cell lines) cell line was used to examine inhibition of adhesion and invasion of *H. pylori* (strain 60190) by niclosamide, as described by Schmitt et al. (Front Cell Infect Microbiol. 2013; 3:93). The AGS cells were grown in Dulbecco's Modified Eagle Medium (DMEM, ex. Gibco), supplemented with 10% fetal bovine serum (Gibco) and 1% penicillin/streptomycin (Gibco) and maintained at 37° C. in 5% $C_O2$. Then, $5 \times 10^5$ cells in antibiotic and serum-free DMEM were seeded in 6-well plates 24 hours prior to infection. *H. pylori* bacteria at a multiplicity of infection (MOI)=100 were added and allowed to adhere to the surface of the AGS cells. Planktonic bacteria were removed after 2 hours and DMEM with niclosamide (2×MIC) was then added to the wells containing the AGS. The mammalian cells were lysed by 0.1% saponin after 20 hours of incubation and the adhered bacteria were then serially diluted, plated in *Brucella* agar supplemented with 10% FBS, and incubated as described above. A control arm of DMSO and a comparator using amoxicillin at a concentration of 0.1 μg/mL (10×MIC) was also assessed.

Figure 4A:
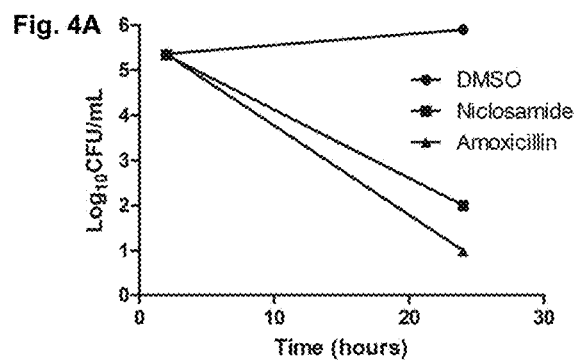
FIG. 4A shows the effect of niclosamide on the adhesion of *H. pylori* to AGS (Gastric adenocarcinoma cells) following incubation at 2×MIC for 24 hours. Data was also generated for a DMSO control and amoxicillin (concentration of 0.1 µg/mL). The y-axis shows the log$_{10}$ CFU/mL vs time on the x-axis.

After incubation the administrated concentration of niclosamide eliminated the adhered bacteria and reduced CFU/mL counts by 3-$\log_{10}$ Amoxicillin eliminated bacterial adhesion completely (FIG. 4A).

Invasion

To determine the effect of niclosamide on invasion a gentamicin protection assay was performed in which AGS cells infected with *H. pylori* as described in the adhesion assay above, were treated with DMEM supplemented with 200 μg/mL gentamicin and incubated for 1.30 hours to eliminate extracellular bacteria. Antibiotic and serum-free DMEM with and without test compounds were added and incubated in 5% $CO_2$ for 20 hours. Cell lysate preparation, plating, and incubation were carried out as described in the adhesion assay. Assays were carried out in triplicate.

Figure 4B:
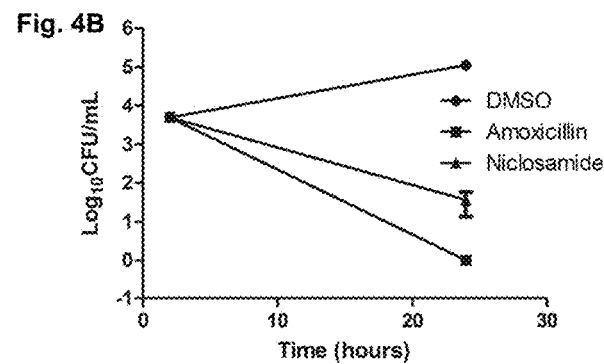
FIG. 4B shows the effects of test compounds on AGS cells invaded by *H. pylori* in a gentamicin protection assay. The y-axis shows the log$_{10}$ CFU/mL vs time on the x-axis.

Niclosamide (2×MIC, 0.5 μg/mL) reduced 3-$\log_{10}$ CFU in AGS cell lines. Amoxicillin (concentration 0.1 μg/mL) eliminated bacteria completely (FIG. 4B).

An apparent contradiction was observed between the killing kinetics and adhesion/invasion assays. Niclosamide appeared bacteriostatic during the killing kinetics (Example 3) and bactericidal during adhesion/invasion assays (Example 6). Without wishing to be bound by theory it is hypothesized that the variance in the efficacy of niclosamide could be due to a difference in bacterial cell concentration in these assays. The density of bacterial inoculum in the adhesion/invasion assays was lower than the time-to-kill assay. Mirshahi et al. (J. Clin. Pathol. 1998 March; 51(3): 220-4) observed similar behaviour with the PPI omeprazole, which also appears bacteriostatic in high density and bactericidal in a low density of *H. pylori* bacteria.

Example 6: Inhibition of IL-8 Secretion

Real-Time (RT-PCR) was carried out to determine whether niclosamide has an inhibitory role in IL-8 secretion. MKN-28 cells were co-cultured with *H. pylori* (MOI=100) in the presence or absence of a test compound. At 24 hours, RNA was isolated from the infected host cells. cDNA was synthesized using the Verso cDNA (Invitrogen) synthesis kit according to manufacturer instructions. Quantitative real-time reactions were carried out in a Bio-Rad iTaq universal SYBR (Bio-Rad, Hercules, Calif. USA) one-step kit and a CFX98 real-time PCR cycler as described by Zheng et al. (Future Med. Chem. 2018, February; 10(3):283-296). The relative gene expression was calculated from Cq values using a ΔΔCq method. The real time PCR primers used in the IL-8 secretion study are shown in Table 3.

Figure 4C:
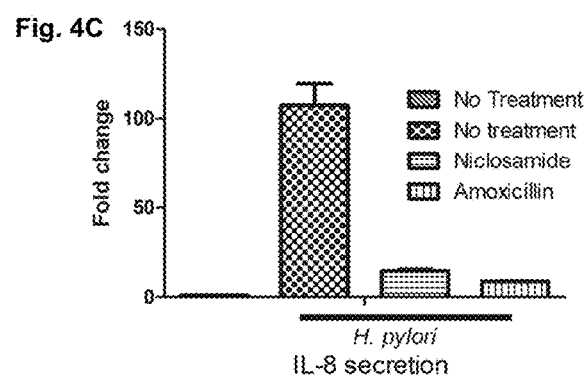
FIG. 4C shows the fold change of IL-8 secretion from MKN-28 cells co-cultured with *H. pylori* (MOI=100) in the presence or absence of a test compound (niclosamide or amoxicillin). The Y-axis shows the fold-change in IL-8 secretion compared to infected cells without treatment with a test compound.

FIG. 4C shows that niclosamide treatment (4×MIC, 1.0 µg/mL) during a 24 hour incubation period inhibited IL-8 secretion in *H. pylori* (MOI=50) infected MKN-28 cells. Amoxicillin (10× MIC) also inhibited IL-8 secretion.

TABLE 3

| Primer | Relevant sequences | Size | Amplification cycles | Annealing temperature | References |
|---|---|---|---|---|---|
| vacA-F | 5' AAACGACAAGAAGAGATCAGT 3' | 291 | 20 | 58 | 51, 63 |
| vaca-R | 3' CCAGCAAAAGGCCCATCAA 5' | | | | |
| galE-F | 5' ATGGCATTATTATTCACAGG 3' | 461 | 20 | 58 | 51 |
| galE-R | 3' GCTCCATAAGGATTAATGGG 5' | | | | |
| Real-Time PCR Primers | | | | | |
| IL 8-F | 5'-ACT GAG AGT GAT TGA GAG TGG AC-3 | | 40 | | 64 |
| IL 8-R | 5'-AAC CCT CTG CAC CCA GTT TTC-3' | | | | |
| 18 rRNA-F | 5'-CGG CGA CGA CCC ATT CGA AC-3' | | 40 | | 64 |
| 18s rRNA-R | 5'-GAA TCG AAC CCT GAT TCC CCG TC-3' | | | | |

References:
[51] Tharmalingam, N. et al. Piperidine treatment suppresses Helicobacter pylori toxin entry in to gastric epithelium and minimizes β-catenin mediated oncogenesis and IL-8 secretion in vitro. American journal of translational research 8, 885 (2016).
[63] Boonjakuakul, J. K., Canfield, D. R. & Solnick, J. V. Comparison of Helicobacter pylori virulence gene expression in vitro and in the Rhesus macaque. Infection and immunity 73, 4895-4904 (2005).
[64] Tsai, K.-W. et al. Difference in the regulation of IL-8 expression induced by uropathogenic E. coli between two kinds of urinary tract epithelial cells. Journal of biomedical science 16, 91 (2009).

Example 7: Synergy Studies

Antibacterial synergy was tested using the checkerboard assay using the method described in Zheng Z et al. (Antimicrob. Agents Chemother. 2017 July; 61(7)). Niclosamide was combined with antibiotics and proton pump inhibitors (PPIs). Cultures of *H. pylori* (strain 60190) were adjusted to $OD_{600}$=0.06 and added to compound pairs that had been serially diluted in the same 96-well plates, vertically for one compound and horizontally for the other. Assays were carried out in triplicate as described in the antibacterial susceptibility assay described above. The combinatorial inhibitory concentration was indicated by the fractional inhibitory concentration index (FICI):

FICI=$MIC_A$ combination/$MIC_A$ alone+$MIC_B$ combination/$MIC_B$ alone

Paired combinations of compounds and their observed FICI are listed in Table 4. Synergistic activity, where the combined antibacterial effect of the 2 antimicrobial agents is more than the sum of their effects alone, is defined by FICI 0.5, antagonism by FICI >4.0 and 'no interaction' by FICI >0.5-4.0.

TABLE 4

FICI value of niclosamide with test compound.

| Test compound | FICI value Niclosamide |
|---|---|
| Amoxicillin | 2.0 |
| Clarithromycin | 1.0 |
| Omeprazole | 0.625 |
| Metronidazole | 0.75 |
| Pantoprazole | 0.75 |

Niclosamide is partially synergistic with metronidazole. Niclosamide is also partially synergistic with the PPIs omeprazole and pantoprazole tested. Taken together, the Examples herein indicate that niclosamide is highly active against *H. Pylon* in acidic pH and is also partially synergistic with PPIs such as omeprazole and pantoprazole. As such niclosamide is expected to be effective as a monotherapy or in combination with a PPI and/or metronidazole in the treatment or prevention of *H. Pylon* infections.

Example 8: Effect of Niclosamide on *H. pylori* VacA Toxin Expression and *H. pylori* Mediated Vacuolation Light Microscopy Imaging for Vacuolation

*H. Pylon* bacteria secrete VacA toxin via a type V secretion system (Galmiche et al. Gut Microbes. 2010 November-December; 1(6):392-5. 44). This toxin binds to host gastric epithelial cells and its internalization leads to vacuolation, characterized by the accumulation of large vacuoles in gastric epithelial cells during the infection process.

AGS cells were harvested and seeded into a 6 well plate at a concentration of $5×10^5$ cells, 24 h before experimentation. *H. Pylon* bacteria (strain 60190) were harvested and washed with sterile PBS and co-cultured with AGS at a MOI of 100. After incubation for 24 h, the cells were washed, magnified under a microscope, and examined for vacuolation.

Results revealed that sub-MIC (0.2 µg/mL) of niclosamide prevented vacuolation as illustrated in FIG. 5 A-D. (A) AGS alone; (B) AGS treated with niclosamide; (C) AGS cells infection with *H. pylori*; (D) AGS cells cocultured with *H. pylori* and niclosamide.

RT-PCR Study on VacA Toxin Expression

To determine the effect of niclosamide on *H. Pylon* VacA toxin expression, bacteria grown on agar were suspended in *Brucella* broth supplemented with 10% FBS ($OD_{600}$=0.06) in dilutions of niclosamide (0, 100, 150, or 200 ng/mL) and incubated for 3 days (analogous to the method described in De Kimpe et al. Proc. Natl. Acad. Sci. USA, 1995 Oct. 24; 92(22):10359-63). After 3 days, the bacteria were washed and treated with TRIZOL (Invitrogen, Carlsbad, Calif., USA), and the RNA concentration was determined using a NanoVue Plus spectrophotometer (GE Healthcare, Fairfield, Conn., USA). PCR amplifications were performed, and the products were analysed by gel electrophoresis (1.0% agarose) containing SYBR® Safe (Invitrogen). Gel images were captured and analysed using the Quantity One System. Results indicate that at the sub-MIC level of 200 ng/mL, niclosamide downregulates VacA expression compared to the housekeeping gene rpoB (FIG. 5E).

Example 9: In Vivo Efficacy of Niclosamide in the *Galleria mellonella* Model

Assays were performed as described by Giannouli et al. (BMC Microbiol. 2014 Aug. 27; 14:228), an alternative model host for the evaluation of antimicrobial agents against *H. pylori* infection.
Twelve randomly selected *G. mellonella* larvae (Vanderhorst, Inc., St. Mary's, OH, USA) between 300-350 mg were used for each group in the experiment. *H. pylori* cells were washed with PBS and diluted to $OD_{600}$ nm=0.3, before inoculation into *G. mellonella* larvae. A 10 µL inoculum was injected into the last left proleg using a 10 µL Hamilton syringe. After 2 hours, compounds were administered at into the last right proleg and the wax moths were incubate at 37° C. Niclosamide was administered at a concentration of 25 mg/kg. Clarithromycin administered at a concentration of 10 mg/kg was used as a comparator. Three control groups were included (1) injected with PBS only; (2) inoculated with *H. pylori* but treated with sham injections; and (3) no manipulation. *G. mellonella* survival was evaluated up to 120 hours. The surviving larvae were monitored every 24 hours and were considered dead if they were unresponsive to external stimuli (touch). Killing curves and differences in survival were analysed by the Kaplan-Meier method using GraphPad Prism version 6.04 (GraphPad Software, La Jolla, Calif., USA). Statistical analysis (Kruskal-Wallis test) was carried out using the same program.
About 60% of wax-moth survived up to 120 hours in the niclosamide treated group (25 mg/kg) as illustrated in the survival curve of FIG. 6.

Example 10: Niclosamide Inhibits *H. pylori* Motility at Sub-MIC Concentrations

Initial colonization of the stomach mucosa by *H. pylori* is associated with the motility of bacteria (Ottemann et al. Infect Immun. 2002 April; 70(4):1984-90). To evaluate the effects of niclosamide on *H. pylori* motility, a motility assay was performed as described in Suerbaum et al. (J. Bacteriol. 1993 June; 175(11):3278-88). *Brucella* agar with 10% FBS was prepared in 2 layers. The bottom layer contained pre-casted 1.5% agar and the softer top layer was comprised of 0.4% agar and niclosamide (75, 100, 150 or 200 ng/mL). Agar-grown *H. pylori* cells (strain 60190) were sliced and the densely grown *H. pylori* agar slice was placed facing up towards the soft layer and incubated as described in bacteria and mammalian cell culture subsection of Tharmalingam et al. (Infect Agent Cancer. 2014; 9(1):43).
*H. pylori* motility decreased in a dose-dependent manner with the concentration of niclosamide (from 0.10 to 0.20 µg/mL). The swarming movement of *H. pylori* bacteria decreased gradually with the concentration of niclosamide. At sub-MIC (0.2 µg/mL) concentrations, the motility was abated (FIGS. 7 A-E).
To study further the decreased motility, the morphology of *H. pylori* bacteria under a scanning electron microscope (SEM) in the presence or absence of niclosamide was investigated.

*H. pylori* bacteria were suspended in *Brucella* broth with 10% FBS in the presence or absence or niclosamide (1×, 4×, 8× MIC) for 2 hours under microaerophilic conditions with agitation. After 2 hours, the bacterial cells were harvested and adhered to coverslips using a 1% poly-L-lysine (Sigma-Aldrich) solution. Then, cells were fixed in a 5% glutaraldehyde (Sigma-Aldrich), 4% paraformaldehyde (Sigma-Aldrich), 0.1 M sodium cacodylate (Sigma-Aldrich) solution. After fixation, the cells were washed in a 0.1 M sodium cacodylate buffer and dehydrated by immersion in increasing concentration of ethanol (from 30 to 100%). The critical point drying method (CPD) was applied to dehydrate the samples, the coverslips were mounted on aluminium stubs, and then sputter coated with gold (Emitech K550, Ashford, Kent, UK). Images were taken on a Hitachi 2700 Scanning electron microscope.
The untreated *H. pylori* cells were helically shaped, had intact membrane surface, and possessed well-formed bacterial flagella (FIG. 8 A-B). However, niclosamide-treated *H. pylori* cells became short bacilli and the morphology changed in a dose-dependent manner (FIG. 8 C-H). The helical shape of the bacterium was shortened at 1× MIC (FIG. 8 C, D) and appeared to become Cocco-bacillary (FIG. 8 E-H) at 4× and 8× MIC. The amoxicillin (0.1 µg/mL (10×MIC), FIG. 8 I, J) and CCCP (10 µM, FIGS. 8 K and L) compared to the untreated control groups (FIG. 8, A, B) and also exhibited morphological changes and decreased cell size. Interestingly, treatment with niclosamide caused flagellar deformation, similar to that reported by Zhang et al. (J. Immunol 2016 Feb. 15; 196(4):1799-809) after exposure to the antimicrobial peptide cathelicidin. This effect in the bacterial flagella may explain the effects of niclosamide in *H. pylori* motility.

Example 11: In-Vivo Study

The effect of a halogenated salicylanilide, for example niclosamide, against *H. pylori* may be assessed in the Mongolian gerbil (*Meriones unguiculatus*) model as described in Noto, et al., The Mongolian Gerbil: a robust model of *Helicobacter pylori*-induced gastric inflammation and cancer, in Gastrointestinal Physiology and Diseases. 2016, Springer. p. 263-280.
The effect of the halogenated salicylanilide alone or in combination with an antibiotic (for example, clarithromycin or amoxicillin and/or a PPI (e.g. omeprazole) against *H. pylori* infection in the animal, may be assessed as illustrated in the flow chart of FIG. 9. In this study the active agents can be administered to 6-week old male Mongolian gerbils orally by gavage.

Additional Embodiments

Also disclosed are the embodiments set out in the following numbered clauses:
1. A method for the prevention or treatment of a disease or infection caused by or associated with *H. pylori* in a subject infected with *H. pylori*, the method comprising orally administering to the subject an effective amount of a halogenated salicylanilide, or a pharmaceutically acceptable salt or solvate thereof.
2. The method of clause 1, wherein the subject is not treated concurrently with a proton pump inhibitor.
3. The method of clause 1, wherein the subject is not treated concurrently with any other antibiotic.

4. The method of clause 1, wherein the subject is not treated concurrently with a proton pump inhibitor or any other antibiotic.
5. A method for the prevention or treatment of a disease or infection caused by or associated with *H. pylori* in a subject infected by *H. pylori*, the method comprising orally administering to the subject an effective amount of a halogenated salicylanilide, or a pharmaceutically acceptable salt or solvate thereof, concurrently with an effective amount of a proton pump inhibitor (PPI).
6. The method of clause 5, wherein the proton pump inhibitor is a benzimidazole or azabenzimidazole derivative, for example wherein the PPI is selected from: omeprazole, hydroxyomeprazole, esomeprazole, lansoprazole, dexlansoprazole, pantoprazole, rabeprazole, tenatoprazole, and leminoprazole, or a pharmaceutically acceptable salt, or solvate thereof.
7. The method of clause 5, wherein the proton pump inhibitor is selected from omeprazole and pantoprazole, or a pharmaceutically acceptable salt, or solvate thereof.
8. The method of any of clauses 5 to 7, wherein the subject to be treated has not been previously treated with a PPI, the method comprising orally administering an effective amount of the halogenated salicylanilide, or a pharmaceutically acceptable salt or solvate thereof; and following eradication of the *H. pylori* infection, administering to the subject an effective amount of a proton pump inhibitor.
9. A method for the prevention or treatment of a disease or infection caused by or associated with *H. pylori* in a subject infected with *H. pylori*, the method comprising orally administering to the subject an effective amount of a halogenated salicylanilide, or a pharmaceutically acceptable salt or solvate thereof, concurrently with an effective amount of a nitroimidazole antibiotic.
10. The method of clause 9, wherein the nitroimidazole antibiotic is metronidazole, or a pharmaceutically acceptable salt thereof.
11. The method of clause 9 or clause 10, wherein the subject is treated concurrently with a proton pump inhibitor.
12. A method for eradicating a *H. pylori* infection in a subject with a disease or infection caused by or associated with *H. pylori*, the method comprising orally administering to the subject an effective amount of a halogenated salicylanilide, or a pharmaceutically acceptable salt or solvate thereof.
13. The method of clause 12, wherein the subject is not treated concurrently with a proton pump inhibitor.
14. The method of clause 12, wherein the subject is not treated concurrently with any other antibiotic.
15. The method of clause 12, wherein the subject is not treated concurrently with a proton pump inhibitor or any other antibiotic.
16. The method of any one of clauses 1 to 15, wherein the disease or infection caused by or associated with *H. pylori* is selected from: dyspepsia, gastritis, peptic ulcer disease, premalignant gastric lesions, gastric cancer and gastric mucosa-associated lymphoid tissue (MALT) lymphoma.
17. The method of any one of clauses 1 to 15, wherein the disease or infection caused by or associated with *H. pylori* is an extra-gastric condition selected from: iron-deficiency anaemia, idiopathic thrombocytopenic purpura (ITP) and vitamin B12 deficiency.
18. A method for eradicating a *H. pylori* infection in a subject, the method comprising orally administering to the subject an effective amount of a halogenated salicylanilide, or a pharmaceutically acceptable salt or solvate thereof
19. The method of any one of clauses 1 to 18 wherein the treatment inhibits invasion of *H. pylori* into gastric epithelial cells.
20. The method of any one of clauses 1 to 19, wherein the treatment reduces or eliminates intracellular *H. pylori* from gastric epithelial cells.
21. The method of any one of clauses 1 to 20, wherein the treatment inhibits the adhesion of *H. pylori* to gastric epithelial cells.
22. The method of any one of clauses 1 to 21, wherein the treatment reduces or eliminates *H. pylori* adhered to gastric epithelial cells.
23. The method of any one of clauses 1 to 22, wherein the treatment inhibits *H. pylori* mediated vacuolation of gastric epithelial cells.
24. A method for eradicating a *H. pylori* infection in a subject, wherein the subject has a premalignant gastric epithelial lesion, the method comprising orally administering to the subject an effective amount of a halogenated salicylanilide, or a pharmaceutically acceptable salt or solvate thereof.
25. The method of clause 24, wherein the premalignant gastric epithelial lesion is gastric epithelial dysplasia.
26. A method for treating or preventing atrophic gastritis in a subject infected with *H. pylori*, the method comprising orally administering to the subject an effective amount of a halogenated salicylanilide, or a pharmaceutically acceptable salt or solvate thereof, wherein the method reduces *H. pylori* induced IL-8 secretion in the subject.
27. The method according to any one of clauses 1 to 26, wherein the halogenated salicylanilide is of the formula (I):

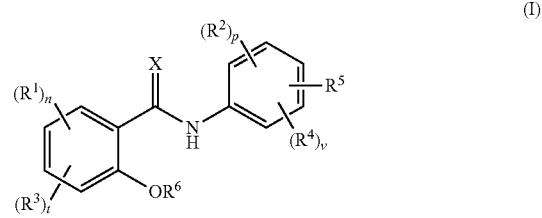

wherein
X is O or S;
$R^1$ and $R^2$ are at each occurrence independently selected from halo;
$R^3$ and $R^4$ are at each occurrence independently selected from H, $C_{1-6}$ alkyl, —$OR^{41}$, —$NO_2$ and —CN;
$R^5$ is H or -$L^1$-$R^7$;
$R^6$ is H or —C(O)$R^{42}$;
$L^1$ is selected from a bond, O, S, or —$(CR^{43}R^B)_o$—, wherein o is 1 or 2;
$R^7$ is phenyl, unsubstituted or substituted with 1, 2, or 3 groups selected from halo, $C_{1-4}$ alkyl, —$OR^{44}$, —$NO_2$ and —CN;
$R^{41}$, $R^{42}$, $R^{43}$ and $R^{44}$ are at each occurrence independently selected from H and $C_{1-4}$ alkyl;
$R^B$ is at each occurrence selected from H, $C_{1-4}$ alkyl and —CN;
n and p are each independently selected from 0, 1, 2, 3 or 4, with the proviso that n+p is at least 1; and
t and v are independently selected from 0, 1 and 2;
or a pharmaceutically acceptable salt, or solvate thereof.
28. The method according to any one of clauses 1 to 26, wherein the halogenated salicylanilide is selected from: the group consisting of: niclosamide, closantel, oxyclozanide, rafoxanide, or a pharmaceutically acceptable salt or solvate thereof.

29. The method according to any one of clauses 1 to 26, wherein the halogenated salicylanilide is selected from: the group consisting of: niclosamide and oxyclozanide, or a pharmaceutically acceptable salt or solvate thereof.

30. The method according to any one of clauses 1 to 26, wherein the halogenated salicylanilide is niclosamide, or a pharmaceutically acceptable salt or solvate thereof.

31. The method according to any one of clauses 1 to 30, wherein the H. pylori is resistant to an antibiotic other than the halogenated salicylanilide.

32. The method according to any one of clauses 1 to 30, wherein the H. pylori is resistant to an antibiotic selected from: clarithromycin, amoxicillin, tetracycline, doxycycline, a nitroimidazole, fluoroquinolone, rifabutin, levofloxacin and ciprofloxacin.

33. The method according to any one of clauses 1 to 32, wherein the H. pylori expresses CagA.

34. The method according to any one of clauses 1 to 33, wherein the H. pylori expresses VacA.

35. The method of any one of clauses 1 to 34, wherein the subject is a human.

36. A method for the prevention or treatment of a disease or infection caused by or associated with Helicobacter Spp. in a subject infected with Helicobacter Spp., the method comprising orally administering to the subject an effective amount of a halogenated salicylanilide, or a pharmaceutically acceptable salt or solvate thereof.

37. The method of clause 36 wherein the subject is a non-human animal, for example a companion animal such as a cat or a dog.

38. A method for eradicating a Helicobacter Spp. infection in a subject with a disease or infection caused by or associated with Helicobacter Spp., the method comprising orally administering to the subject an effective amount of a halogenated salicylanilide, or a pharmaceutically acceptable salt or solvate thereof.

39. The method of clause 38 wherein the subject is a non-human animal, for example a companion animal such as a cat or a dog.

40. The method of any one of clauses 1 to 39, wherein the subject is not treated concurrently with an agent that increases the permeability of a bacterial cell membrane.

41. The method of any one of clauses 1 to 40, wherein the subject is not treated concurrently with a bicarbonate.

The invention claimed is:

1. A method for the prevention or treatment of a disease or infection caused by or associated with *H. pylori* in a subject infected with *H. pylori*, the method comprising orally administering to the subject an effective amount of a halogenated salicylanilide, wherein the halogenated salicylanilide is of the formula (I):

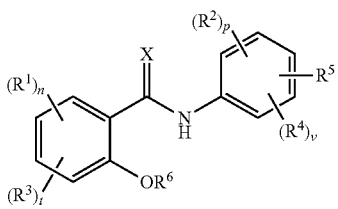

(I)

wherein
X is O or S;
$R^1$ and $R^2$ are at each occurrence independently selected from halo;
$R^3$ and $R^4$ are at each occurrence independently selected from H, $C_{1-6}$ alkyl, —$OR^{41}$, —$NO_2$, and —CN;
$R^5$ is H or -$L^1$-$R^7$;
$R^6$ is H or —$C(O)R^{42}$;
$L^1$ is selected from a bond, O, S, or —$(CR^{43}R^B)_o$—, wherein o is 1 or 2;
$R^7$ is phenyl, unsubstituted or substituted with 1, 2, or 3 groups selected from halo, $C_{1-4}$ alkyl, —$OR^{44}$, —$NO_2$, and —CN;
$R^{41}$, $R^{42}$, $R^{43}$, and $R^{44}$ are at eachoccurrence independently selected from H and $C_{1-4}$ alkyl;
$R^B$ is at each occurrence selected from H, $C_{1-4}$ alkyl, and —CN;
n and p are each independently selected from 0, 1, 2, 3, or 4, with the proviso that n+p is at least 1; and
t and v are independently selected from 0, 1, and 2;
or a pharmaceutically acceptable salt or solvate thereof.

2. The method of claim 1, wherein the subject is not treated concurrently with a proton pump inhibitor or any other antibiotic.

3. The method of claim 1, wherein the subject is treated concurrently with an effective amount of a proton pump inhibitor (PPI).

4. The method of claim 3, wherein the proton pump inhibitor is a benzimidazole or azabenzimidazole derivative.

5. The method of claim 1, wherein the subject is treated concurrently with an effective amount of a nitroimidazole antibiotic.

6. The method of claim 5, wherein the nitroimidazole antibiotic is metronidazole, or a pharmaceutically acceptable salt thereof.

7. The method of claim 5, wherein the subject is treated concurrently with a proton pump inhibitor.

8. The method of claim 1, wherein the subject is not treated concurrently with a bicarbonate.

9. The method of claim 1, wherein the disease or infection caused by or associated with *H. pylori* is selected from: dyspepsia, gastritis, peptic ulcer disease, premalignant gastric lesions, gastric cancer and gastric mucosa-associated lymphoid tissue (MALT) lymphoma.

10. The method of claim 1, wherein the treatment inhibits invasion of *H. pylori* into gastric epithelial cells.

11. The method of claim 1, wherein the treatment reduces or eliminates intracellular *H. pylori* from gastric epithelial cells.

12. The method of claim 1, wherein the treatment inhibits the adhesion of *H. pylori* to gastric epithelial cells.

13. The method of claim 1, wherein the treatment reduces or eliminates *H. pylori* adhered to gastric epithelial cells.

14. The method of claim 1, wherein the treatment inhibits *H. pylori* mediated vacuolation of gastric epithelial cells.

15. A method for eradicating a *H. pylori* infection in a subject with a disease or infection caused by or associated with *H. pylori*, the method comprising orally administering to the subject an effective amount of a halogenated salicylanilide, wherein the halogenated salicylanilide is of the formula (I):

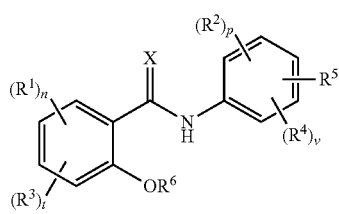

(I)

wherein
X is O or S;
$R^1$ and $R^2$ are at each occurrence independently selected from halo;
$R^3$ and $R^4$ are at each occurrence independently selected from H, $C_{1-6}$ alkyl, —$OR^{41}$, —$NO_2$, and —CN;
$R^5$ is H or -$L^1$-$R^7$;
$R^6$ is H or —$C(O)R^{42}$;
$L^1$ is selected from a bond, O, S, or —$(CR^{43}R^B)_o$—, wherein o is 1 or 2;
$R^7$ is phenyl, unsubstituted or substituted with 1, 2, or 3 groups selected from halo, $C_{1-4}$ alkyl, —$OR^{44}$, —$NO_2$, and —CN;
$R^{41}$, $R^{42}$, $R^{43}$, and $R^{44}$ are at eachoccurrence independently selected from H and $C_{1-4}$ alkyl;
$R^B$ is at each occurrence selected from H, $C_{1-4}$ alkyl, and —CN;
n and p are each independently selected from 0, 1, 2, 3, or 4, with the proviso that n+p is at least 1; and
t and v are independently selected from 0, 1, and 2;
or a pharmaceutically acceptable salt or solvate thereof.

16. The method of claim 15, wherein the disease or infection caused by or associated with *H. pylori* is selected from: dyspepsia, gastritis, peptic ulcer disease, premalignant gastric lesions, gastric cancer and gastric mucosa-associated lymphoid tissue (MALT) lymphoma.

17. A method for eradicating a *H. pylori* infection in a subject, wherein the subject has a premalignant gastric epithelial lesion, the method comprising orally administering to the subject an effective amount of a halogenated salicylanilide, wherein the halogenated salicylanilide is of the formula (I):

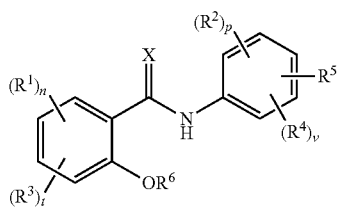

(I)

wherein
X is O or S;
R$^1$ and R$^2$ are at each occurrence independently selected from halo;
R$^3$ and R$^4$ are at each occurrence independently selected from H, C$_{1-6}$ alkyl, —OR$^{41}$, —NO$_2$, and —CN;
R$^5$ is H or -L$^1$-R$^7$;
R$^6$ is H or —C(O)R$^{42}$;
L$^1$ is selected from a bond, O, S, or —(CR$^{43}$R$^B$)$_o$—, wherein o is 1 or 2;
R$^7$ is phenyl, unsubstituted or substituted with 1, 2, or 3 groups selected from halo, C$_{1-4}$ alkyl, —OR$^{44}$, —NO$_2$, and —CN;
R$^{41}$, R$^{42}$, R$^{43}$, and R$^{44}$ are at each occurrence independently selected from H and C$_{1-4}$ alkyl;
R$^B$ is at each occurrence selected from H, C$_{1-4}$ alkyl, and —CN;
n and p are each independently selected from 0, 1, 2, 3, or 4, with the proviso that n+p is at least 1; and
t and v are independently selected from 0, 1, and 2;
or a pharmaceutically acceptable salt or solvate thereof.

18. The method of claim 17, wherein the premalignant gastric epithelial lesion is gastric epithelial dysplasia.

19. A method for treating or preventing atrophic gastritis in a subject infected with *H. pylori*, the method comprising orally administering to the subject an effective amount of a halogenated salicylanilide, wherein the method reduces *H. pylori* induced IL-8 secretion in the subject,
wherein the halogenated salicylanilide is of the formula (I):

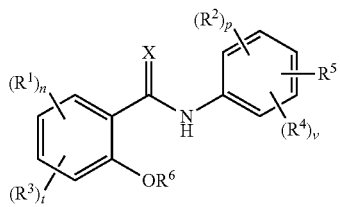

(I)

wherein
X is O or S;
R$^1$ and R$^2$ are at each occurrence independently selected from halo;
R$^3$ and R$^4$ are at each occurrence independently selected from H, C$_{1-6}$ alkyl, —OR$^{41}$, —NO$_2$ and —CN;
R$^5$ is H or -L$^1$-R$^7$;
R$^6$ is H or —C(O)R$^{42}$;
L$^1$ is selected from a bond, O, S, or —(CR$^{43}$R$^B$)$_o$—, wherein o is 1 or 2;
R$^7$ is phenyl, unsubstituted or substituted with 1, 2, or 3 groups selected from halo, C$_{1-4}$ alkyl, —OR$^{44}$, —NO$_2$ and —CN;
R$^{41}$, R$^{42}$, R$^{43}$ and R$^{44}$ are at each occurrence independently selected from H and C$_{1-4}$ alkyl;
R$^B$ is at each occurrence selected from H, C$_{1-4}$ alkyl and —CN;
n and p are each independently selected from 0, 1, 2, 3 or 4, with the proviso that n+p is at least 1; and
t and v are independently selected from 0, 1 and 2;
or a pharmaceutically acceptable salt, or solvate thereof.

20. The method of claim 1, wherein the halogenated salicylanilide is selected from the group consisting of: niclosamide, closantel, oxyclozanide, rafoxanide, or a pharmaceutically acceptable salt or solvate thereof.

21. The method of claim 1, wherein the halogenated salicylanilide is selected from: the group consisting of: niclosamide and oxyclozanide, or a pharmaceutically acceptable salt or solvate thereof.

22. The method of claim 1, wherein the halogenated salicylanilide is niclosamide, or a pharmaceutically acceptable salt or solvate thereof.

23. The method of claim 1, wherein the *H. pylori* is resistant to an antibiotic other than the halogenated salicylanilide.

24. The method of claim 1, wherein the *H. pylori* is resistant to an antibiotic selected from: clarithromycin, amoxicillin, tetracycline, doxycycline, a nitroimidazole, fluoroquinolone, rifabutin, levofloxacin and ciprofloxacin.

25. The method of claim 1, wherein the *H. pylori* expresses CagA.

26. The method of claim 1, wherein the *H. pylori* expresses VacA.

27. The method of claim 1, wherein the subject is a human.

28. The method of claim 3, wherein the proton pump inhibitor is selected from: omeprazole, hydroxyomeprazole, esomeprazole, lansoprazole, dexlansoprazole, pantoprazole, rabeprazole, tenatoprazole, and leminoprazole, or a pharmaceutically acceptable salt, or solvate thereof.

* * * * *

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: vacA-F primer

<400> SEQUENCE: 1
aaacgacaag aagagatcag t                                          21

<210> SEQ ID NO 2
<211> LENGTH: 19
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: vacA-R primer

<400> SEQUENCE: 2
ccagcaaaag gcccatcaa                                             19

<210> SEQ ID NO 3
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: galE-F primer

<400> SEQUENCE: 3
atggcattat tattcacagg                                            20
```

```
<210> SEQ ID NO 4
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: galE-R primer

<400> SEQUENCE: 4
gctccataag gattaatggg                                                   20

<210> SEQ ID NO 5
<211> LENGTH: 23
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: IL8-F primer

<400> SEQUENCE: 5
actgagagtg attgagagtg gac                                               23

<210> SEQ ID NO 6
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: IL8-R primer

<400> SEQUENCE: 6
aaccctctgc acccagtttt c                                                 21

<210> SEQ ID NO 7
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 18 rRNA-F primer

<400> SEQUENCE: 7
cggcgacgac ccattcgaac                                                   20

<210> SEQ ID NO 8
<211> LENGTH: 23
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: 18 rRNA-R primer

<400> SEQUENCE: 8
gaatcgaacc ctgattcccc gtc                                               23
```